(12) United States Patent
Kim et al.

(10) Patent No.: US 10,695,091 B2
(45) Date of Patent: Jun. 30, 2020

(54) SYSTEMS AND METHODS FOR TISSUE CAPTURE AND REMOVAL

(71) Applicant: CLARIA MEDICAL, INC., San Francisco, CA (US)

(72) Inventors: Steven W. Kim, Los Altos, CA (US); Joseph N. Marchesani, Boise, ID (US); Alexey Salamini, San Francisco, CA (US)

(73) Assignee: CLARIA MEDICAL, INC., San Francisco, CA (US)

( * ) Notice: Subject to any disclaimer, the term of this patent is extended or adjusted under 35 U.S.C. 154(b) by 0 days.

(21) Appl. No.: 16/169,884

(22) Filed: Oct. 24, 2018

(65) Prior Publication Data
US 2019/0059948 A1   Feb. 28, 2019

Related U.S. Application Data

(63) Continuation of application No. PCT/US2017/029162, filed on Apr. 24, 2017, now abandoned.
(Continued)

(51) Int. Cl.
*A61B 17/42* (2006.01)
*A61B 17/221* (2006.01)
(Continued)

(52) U.S. Cl.
CPC .......... *A61B 17/42* (2013.01); *A61B 17/221* (2013.01); *A61B 2017/00287* (2013.01);
(Continued)

(58) Field of Classification Search
CPC . A61B 17/42; A61B 17/221; A61B 17/00234; A61B 17/32002; A61B 2017/00287
See application file for complete search history.

(56) References Cited

U.S. PATENT DOCUMENTS 5,037,379 A     8/1991 Clayman et al.
5,368,545 A  *  11/1994 Schaller .......... A61B 17/00234
                                                    128/846
(Continued)

FOREIGN PATENT DOCUMENTS

WO   WO 16/028430    7/2015
WO   WO 16/058086    10/2015
(Continued)

OTHER PUBLICATIONS

International Search Report and Written Opinion dated Aug. 24, 2017 in International Application No. PCT/US2017/029162, filed Apr. 24, 2017.
(Continued)

*Primary Examiner* — Tuan V Nguyen
(74) *Attorney, Agent, or Firm* — Schmeiser, Olsen & Watts LLP

(57) ABSTRACT

Components, systems and kits for capturing and removing tissue from mammalian bodies include a tissue container that may be introduced into a body cavity and within which a tissue specimen may be placed, cut and removed from the body cavity. Methods of using these components, systems and kits are also described.

15 Claims, 41 Drawing Sheets

Related U.S. Application Data

(60) Provisional application No. 62/419,342, filed on Nov. 8, 2016.

(51) Int. Cl.
*A61B 17/00* (2006.01)
*A61B 90/00* (2016.01)
*A61B 17/32* (2006.01)
*A61B 17/3207* (2006.01)

(52) U.S. Cl.
CPC ............ *A61B 2017/00876* (2013.01); *A61B 2017/2215* (2013.01); *A61B 2017/320024* (2013.01); *A61B 2017/320775* (2013.01); *A61B 2017/4216* (2013.01); *A61B 2090/0807* (2016.02)

(56) References Cited

U.S. PATENT DOCUMENTS

| | | | |
|---|---|---|---|
| 5,618,296 A * | 4/1997 | Sorensen | A61B 17/32002 606/167 |
| 5,735,289 A | 4/1998 | Pfeffer et al. | |
| 5,814,044 A * | 9/1998 | Hooven | A61B 17/32002 604/21 |
| 6,045,566 A * | 4/2000 | Pagedas | A61B 17/32002 606/114 |
| 6,387,102 B2 | 5/2002 | Pagedas | |
| 6,468,228 B1 * | 10/2002 | Topel | A61B 17/32053 600/564 |
| 8,821,377 B2 | 9/2014 | Collins | |
| 9,044,210 B1 | 6/2015 | Hoyte et al. | |
| 9,522,034 B2 | 12/2016 | Johnson et al. | |
| 9,649,147 B2 | 5/2017 | Gilbert et al. | |
| 10,179,004 B2 | 1/2019 | Thomas et al. | |
| 2007/0135780 A1 | 6/2007 | Pagedas | |
| 2008/0255597 A1 * | 10/2008 | Pravong | A61B 17/32002 606/169 |
| 2009/0043315 A1 * | 2/2009 | Moon | A61B 17/00234 606/114 |
| 2011/0054260 A1 | 3/2011 | Albrecht et al. | |
| 2012/0316572 A1 | 12/2012 | Rosenblatt et al. | |
| 2013/0046140 A1 | 2/2013 | Pravong et al. | |
| 2013/0123797 A1 | 5/2013 | Livneh | |
| 2013/0131457 A1 | 5/2013 | Seckin | |
| 2013/0190773 A1 | 7/2013 | Carlson | |
| 2013/0253267 A1 * | 9/2013 | Collins | A61B 17/221 600/104 |
| 2014/0046337 A1 | 2/2014 | O'Prey et al. | |
| 2015/0018815 A1 | 1/2015 | Sartor et al. | |
| 2015/0018837 A1 * | 1/2015 | Sartor | A61B 17/32002 606/114 |
| 2015/0272620 A1 | 10/2015 | Zisow | |
| 2015/0297254 A1 | 10/2015 | Sullivan et al. | |
| 2015/0305772 A1 | 10/2015 | McCauley | |
| 2015/0320409 A1 | 11/2015 | Lehmann et al. | |
| 2015/0335342 A1 * | 11/2015 | Hart | A61B 17/32002 606/171 |
| 2016/0030073 A1 | 2/2016 | Isakov et al. | |
| 2016/0045214 A1 | 2/2016 | Sullivan et al. | |
| 2016/0095613 A1 | 4/2016 | Trondle | |
| 2016/0100857 A1 * | 4/2016 | Wachli | A61B 17/3439 600/204 |
| 2016/0135798 A1 * | 5/2016 | Macleod | A61B 17/00234 606/114 |
| 2016/0199050 A1 | 7/2016 | Radl et al. | |
| 2016/0262794 A1 | 9/2016 | Wachli et al. | |
| 2016/0302783 A1 | 10/2016 | Greenberg et al. | |
| 2016/0338682 A1 | 11/2016 | Hoyte et al. | |
| 2017/0224321 A1 | 8/2017 | Kessler et al. | |
| 2018/0090889 A1 | 3/2018 | Fuchs et al. | |

FOREIGN PATENT DOCUMENTS

| | | |
|---|---|---|
| WO | WO 17/189442 | 11/2017 |
| WO | WO 19/083896 | 5/2019 |

OTHER PUBLICATIONS

International Preliminary Report on Patentability dated Oct. 30, 2018 in International Application No. PCT/US2017/029162, filed Apr. 24, 2017.
International Search Report and Written Opinion dated Jan. 15, 2019 in International Application No. PCT/US2018/056915, filed Oct. 22, 2018.
Arkenbout et al., "Design Process of a Trans-Vaginal Morcellator for Total Laparoscopic Hysterectomy (from clinical functionality assessment to first prototype)" Feb. 1, 2012.
Elshal et al. "Towards optimization prostate tissue retrieval following holmium laser enucleation of the prostate (HoLEP): Assessment of two morcellators and review of literature," Canadian Urological Journal Association Journal, Journal De L'Association Des Urologues Du Canada Nov. 2007, vol. 9, No. 9-10, Sep. 9, 2015 p. 618 Canada.
Supplementary Partial European Search Report dated Dec. 16, 2019 in European Application No. EP17790193.1 filed: Apr. 24, 2017 based on International Patent Application No. PCT/US2017/029162 filed: Apr. 24, 2017.

* cited by examiner

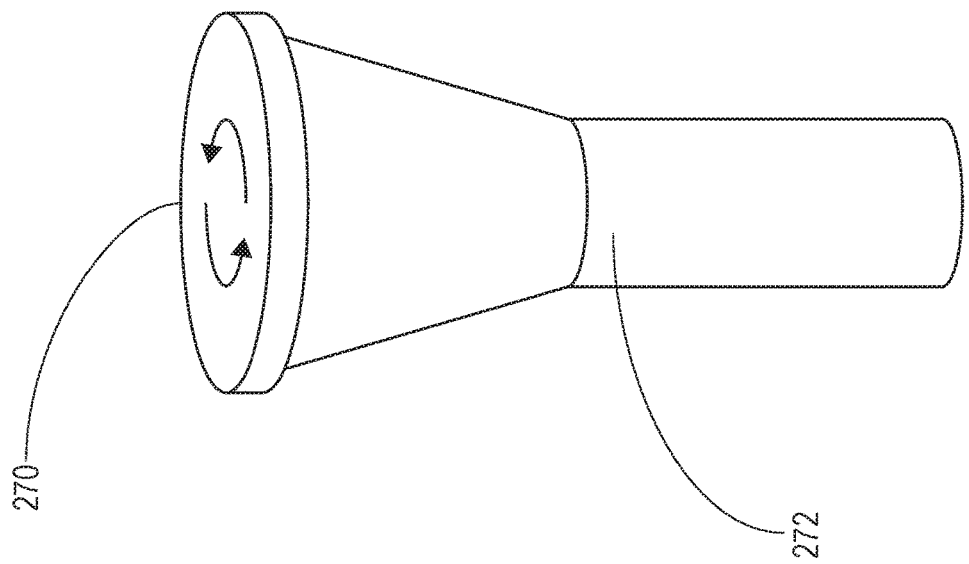
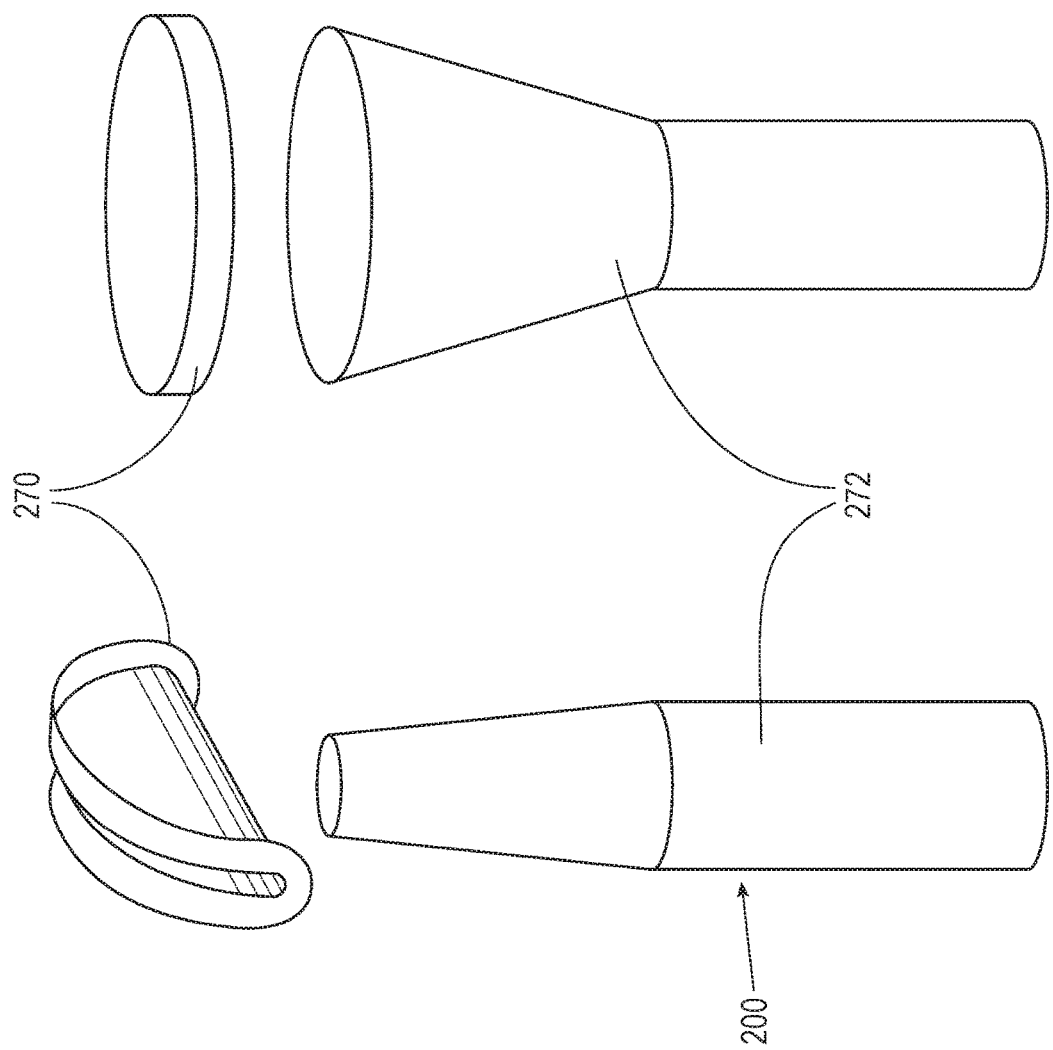
FIGURE 8A  FIGURE 8B  FIGURE 8C

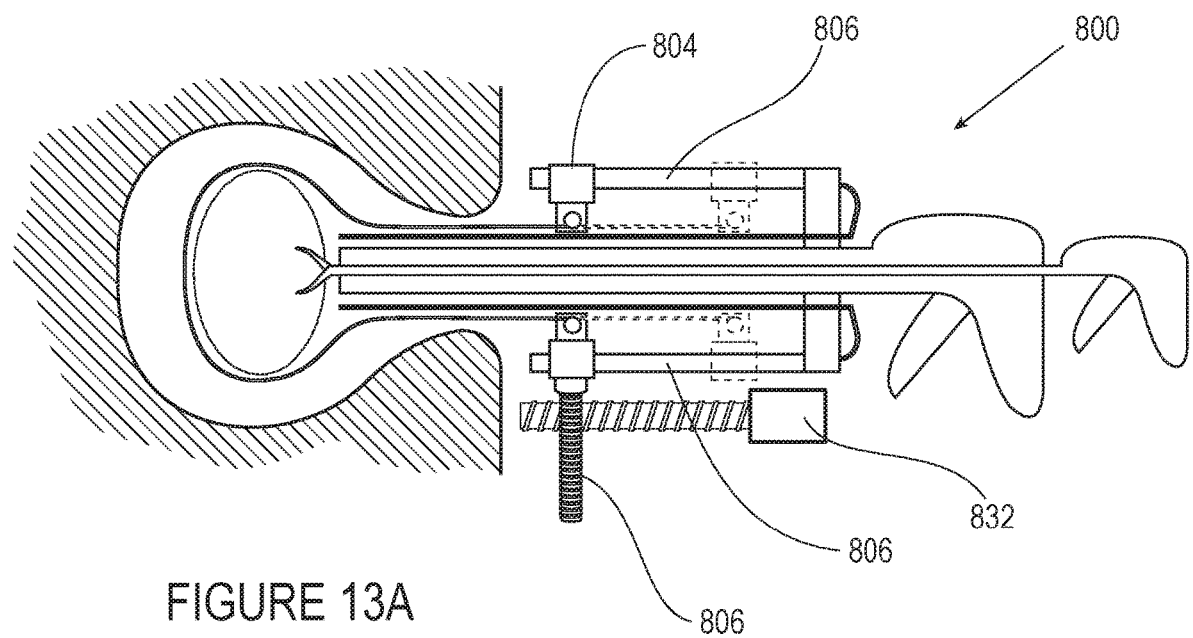
FIGURE 13A
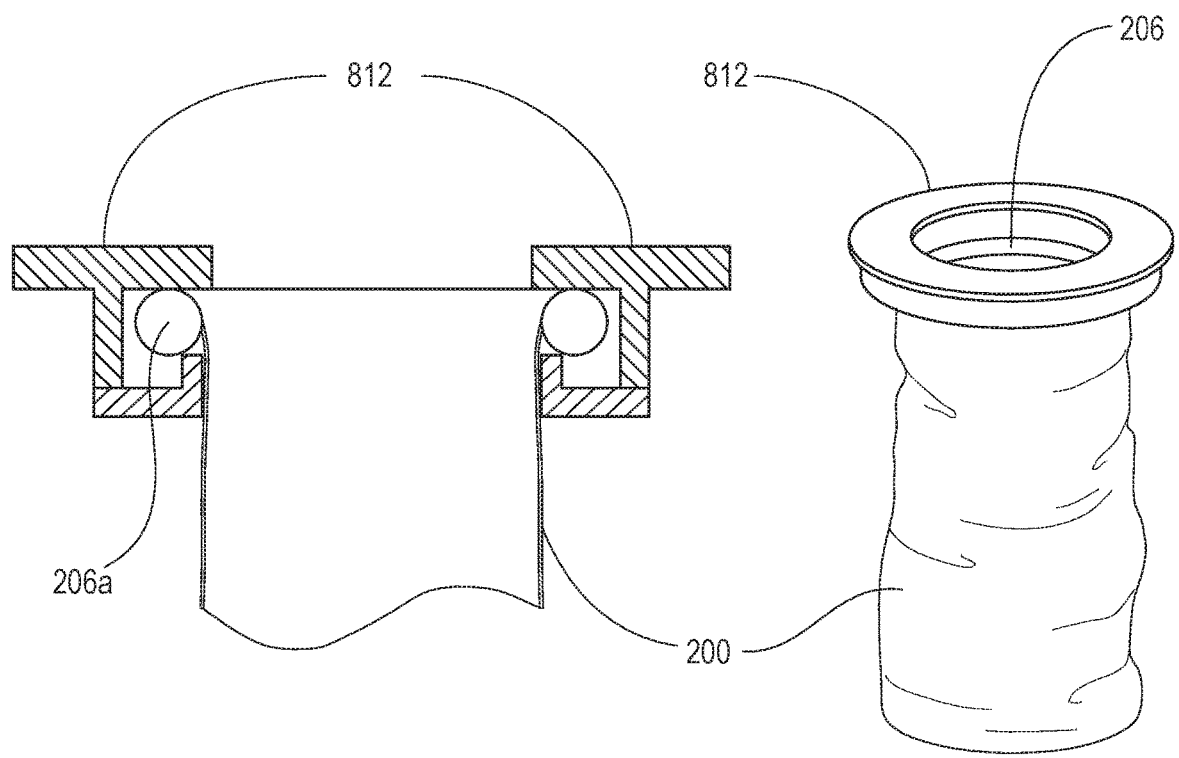
FIGURE 13B
FIGURE 13C

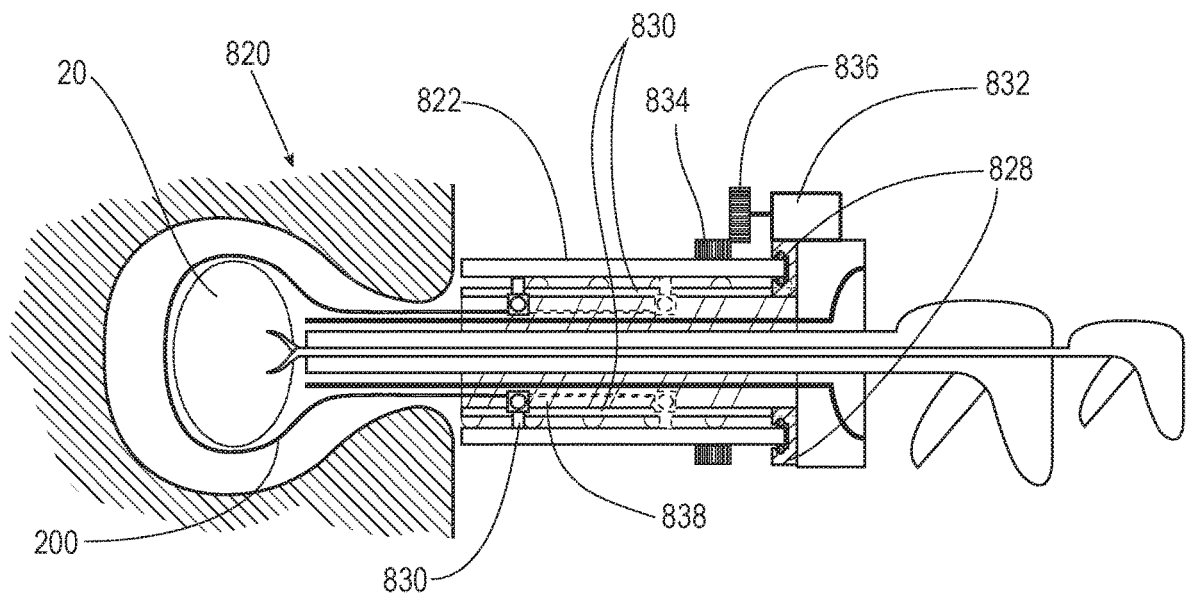
FIGURE 14A
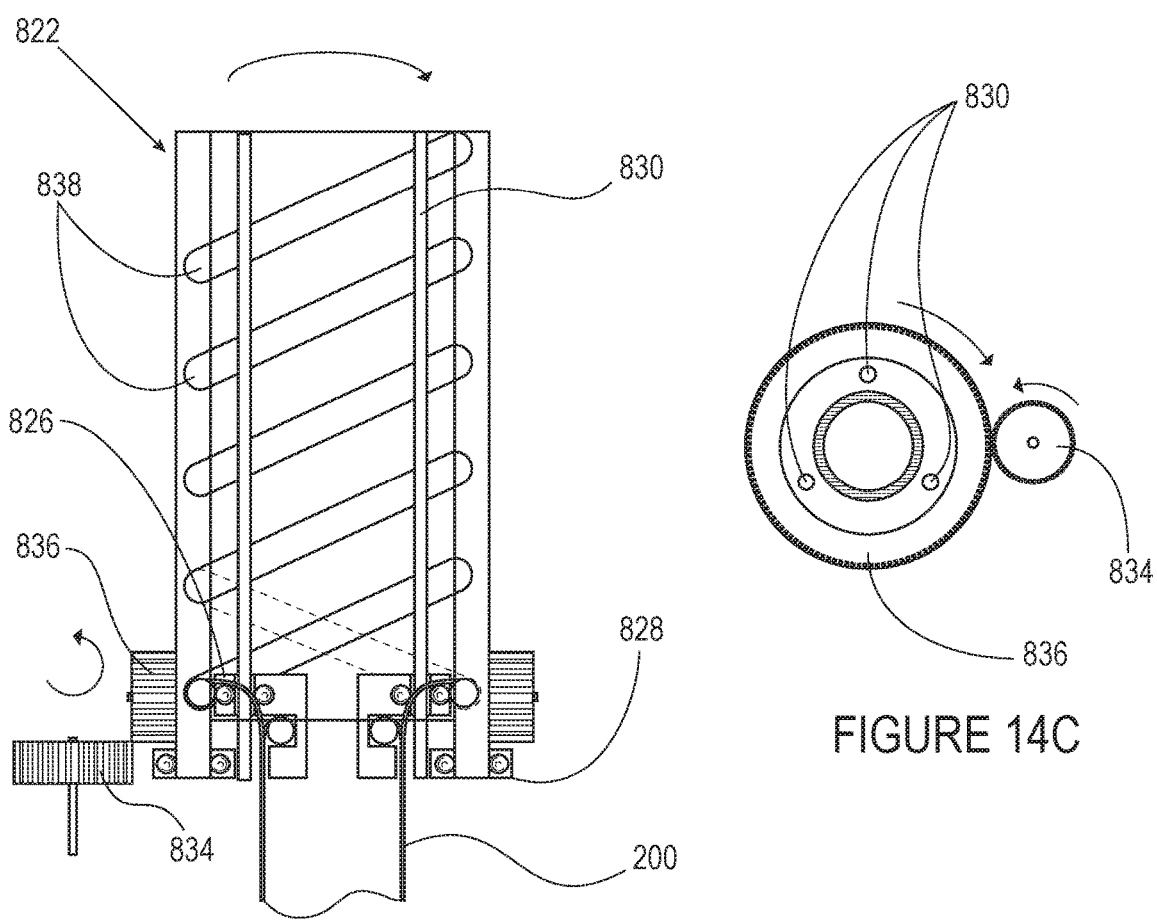
FIGURE 14B
FIGURE 14C

SYSTEMS AND METHODS FOR TISSUE CAPTURE AND REMOVAL

RELATED APPLICATIONS

The present application is a continuation of and claims priority under 35 U.S.C. section 120 to International Patent Application Serial No. PCT/US2017/029162, filed Apr. 24, 2017, naming Steven W. Kim et al. as inventors, titled "SYSTEMS AND METHODS FOR TISSUE CAPTURE AND REMOVAL", which claims the benefit of U.S. Provisional Application No. 62/326,836, filed Apr. 25, 2016 and U.S. Provisional Application No. 62/419,342, filed Nov. 8, 2016, each of which is hereby incorporated in its entirety by reference.

FIELD OF THE INVENTION

The technology relates to the field of removal of tissue specimens from a mammalian body and, more particularly, to methods and systems for capturing and containing tissue specimens, their morcellation, and safe removal from the body.

BACKGROUND

In the field of health care in human and veterinary medicine, it is often desirable or even necessary to remove tissue from a patient's body. Such tissue, typically in the form of mass, tumor, or organ, some of which may be cancerous, pre-cancerous, or be suspected of being cancerous or pre-cancerous, may be removed via traditional surgical techniques, including open surgery and minimally invasive approaches.

Among minimally invasive approaches, laparoscopic procedures in which a tissue specimen is removed via a small incision using specialized tools are well known. Minimally invasive procedures such as laparoscopy and mini-laparotomy may also employ the use of tools operated robotically. Among procedures performed via minimally invasive techniques include those performed in the abdominal, pelvic and thoracic cavities. Cholecystectomies, nephrectomies, colectomies, hysterectomies, and other procedures in gastrointestinal, gynecological and urological categories are common as are minimally invasive arthroscopy, cystoscopy, and thoracoscopy procedures. Among the various advantages cited with minimally invasive procedures include reduced pain, lower risk of infection, shorter recovery times, and lower cost, among others.

Often, the tissue specimen to be removed via minimally invasive procedures is larger than the incisions used. As such, techniques have been developed to safely remove such specimens while maintaining the advantages of a minimally invasive approach. One such technique is morcellation, in which the tissue specimen is cut or processed into pieces while still inside the patient so that they may be more readily removed. Morcellation historically has been accomplished manually via traditional surgical approaches (i.e. not via minimally invasive approaches), with the physician or other user operating morcellators by squeezing a handle or the like; even direct cutting of the tissue specimen via a scalpel or other instrument through the surgically-created tissue orifice, such as a surgical incision, vaginal cuff, etc. is performed. Power morcellation, in which a morcellation device operated by electricity or other means, is another commonly employed technique.

In the field of gynecology, the hysterectomy is a common procedure that is performed in approximately 500,000 women per year in the United States alone. It involves removing a woman's uterus for a variety of reasons, most commonly because of the presence of uterine fibroids. Such hysterectomies may be performed via traditional open surgical techniques or minimally invasive techniques, such as laparoscopy with the use of morcellation. Hysterectomies may be partial, involving removal of, e.g., only the uterus, or total, in which the uterus and uterine cervix are both removed. In either case, the ovaries and/or the fallopian tubes may or may not simultaneously be removed.

For years, power morcellation has been used in gynecologic surgery to remove large uteri from patients via small holes, as is necessary in minimally invasive surgery. The most common application of power morcellation in gynecologic surgery involved morcellating a large, fibroid uterus to remove it from a patient's body during robot-assisted total laparoscopic hysterectomy, although there are a number of other applications as well.

Since hysterectomy involving an enlarged uterus is very common, and since minimally invasive surgery offers many benefits to the patient, surgeon, hospital, and payer, the use of power morcellation had become commonplace. However, the potential for occult cancers hidden within the uterus that cannot be detected preoperatively and that could potentially be spread around the patient's body with grave consequences during morcellation has been a source of concern. As such, even though most hysterectomies are associated with uteri that do not involve any actual or suspected cancer, traditional open surgery, with its added risk, complication rates, longer hospitalizations, more difficult recoveries, etc., is prevalent.

Therefore, techniques and systems are desirable that afford safe removal and processing of tissue specimens, even in the possible presence of an occult malignancy.

In approaching this problem, systems and methods of the present disclosure improve the safety, speed, ease of use, and efficiency of the tissue removal process via minimally invasive approaches, both in gynecological and non-gynecological applications.

SUMMARY

The present disclosure embodies various methods, component, systems and kits for capturing and removing tissue from mammalian bodies.

In one embodiment, a method of the present disclosure includes introducing at least a portion of a tissue container into a patient's pelvic cavity through the patient's vagina, placing a tissue specimen into an interior of the tissue container, removing at least a portion of the tissue container from the pelvic cavity through the vagina such that an edge defining an opening in the tissue container is outside the vagina, introducing a cutter into the container interior through the vagina, cutting at least a portion of the tissue specimen with the cutter; and removing the tissue specimen from the container interior and out of vagina through the cutter. A cannula may be introduced at least partially into the container interior through a central lumen of the cannula. In addition, a tissue grasper may be released at least partially into the container interior through either or both the cannula central lumen or a central lumen of the cutter. The tissue grasper may be used to grasp at least a portion of the tissue specimen prior to or during the step of cutting at least a portion of the tissue specimen with the cutter. The tissue grasper may be introduced at least partially into the container interior through the vagina. The step of grasping at least a portion of the tissue specimen may include drawing the tissue specimen into contact with a blade of the cutter prior to or during the cutting step. A guard may be deployed within the container interior, prior to or concurrently with the step of introducing the cutter, to protect the tissue container from damage. The guard may be expandable from a collapsed configuration such that when the guard is deployed within the container interior it expands into a cone shape. The cutter may comprise a guard for protecting the tissue container from damage prior to or during the cutting step and may also comprise a protector portion having at least one protector element. The cannula may comprise a protector portion having an asymmetric extension, or the cannula may include a protector portion comprises an enclosing element at least partially covering the protector element and/or the asymmetric extension. In this method, at least a portion of the tissue container may be removed from the pelvic cavity through the vagina such that tissue specimen is thereby moved in apposition to or near the cutter. Tension may be applied to at least a portion of the tissue container prior to or concurrently with cutting at the portion of the tissue. This tension can be applied by an operator physically applying tension on the container by hand, by pulling on one or more tethers attached to the container, by a twisting motion that shortens an axial length of the container, and/or by an automated system. The tissue specimen can include at least one of a uterus, ovary, and fallopian tube. In addition, the method can employ at least one laparoscopic instrument that is introduced through one or more ports and into the pelvic cavity to prepare and/or visualize the tissue specimen prior to the step of placing the tissue specimen container interior. The laparoscopic instrument may also be used to place or assist placing the tissue specimen into the tissue container.

One embodiment includes a tissue containment and removal system having an expandable tissue container with an interior, a tissue cutter having a distal end that is at least partially disposable within the container interior and a guard that is deployable within the container interior and over the cutter distal end such that the guard is between the container interior and the cutter. The system can also include a cannula at least partially disposable within the container interior. The cannula can have a central lumen through which the cutter may be disposed. The guard may be partially collapsible and expandable into a cone shape upon deployment within the container interior. The system can also include a tissue grasper that is at least partially disposable within the container interior and/or at least partially disposable within and axially movable through the cannula lumen. The tissue grasper can be at least partially disposable within and axially movable through a central lumen of the tissue cutter.

One embodiment includes a tissue containment and removal system having an expandable tissue container with an interior, a tissue cutter having a distal end that is at least partially disposable within the container interior and a cannula at least partially disposable within the container interior. The cannula can have a main portion, a protector portion and a central lumen through which the cutter may be disposed. The cannula protector portion can comprise at least one protector element and/or at least one asymmetric extension. The cannula protector portion can further include an enclosing element at least partially covering the protector element and/or the asymmetric extension. The system can also include a tissue grasper that is at least partially disposable within the container interior and/or at least partially disposable within and axially movable through the cannula lumen. The tissue grasper can be at least partially disposable within and axially movable through a central lumen of the tissue cutter.

One embodiment includes a tissue containment and removal system having an expandable tissue container with an interior, a tissue cutter having a distal end that is at least partially disposable within the container interior and a cannula at least partially disposable within the container interior. The cannula can have a central lumen through which the cutter may be disposed. The system can also include a guard that is deployable within the container interior and over the cutter distal end such that the guard, when deployed, is disposed between the container interior and the cutter. The guard may comprise at least one protector element and/or an asymmetric extension and/or an enclosing element at least partially covering the at least one protector element and/or the asymmetric extension. The system may also include a tissue grasper at least partially disposable within and axially moveable through the container interior and/or at least partially disposable within and axially movable through the cannula lumen. The tissue grasper may also be at least partially disposable within and axially movable through a central lumen of the tissue cutter.

One embodiment includes a tissue containment and removal system having an expandable tissue container with an interior, and a tissue cutter having a distal end that is at least partially disposable within the container interior, the cutter comprising a main portion and a protector portion. The cutter protector portion can include at least one protector element and/or an asymmetric extension and/or an enclosing element at least partially covering the at least one protector element. The system may also include a tissue grasper at least partially disposable within the container interior and which may be at least partially disposable within and axially movable through the cannula central lumen. The system may also include a cannula at least partially disposable within the container interior and having a central lumen through which the tissue cutter may be disposed. The tissue grasper may also be at least partially disposable within and axially movable through the cannula central lumen and/or through a central lumen of the tissue cutter.

One embodiment includes a tissue containment system having a collapsible tissue container with at least one opening, a closure mechanism, and at least one reinforcing member selected from the group consisting of a reinforcing member having a curved cross-sectional profile, a reinforcing member that extends radially outward relative to a central longitudinal axis of the container, and a reinforcing member that is a helically-shaped expansion spring. The container can be impermeable to the transmission or leakage of biological cells, and can be a composite structure. The container can also be a bi-layer structure. If the container is a composite or a bi-layer structure, a first inner layer may be present that is resistant to cutting and puncturing, such as, e.g., poly-paraphenylene terepthalamide. One or more tethers may also be part of the container and may be affixed to the container. The closure mechanism may be selected from the group comprising a zipper, a tongue and groove closure, a clasp, a string tie, a hook and loop fastener, a clasp, a drawstring, and a drawstring with a reinforcing member. A closure member can be included which is operable to move a zipper mechanism to close the at least one opening. The closure mechanism may be operated from a location outside the body of a patient when the container is disposed at least partially therewithin. The container opening may generally be circular, and an edge of the container near the opening can have at least one stiffening member. The tissue container opening can also generally be triangular and an edge of the container near the opening can have two stiffening members. The system can also include a container tensioning mechanism. The tensioning mechanism can be operable by a hand crank or by an automated system comprising a motor and a programmable control module. The container may be deployed in a radial fashion by the manipulation of one or more wires to create a container interior into which a tissue specimen may be placed, and motion of the one or more wires around an approximate 360 degree path allows an edge of container to mate with itself to close the container. The system may also include a handle disposed near the container opening. The handle may be integrally formed with the container or it may be configured to be attached to the container by a user.

In one embodiment, a method of tissue removal includes the steps of introducing at least a portion of a tissue container into a body cavity through a body port, placing a tissue specimen into an interior of the tissue container, removing at least a portion of the tissue container from the body cavity such that an edge defining an opening in the tissue container is outside the port, introducing a cutter into the container interior through the port, cutting at least a portion of the tissue specimen with the cutter, and removing the tissue specimen from the body cavity through the cutter. The body cavity may be a pelvic cavity and the tissue specimen is one or more tissue specimens selected from the group consisting of a uterus, a fallopian tube, and an ovary. The body port may be selected from the group consisting of a surgical incision, a trocar, and a vagina. The body cavity can also be an abdominal cavity and the tissue specimen can be selected from the group consisting of solid and hollow viscera found within the abdominal cavity, including without limitation small intestines, large intestines, colon, rectum, liver, bladder, omentum, abdominopelvic sidewalls, and any other abdominal organ or any solid or cystic tumor or lesion associated with any of the foregoing. The body cavity can also be a thoracic cavity and the tissue specimen can be selected from the group consisting of solid and hollow viscera found within the thoracic cavity, including without limitation cardiac tissue, lungs, bronchi, other pulmonary tissue, esophageal tissue, vessels, lymph-associated tissue, and any other thoracic organ or any solid or cystic tumor or lesion associated with any of the foregoing. The body cavity can also be a retroperitoneal space and the tissue specimen may be selected from the group consisting of solid and hollow viscera found within the retroperitoneal space, including without limitation kidneys, adrenal glands, spleen, ureters, muscles, vessels, lymph associated tissue, and any other retroperitoneal organ or any solid or cystic tumor or lesion associated with any of the foregoing.

In one embodiment, a method for isolating and removing tissue from a mammalian body includes the steps of inserting a cannula through a at least partially through a tissue port to an ostium of a tissue cavity, deploying a specimen bag through the cannula into the tissue cavity, placing a tissue specimen into an interior of the bag with a tissue grasper, the grasper having been deployed at least partially into the tissue cavity through the cannula or through a second tissue port, deploying a guard through the cannula into the bag interior, inserting a cutter through the cannula into an interior space of the guard proximal to a distal end of the guard, moving the tissue specimen against a blade of the cutter with the tissue manipulator, actuating the cutter while applying tension on the bag against the tissue cavity surface such that the tissue specimen is at least partially dissected, distally retracting the cutter and tissue manipulator from the bag, closing the bag, removing the closed bag containing the at least partially dissected tissue specimen by distally retracting the bag through the cannula, and removing the cannula from the tissue port.

One embodiment includes a tissue containment and removal kit having an expandable tissue container with an interior, a tissue cutter comprising a distal end that is at least partially disposable within the container interior, a guard that is deployable within the container interior and over the cutter distal end such that the guard is between the container interior and the cutter, and instructions for use.

One embodiment includes a tissue containment and removal kit having an expandable tissue container with an interior, a tissue cutter comprising a distal end that is at least partially disposable within the container interior, a guard that is deployable within the container interior and over the cutter distal end such that the guard is between the container interior and the cutter, and instructions for use.

One embodiment includes a tissue containment and removal kit having an expandable tissue container with an interior, a tissue cutter comprising a distal end that is at least partially disposable within the container interior, a cannula disposable within the container interior, the cannula having a central lumen through which the cutter may be disposed, a guard that is deployable within the container interior and over the cutter distal end such that the guard is between the container interior and the cutter, and instructions for use.

One embodiment includes a tissue containment and removal kit having an expandable tissue container having an interior, a tissue cutter comprising a distal end that is at least partially disposable within the container interior, the cutter comprising a main portion and a protector portion, and instructions for use.

In one embodiment, a method of capturing and removing tissue includes introducing at least a portion of a tissue container into a patient's pelvic cavity through a laparoscopic port, placing a tissue specimen into an interior of the tissue container, removing at least a portion of the tissue container from the pelvic cavity through the laparoscopic port such that an edge defining an opening in the tissue container is outside the laparoscopic port, introducing a cutter into the container interior through the laparoscopic port, cutting at least a portion of the tissue specimen with the cutter, and removing the tissue specimen from the container interior and out of the laparoscopic port through the cutter. The method may also include the step of introducing a cannula at least partially into the container interior, wherein the cutter is introduced into the container interior through a central lumen of the cannula. The method may also include the steps of introducing a tissue grasper at least partially into the container interior through either or both the cannula central lumen or a central lumen of the cutter and grasping at least a portion of the tissue specimen with the tissue grasper prior to or during the step of cutting at least a portion of the tissue specimen with the cutter. The method may also include the steps of introducing a tissue grasper at least partially into the container interior through the laparoscopic port and grasping at least a portion of the tissue specimen with the tissue grasper prior to or during the step of cutting at least a portion of the tissue specimen with the cutter. When grasping at least a portion of the tissue specimen, the method can mean this to include drawing the tissue specimen into contact with a blade of the cutter prior to or during the cutting step. The method may further include the step of deploying a guard within the container interior, prior to or concurrently with the step of introducing the cutter, to protect the tissue container from damage. The cutter may comprise a guard for protecting the tissue container from damage prior to or during the cutting step. The cannula may include a protector portion having at least one protector element and/or an asymmetric extension. The cannula protector portion may also include an enclosing element at least partially covering the at least one protector element and/or the asymmetric extension. The guard may be expandable from a collapsed configuration such that when the guard is deployed within the container interior it expands into a cone shape. The method may also include the feature that wherein when at least a portion of the tissue container is removed from the pelvic cavity through the laparoscopic port, the tissue specimen is thereby moved in apposition to or near the cutter. Further, the method may include the step of applying tension to at least a portion of the tissue container prior to or concurrently with cutting at the at least one portion of the tissue. This tension may be applied by an operator physically applying tension on the container by hand, by pulling on one or more tethers attached to the container, by a twisting motion wherein the twisting motion shortens an axial length of the container. This tension may also by a semi-automated or an automated system. The tissue specimen can include at least one of a uterus, ovary, and fallopian tube. At least one laparoscopic instrument can be introduced through one or more additional laparoscopic ports and into the pelvic cavity; such instrument may be used in the method to prepare and/or visualize the tissue specimen prior to the step of placing the tissue specimen container interior. This laparoscopic instrument can also be used to place or assist placing the tissue specimen into the tissue container.

In one embodiment, a method of tissue removal includes the steps of introducing at least a portion of at least one tissue container into a body cavity through a body port, placing a tissue specimen into an interior of the at least one tissue container, removing at least a portion of the at least one tissue container from the body cavity such that an edge defining an opening in the at least one tissue container is outside the port, introducing a cutter into the at least one container interior through the port, cutting at least a portion of the tissue specimen with the cutter, and removing the tissue specimen from the body cavity through the cutter. The method may further include the step of applying tension to at least a portion of the at least one tissue container prior to or concurrently with cutting at the at least one portion of the tissue. Such tension may impart a force on the tissue specimen to bring the specimen in apposition with the cutter. One embodiment includes a tissue containment and removal system that is capable of performing any of the steps of this method.

In one embodiment, a method of tissue removal includes the steps of introducing at least a portion of a tissue container into a body cavity through a body port, placing a tissue specimen into an interior of the tissue container, removing at least a portion of the tissue container from the body cavity such that an edge defining an opening in the tissue container is outside the port, introducing a cutter and a locking member into the container interior through the port, cutting at least a portion of the tissue specimen with the cutter, and removing the tissue specimen from the body cavity through the cutter. The method may include embodiments in which the locking member is an inflatable balloon and further includes the step of inflating the balloon prior to the cutting step. The method may also include the step of applying tension to at least a portion of the tissue container prior to or concurrently with cutting at the at least one portion of the tissue, and this tension may impart a force on the tissue specimen to bring the specimen in apposition with the cutter. The method may also include the step of introducing a cannula into the container interior through the port, and such cannula may be introduced prior to or simultaneously with the introduction of the cutter. The cutter may be introduced through a central lumen of the cannula. The locking member can be disposed on the cannula, and the locking member may be an inflatable balloon. The locking member may be configured to prevent contact between the container and the cutter. The method may further include the step of inflating the balloon prior to the cutting step. The balloon may anchor the cannula to a portion of the body cavity prior to or concurrent with the step of removing the tissue specimen. One embodiment includes a tissue containment and removal system that is capable of performing any of the steps of this method.

BRIEF DESCRIPTION OF THE DRAWINGS

FIGS. 8A-C depict the operation of a two-part tissue container.

FIGS. 13A-C depict the operation of a tissue container utilizing a telescoping-to-tension feature.

FIGS. 14A-C depict the operation of a tissue container utilizing a camera-like twist-to-tension feature.

DETAILED DESCRIPTION

Figure 1:
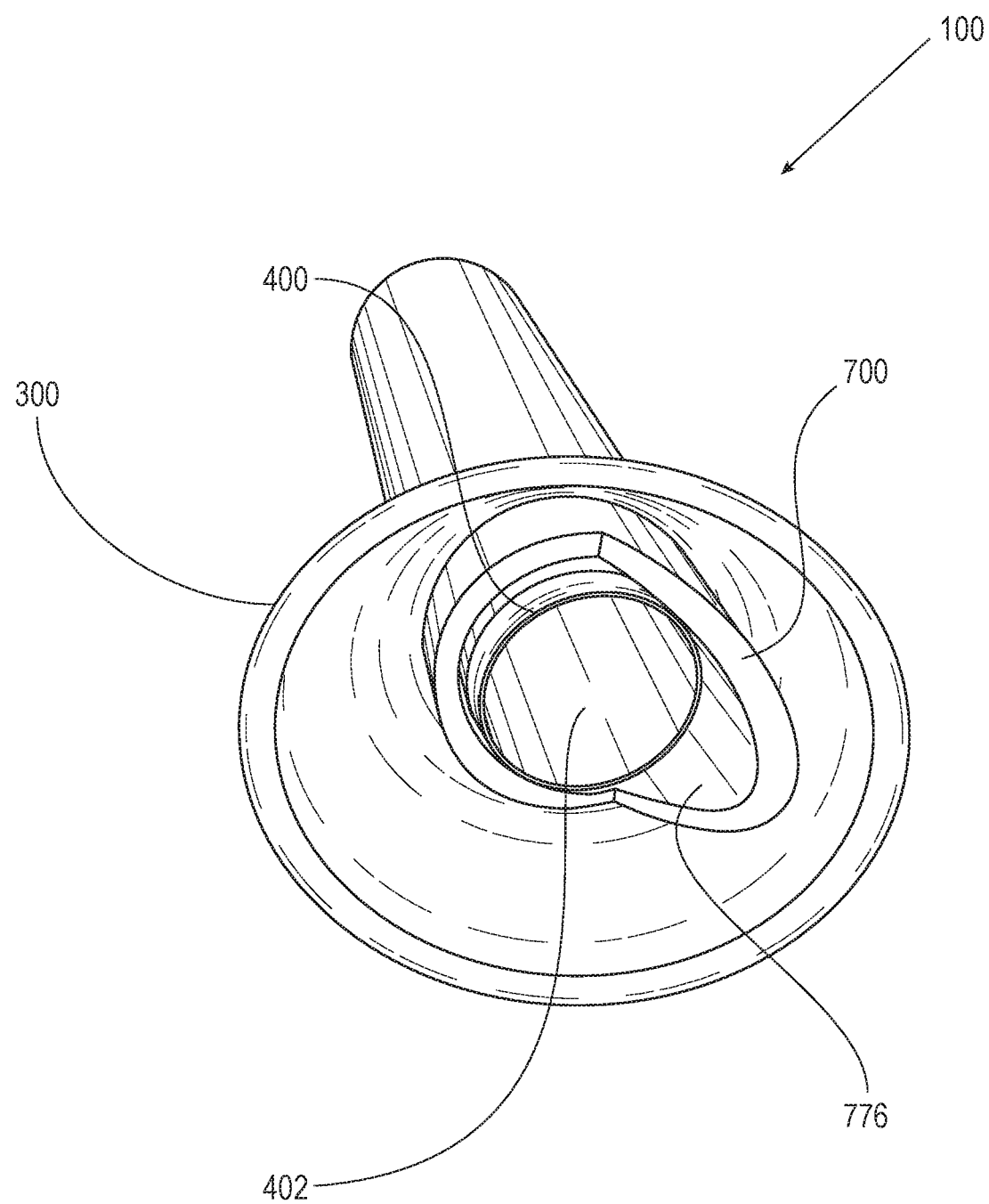
FIG. 1 is a perspective view of an embodiment of a system for tissue capture and removal, not including a tissue container for clarity.

The following description should be read with reference to drawings in which similar elements in different drawings are numbered the same. The drawings, which are not necessarily to scale, depict illustrative embodiments and are not intended to limit the scope of the present disclosure.

Embodiments of the present disclosure are fundamentally different than any previous iteration of tissue access and removal involving morcellation, particularly power morcellation: in the context of a hysterectomy, for example, embodiments disclosed herein are the first that may be deployed into the pelvic or pelvic cavity through the vagina, once the uterus and cervix have been dissected off the top of the vagina. In contrast, previous power morcellators have only been used through an abdominal laparoscopic port, which renders them not only cumbersome, difficult, and awkward to operate, but is limited to removing tissue pieces whose maximum size is that of the port, typically on the order of about 12.0 mm in diameter. Embodiments of the present disclosure have the advantage that they can be deployed, in the gynecologic context, trans-vaginally, thus affording a physician or other user the ability to remove tissue pieces as large as the surgical opening in the vagina itself, typically on the order of about 30.0 to about 60.0 mm in diameter. The number of "passes", or cycles of tissue cutting or morcellation needed to remove a specimen, can therefore decrease from dozens to a handful, with concomitant savings in total operative time & patient anesthesia exposure (and corresponding costs).

As such, embodiments of the present disclosure allow for ready tissue specimen capture within an enclosure such as a container or bag, relatively simple and safe tissue cutting/processing/morcellation within the bag, and a design that protects the container from being breached by the tissue cutter/morcellator or other instrument. Indeed, outside the transvaginal context, smaller versions of systems described herein can be deployed via a pelvic, abdominal or other laparoscopic port for use in applications where no vaginal access is possible.

In general, system embodiments of the present disclosure can could consist of one component, two distinct components, three distinct components or more, or a combination of 2 or 3 or more distinct components. A particular function may be, in some embodiments, performed by different components or multiple components operating together, depending on the system configuration and the particular application for which that configuration is designed.

A two-part system could consist of a specimen container and a tissue cutting device, for example. The container can generally be leak-proof and impermeable to cells, liquids, gases, etc., and can function to prevent the spread of cancerous or otherwise dangerous biological materials into the patient's body cavity during the act of specimen removal. The container can include features that protect the surrounding healthy tissue from being damaged by accidental contact with the cutter or other instrument and that enable swift and efficient specimen containment. The tissue cutter or morcellator can safely interface with the container for the purpose of removing the specimen from the patient's body. Using one configuration of such a two-part system, a physician or other operator can deploy a container into the patient's body cavity, capture and place the tissue specimen therein, and then mate the morcellator/cutter to the container for specimen cutting and removal. In another embodiment, the container and cutter are a single unit.

In another example, a third part consisting of a tissue grasper or tenaculum is built into a system that includes the cutter, which will be mated to the container or bag. Thus the cutter and the manipulator can be one assembly and the container can be a separate mating component. Alternatively, a third part consisting of a tissue grasper can be built into a system that includes both the cutter and the bag, and all three components exist as a single unit.

A four part system may consist of a tissue container, a tissue cutter, a tissue grasper and a tissue manipulator. In gynecology applications, a tissue manipulator typically is termed a uterine manipulator (such as the VCARE DX uterine manipulator sold by ConMed Corporation of Utica, N.Y.) and is often used to detach the uterus or specimen from the body. In gynecological applications of the present disclosure, a physician or other user employs a combination system such as a four part system by seating itself inside the vagina. First, a cuff of the uterine manipulator is seated around the patient's cervix and a manipulator arm is extended into the interior of the uterus prior to uterine detachment. Once the uterus is detached using means knows to those of skill in the art, the uterine manipulator is extracted and the cutter, tissue grasper and tissue container are introduced. The uterine manipulator and the tissue cutter can both share the same port on the device. The tissue specimen is then captured in the container, reduced in size through cutting, and removed from the body along with the tissue cutter, tissue grasper, and tissue container.

In general, the tissue container, tissue cutter, tissue grasper and tissue manipulator, as well as other components of systems described below, in their various configurations, may be made available in a variety of sizes so as to accommodate differences in patient size and anatomy.

A feature of embodiments disclosed herein include mechanisms and techniques by which the container can be maintained under tension or traction during use, in some cases constant tension, thus minimizing its size within the patient's body cavity. As will be described herein, this may be achieved by, e.g., simple pulling on the container by a physician or other operator during use, by way of a selftensioning mechanism, or by incorporation of a powered or non-powered crank, ratchet, rolling or other means.

Figure 2:
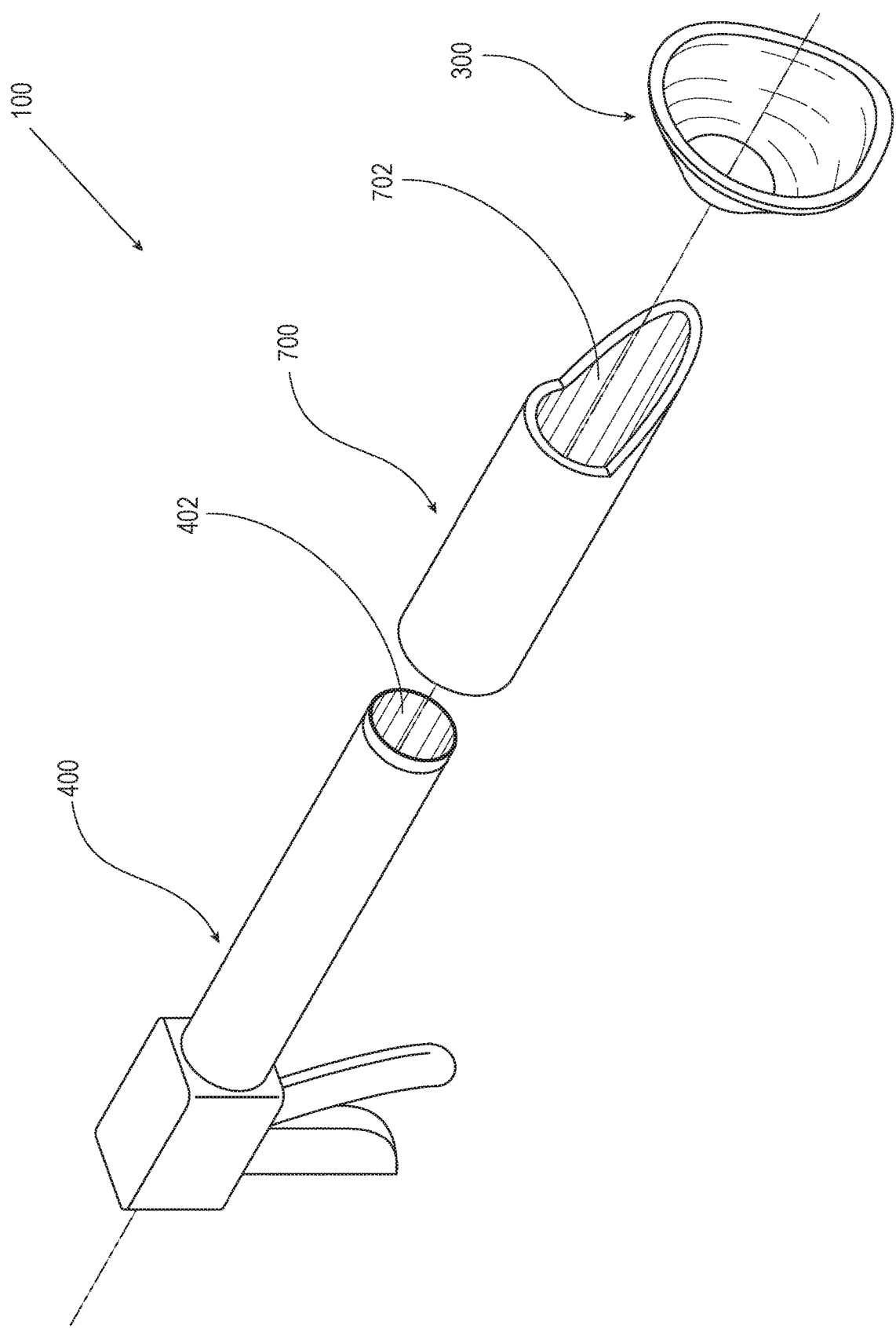
FIG. 2 is a perspective view of the components of the FIG. 1 system embodiment in exploded form.

FIGS. 1 and 2 depicts some components of a system 100 of tissue capture and removal according to an embodiment of the present disclosure. In the assembled FIG. 1 perspective view, guard 300, cutter or morcellation device 400 and cannula 700 are shown in working relationship to one another, while the exploded perspective view of those components in FIG. 2 affords a more detailed examination of each. For clarity, neither FIG. 1 nor FIG. 2 includes a tissue container 200 or a tissue grasper 500. Tissue grasper 500 may be deployed through a central lumen 402 of cutter 400. Tissue grasper 500 and/or cannula 700 may be omitted from systems of the present disclosure, such that in some embodiments system 100 consists of a cutter 400, a guard 300 (and/or protective feature that may be integrated with one or more components described herein), and a container or bag 200. In other embodiments, system 100 may include a cutter or morcellator 400 and a container 200. The example system 100 of FIGS. 1 and 2 includes both a guard 300 and a protective feature in the form of extension 776 on cannula; one or both of these features may be included in various embodiments of systems of the present disclosure.

As will be more fully described below, system 100 may be used for the safe and efficient access to, capture, and removal of tissue from a human or other mammalian body. Embodiments of system 100 and other instruments, such as standard laparoscopic and robotic instruments, gas injectors for insufflation, and visualization tools such as cameras, etc., as described herein may be used in particular in connection with minimally invasive procedures, such as those undertaken laparoscopically, where the tissue specimen of interest to be removed is relatively large compared to the size of the port. The port, sometimes referred to herein as a "body port" or "opening" may be a surgically created incision, including without limitation various pelvic or abdominal incisions (such as umbilical, periumbilical, left and/or right lower quadrant, left upper quadrant, etc.), appliances or devices that may be installed in a body, such as subcutaneously, including as dermal ports, venous ports, arterial ports and the like trocars, and incisions from prior surgeries or procedures. The port or body port may also be a natural body opening (e.g., vagina, rectum, esophagus, nostrils/nasal canal, bronchial tubes, auditory canal, etc.) through which the specimen 20 is to be removed. Embodiments of the systems 100 of the present disclosure and various components discussed herein can be used in connection with any of these surgically-created or natural ports or via any combination of two or more of such ports.

The components discussed herein, including those of system 100 as shown in FIGS. 1 and 2, may be sized and constructed of materials appropriate to the location of the tissue specimen 20, the indication, the particular port or opening through which the specimen is to be removed, patient size, etc.

System 100 may include a cannula 700 having a central lumen 702702 through which may be disposed a tissue grasper or forceps, (e.g., a tenaculum) or similar instrument 500 for the manipulation of tissue; particularly tissue specimen 20, to be removed. Typically, but not always, cannula 700 if used is deployed through a tissue enclosure/container or bag 200 that has previously been deployed through a body lumen or port as described in detail below. A cutter or morcellation device 400 may be disposed through cannula central lumen 702 for the processing of tissue specimen 20 as shown in the system 100 embodiment of FIGS. 1 and 2. An optional spacer (not shown) may be disposed in or be an integral part of cutter central lumen 402 aids in keeping or serves to keep grasper 500 centered within lumen 402. A guard 300 may be employed to protect container 200 from damage as the tissue specimen 200 is processed by cutter 400 and protect tissue not intended for removal (e.g., bowels, bladder or other tissues depending on the location of treatment). Guard 300 may be a cone-shaped component as shown in FIGS. 1-2 or may take on another shape as will be described below. Guard 300 and/or its function may be attached to or even integrated with other components of systems described herein, including, e.g., cutter 400, grasper 500, cannula 700, or combinations thereof.

Figure 3A:
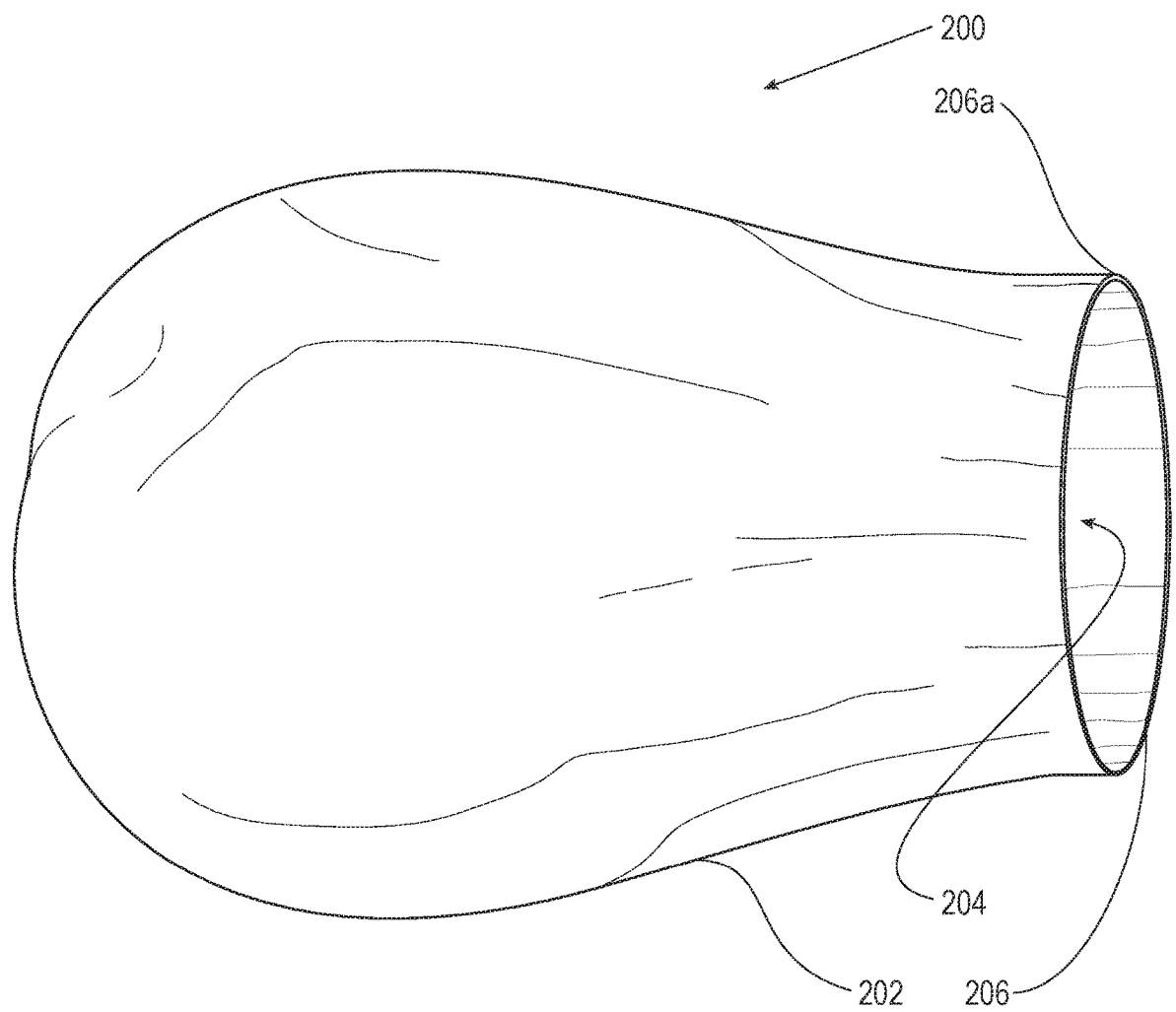
FIG. 3A is a partial perspective section view of an embodiment of a tissue container.
Figure 3B:
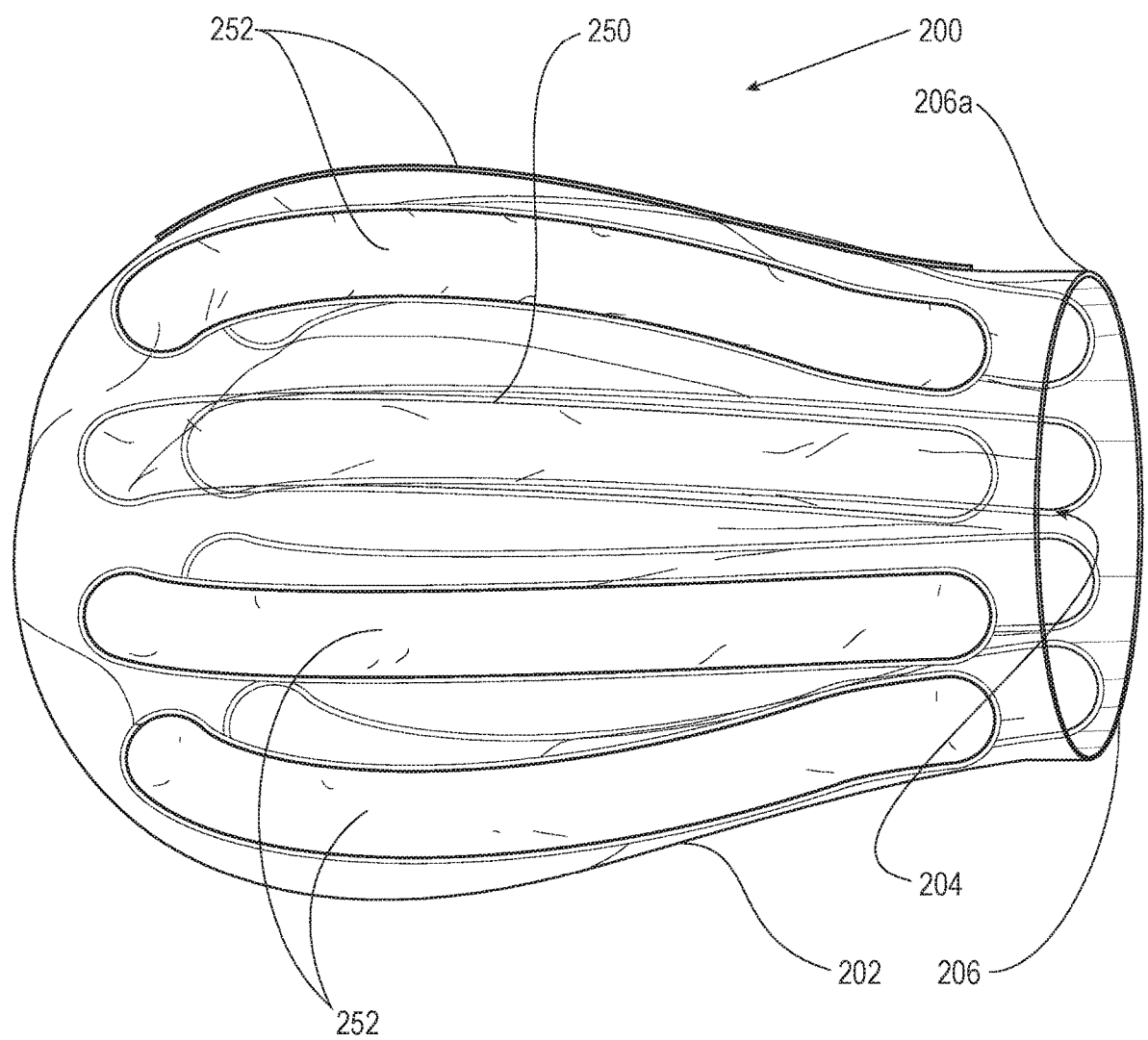
FIG. 3B is a partial perspective section view of an embodiment of a tissue container including stiffening or reinforcing members.

FIGS. 3A-B illustrate two embodiments of an enclosure apparatus, or tissue container 200, according to the present disclosure. In general, the primary function of tissue container or bag 200 is safely to contain one or more tissue specimens or samples 20 during the procedure or method of use for the systems described herein. Container 200 may be more rigid or stiff, or less rigid or stiff (akin to that of a bag); thus, the terms "container", "enclosure" and "bag" are used interchangeably herein to encompass all embodiments useful to achieve the purposes of this disclosure. Such terms therefore encompass flexible or deformable bags, semi-rigid bags or containers, rigid or non-deformable containers, containers having both relatively rigid and relatively flexible components or aspects, and the like. Bag 200 may take on any shape and size suitable for the indication for which it is designed. For instance, enclosure 200 may take on a generally cylindrical, spherical, spheroidal (e.g., prolate spheroid), prismatic, pyramidal, cuboid, cubical, conical, irregular (e.g., pear, squash, etc.) or otherwise asymmetrical shape or a hybrid of two or more of these fundamental shapes. If used in a gynecological procedure where the uterus and/or other organs are to be placed therein, tissue container 200 may be in a generally spherical shape and have diameters ranging from between about 50.0 mm or less by about 400 mm or greater. Container 200 may also be in a generally spherocylindrical shape (i.e., pill capsule) or a semi- or hemi-spherocylindrical shape with an opening diameter of between about 50.0 mm or less to about 400 mm or greater, such that a tissue specimen (e.g., uterus) having its greatest dimension on the order of generally about 20.0 cm to about 30.0 cm or larger may be placed and stored therein. A hemi-spherocylindrical shape may be useful in systems where the bag opening 206 is large. If the container 200 is measured in terms of three dimensions, container 200 may take on sizes ranging from about 300 mm by 300 mm by 400 mm. For other indications, such as the capture and retrieval of a stomach mass via the esophagus, bag 200 may take on any of the aforementioned shapes and have a size ranging from those useful in removing a uterus or smaller.

Bag 200 includes an outer surface 202, an interior volume 204, and at least one opening or aperture 206 defined by one or more edges such as edge 206a shown in FIGS. 3A-B. In one embodiment, bag 200 is impermeable to cancer cells, yet is thin and flexible enough so that it may be rolled, folded or otherwise compacted so that it may be transported through a small port, hole, lumen or other aperture, typically on the order of about 5.0 mm or smaller to about 25.0 mm or greater in diameter. Bag 200 can also be made to withstand tears, punctures, impacts and generally undesirable interactions with surgical instruments, tools (including, e.g., robotic and/or laparoscopic tools) and other components of system 100 (including, e.g., cutter 400 and its blade 408), etc. In this way, container 200 can operate to maintain its structural and functional integrity to safely keep one or more tissue samples 20 placed within it properly isolated from the environment outside the bag, such as may exist in an abdominal or pelvic cavity before container 200 containing specimen is removed from the patient's body. This is particularly useful in designs where the tissue specimen 20 placed in the container 200 contains cancerous or pre-cancerous cells or is suspected of containing cancerous or pre-cancerous cells.

Tissue container 200 may be made of any suitable biocompatible material, including plastics such as polyethylene, polyurethane, polypropylene, PET, PETG, aramid and para-aramids, including, e.g., poly-paraphenylene terepthalamide (KEVLAR), aliphatic or semi-aromatic polyamides (NYLON), rubber, thermoplastics and others. It may be of a composite construction, including a bi-layer construction as shown in the example embodiment of FIG. 4. Such composite embodiments may be made from, e.g., two sheets of material that are folded flat, as multiple sheets and formed into a three-dimensional bag shape, or can, e.g., be manufactured in a three-dimensional fashion by use of a molding or special tool and/or by way of blow molding, compression molding, or three-dimensional printing techniques. Constructing bag 200 from different materials may pose advantages from durability, toughness, usability, cost, manufacturing, marketing or other perspectives. For instance, bag 200 may be made of a visually transparent or opaque plastic layer or layers so to allow a physician or surgeon to visualize tissue specimens as they are placed and/or after they have been placed into bag 200 and to allow visualization through the container to see tissue on the other side. This is particularly useful when using fiber optic or other camera or video equipment during a procedure. One embodiment of a composite container 200 can be created through the construction of multiple layers of plastic and mesh. In the bilayer container embodiment depicted in FIG. 4, each layer can serve different or overlapping purposes: one layer, such as an outer layer 232, can create a watertight seal for the contents of the bag while another layer, such as an inner layer 230, can protect the container from the morcellator blade. Both layers together, for example, combine to provide the desired toughness, puncture- and tear resistance, etc. properties as discussed herein. Inner layer 230 can be made out of a durable plastic such as those in the aramid and para-aramid classes, including, e.g., poly-paraphenylene terepthalamide, or can be made of or incorporate a metal mesh to protect the container from the blade.

Bag 200 may be doped by known techniques to render it, e.g., radiopaque for optimal utility in certain applications, it may contain wires, filaments, or other materials to cause the bag to change shape, radiate electromagnetic signals, thermally activate, or chemically transform as desired. It may also come pre-treated with one or more agents to affect the tissue specimen if desired, such as a preservative agent, contrast agent, etc., and/or may be coated with one or more layers of hydrophilic or hydrophobic materials and/or other lubricating materials or otherwise treated to provide a low-friction environment for the bag interior 204 with which tissue specimen 20 will be in contact. Such coatings or layers may be discrete and applied during manufacturing in sequential fashion (e.g., three-dimensional printing, other known deposition techniques) or may be in a composite or alloy-like form during manufacturing and/or as-fabricated. Having a low-friction and/or lubricious surface, particularly in bag interior 204 can facilitate methods of tissue cutting and removal according to embodiments described herein, as tensioning of container 200 tends to bring tissue specimen 20 within close proximity of or in direct contact with container interior 204 and the cutting process may benefit as the specimen 20 can spin or otherwise move relatively easily against the interior surface of bag 200. A "peeling" process in particular as a way of cutting tissue 200 may benefit from such a container configuration under the methods described herein. Container 200 may in some embodiments contain markings such as gradations or a grid pattern (such as employed on the PNEUMOLINER containment device sold by Olympus America, Inc. of Southborough, Mass.) to aid the physician in locating and assessing the size of tissue samples placed therein, ascertaining whether the container 200 is folded or crimped in some way, how much of the container is left inside the body as it is being removed by, e.g., rolling edge 206a when applying tension on container, etc. Such markings may be present using cartesian coordinates, radial coordinates, or spherical coordinates depending on the shape, configuration and contemplated use or uses for container 200.

As will be described below in detail with respect to several embodiments of the present disclosure, container 200 can have a tether, drawstring, or other component affixed thereto or integrated therewith such that a physician or other user may manipulate the bag during use, facilitating its placement, opening, closing, and removal from the body. In one embodiment, one or more tethers extend(s) from the container 200 in the vicinity of opening 206, and attached, integrated or otherwise affixed on or near container edge 206a. Such tethers may be stiff, particularly with respect to their column stiffness, or they may be more flexible. The use of a tether or similar component is useful in procedures where the enclosure 200 has been deployed into the body cavity 30 of interest for placement of a tissue specimen 20 into the bag's interior 204, and the tether or tethers extend(s) out of the body cavity 30 through the access port 22 or natural opening (e.g., vagina, esophagus, etc.) and held, affixed or tied to a separate instrument and/or simply monitored so that at the appropriate time during the procedure the physician or other user may pull on the tether or tethers to safely and effectively remove the bag from the patient's body through opening 22. Tethers may also be utilized to aid a physician, either manually or via the use of automated equipment, in applying and/or maintaining tension on enclosure 200 during the tissue capture and removal process.

One embodiment of container 200 includes one or more stiffeners or reinforcement members 252, each of which can be initially separate from container 200, as shown in FIG. 3B. Features such as stiffeners 252 allow container 200 to assume and maintain a desired shape or volume at the appropriate time to aid in the tissue capture and removal process and can also help to prevent the cutter 400, including blade 408, from damaging container 200. Any number of stiffeners of identical or varying dimensions, shapes and materials may be used. For instance, between 1 and 4, between 2 and 8, between 4 and 16 or more stiffeners may be used. Any medical grade material having the appropriate mechanical properties may be used for stiffeners 252, such as spring steel, certain plastics, nickel titanium alloys, etc. Each stiffener could be a composite material; for instance, a bilayer construction that imparts preferential stiffness under bending forces for one direction compared to another may be useful. Certain embodiments of stiffener 252 may be shape-set using techniques known to those of skill in the art to undergo strain- or temperature-induced transformations during manufacturing, packaging and/or use to optimize performance. A given stiffener may have a thickness ranging from about 0.1 mm to about 4.0 or more mm, and may have a longitudinal dimension (when shaped as shown in FIG. 3B) of between about 1.0 cm and about 20 cm or longer, and widths ranging from about 1.0 mm to about 30 mm or more. Stiffeners 252 can be arranged symmetrically to facilitate the desired performance of the enclosure 200 or, in certain situations, may be configured to be arranged with an asymmetric distribution or pattern to coax container 200 to take on a particular shape when open and/or to force or at least facilitate certain sequential motions of the container 200 during use, including opening the container, closing the container, fastening the container, tensioning the container and removing the container from the patient's body.

One or more pockets 250 on or in container 200 may be present to guide the insertion of and house the stiffeners 252, either partially or completely, therein. Stiffeners 252 may be inserted during the tissue capture and removal procedure by the physician or other user (e.g., after container has been deployed into the pelvic cavity 30) or they may be manufactured as an integral part of or attached to tissue container 200. Stiffeners 252 may be sized and have the flexibility to allow the bag to be rolled into a small dimension for insertion through a surgical port or natural body opening 22. In other embodiments, stiffeners 252 could be directed through one or more loops or other fastening mechanisms that keep the stiffeners 252 between a morcellation blade 408 and container 200.

Figure 5A:
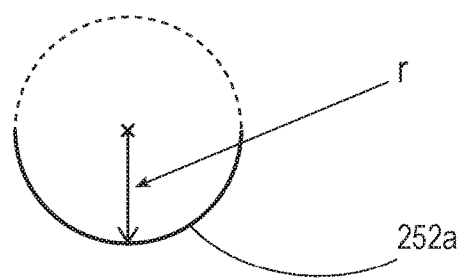
FIGS. 5A-C are various views of an embodiment of a tissue container including bi-stable spring stiffening or reinforcing members.
Figure 5B:
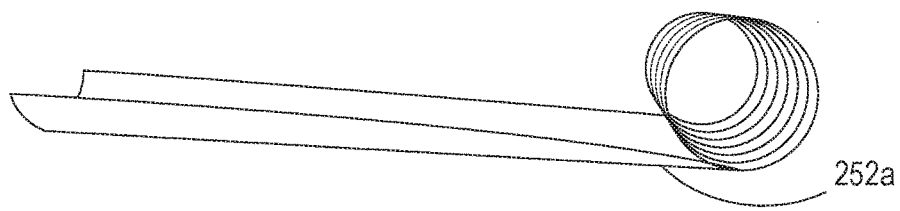
Figure 5C:
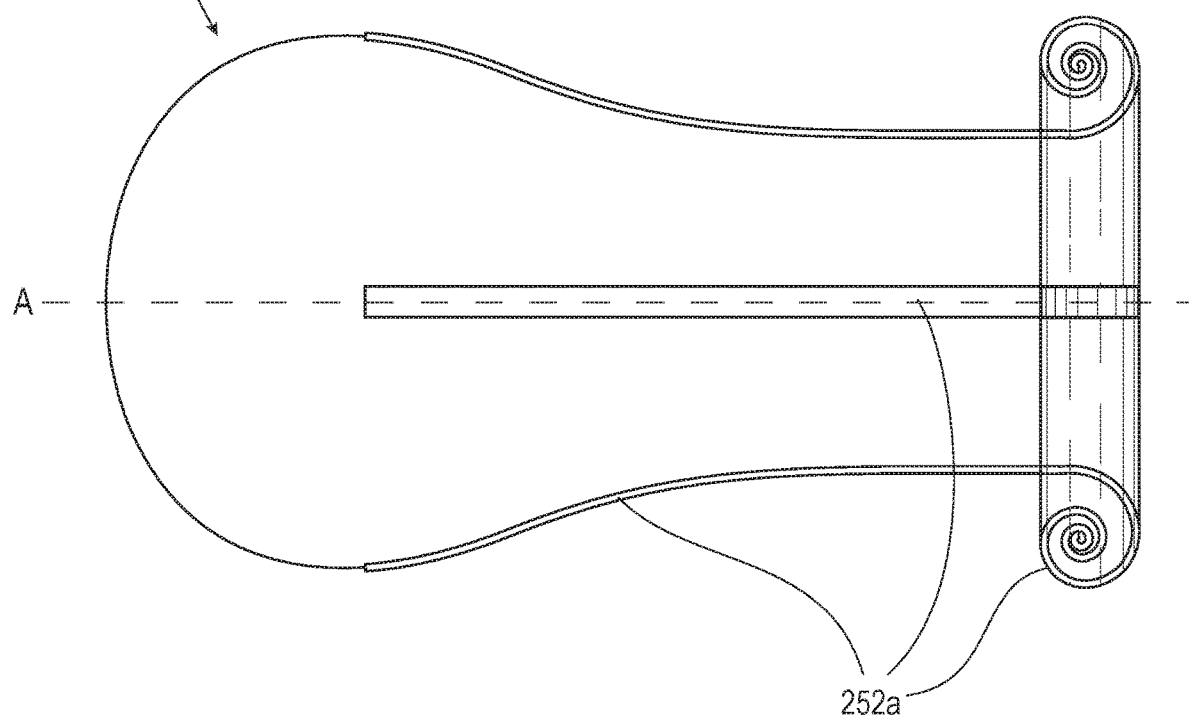

FIGS. 5A-C show another embodiment in which the stiffener 252a can take on a curved cross-sectional profile such as a 'U' shape (FIG. 5A), 'J' shape, "V" shape, etc. to provide stiffness or resistance in one direction, in this case for example when container 200 is encroaching on blade 408, but flexibility in the other direction, which may be needed for rolling container 200 up. In the embodiment shown in FIGS. 5A-C, stiffening member 252a takes on a curved profile with a radius of curvature R that may be chosen to optimize its radial stiffness and resistance to lateral bending or rolling up against the radius while being relatively flexible in the opposite direction. FIG. 5B shows a stiffening member 252a of this type rolled up in that opposite direction. This type of stiffener 252a is similar to a bi-stable spring. FIG. 5C shows an embodiment of container 200 that can be rolled up or collapsed in an orderly fashion along a longitudinal central axis of the container in the direction of arrow A in connection with one or more stiffeners 252a.

Figure 4:
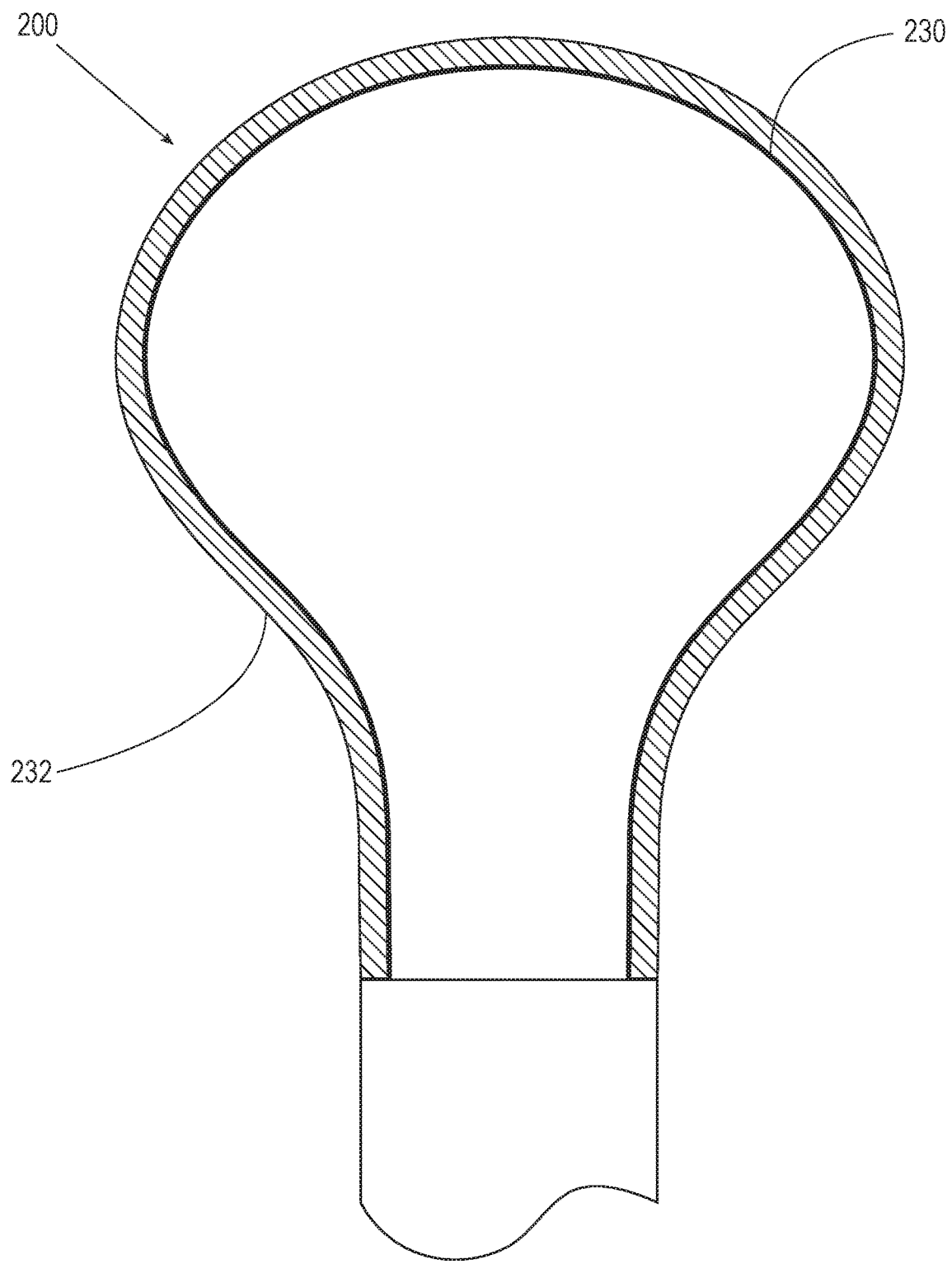
FIG. 4 is a cross-sectional schematic of a composite tissue container incorporating a bi-layer construction.

In some embodiments and methods, such as, e.g., the method disclosed in connection with FIGS. 23, 24 and 25 and container 200 embodiments of, e.g., FIGS. 3, 4 and 5, container 200 can be designed intentionally to remain open such that opening 206 and attendant edge 206a are disposed outside the patient's body—through opening or port 22 (e.g., surgical port) or natural opening (e.g., vagina 32 and vaginal opening 34). Hence, for the tissue specimen 20 cutting or morcellation step, cutter 400 may be inserted into bag interior 204 through container opening 206 as it is disposed outside body opening 22. Such embodiments and methods therefore do not require that container 200 be closed during the procedure, as specimen 20 is cut/morcellated within bag interior 204 while the opening is under the physician or other operator's control outside body opening 22 so to prevent tissue specimen 20 and other tissue and/or bodily fluids from being in contact with the patient's body during the cutting/morcellation step.

In other methods contemplated herein, however, systems of the present disclosure include components that may be used to deploy container 200 in the body cavity, capture the tissue specimen 20 therewithin, closing an opening 206 of container 206 to enclose the tissue specimen 20 and other tissues and/or bodily fluids within container interior 204, and then morcellating or cutting the specimen 20 within container interior 204. In such methods and embodiments, cutter 400 has been inserted by the physician or other operator into container interior as part of the methods described herein, or cutter 400 may be assembled or manufactured into or is part of a separate container opening 206 as will be described in greater detail below. In addition to cutter 400, other components together with cutter, singly or in combination, such as guard 300, grasper or tenaculum 500 and/or cannula 700 (or cannula-guard embodiments 740, 770) may be used via such a separate container opening for such multi-opening container embodiments. Such other components, singly or in combination, may be made integral to the container 200, with or without cutter 400, to form an "all in one" type of system 100, or may be separate components introduced by the physician or other user into container 200 via this separate opening to accomplish the methods disclosed herein.

It is understood and within the scope of the present disclosure, therefore, that various container embodiments can have only one opening (e.g., container embodiments of FIGS. 3, 4 and 5) or can have two or more openings. In embodiments of container 200 having more than one opening, one or more first openings 206 may be designed to be closed by a physician or other user (via, e.g., any number of mechanisms 210 such as, e.g., a zipper 212, drawstring 218, etc.), to enclose tissue specimen 20 that has been placed within container interior 204, and a separate additional opening 206 may be present through which cutter 400 and/or any number of additional components may be introduced or preassembled as described above. Reference numeral "206" is used herein to refer to any of such container openings, thus allowing it to be understood from the context of the description for a particular container embodiment or method of use as to which type of opening or openings of container is being discussed.

FIGS. 6-14 depict embodiments of container 200 that, as with other embodiments, include elements or features useful in permitting the bag 200 to play an effective role in securely capturing and removing tissue in connection with the systems of the present disclosure. All of the features and designs for enclosure 200 as described herein, and in particular those described in FIGS. 3-14, may be utilized singly or in any combination to suit the performance requirements of the present disclosure. As such, the depiction of a particular embodiment is not meant to be limiting but rather to show possible features and elements associated with and included in this disclosure.

Figure 6A:
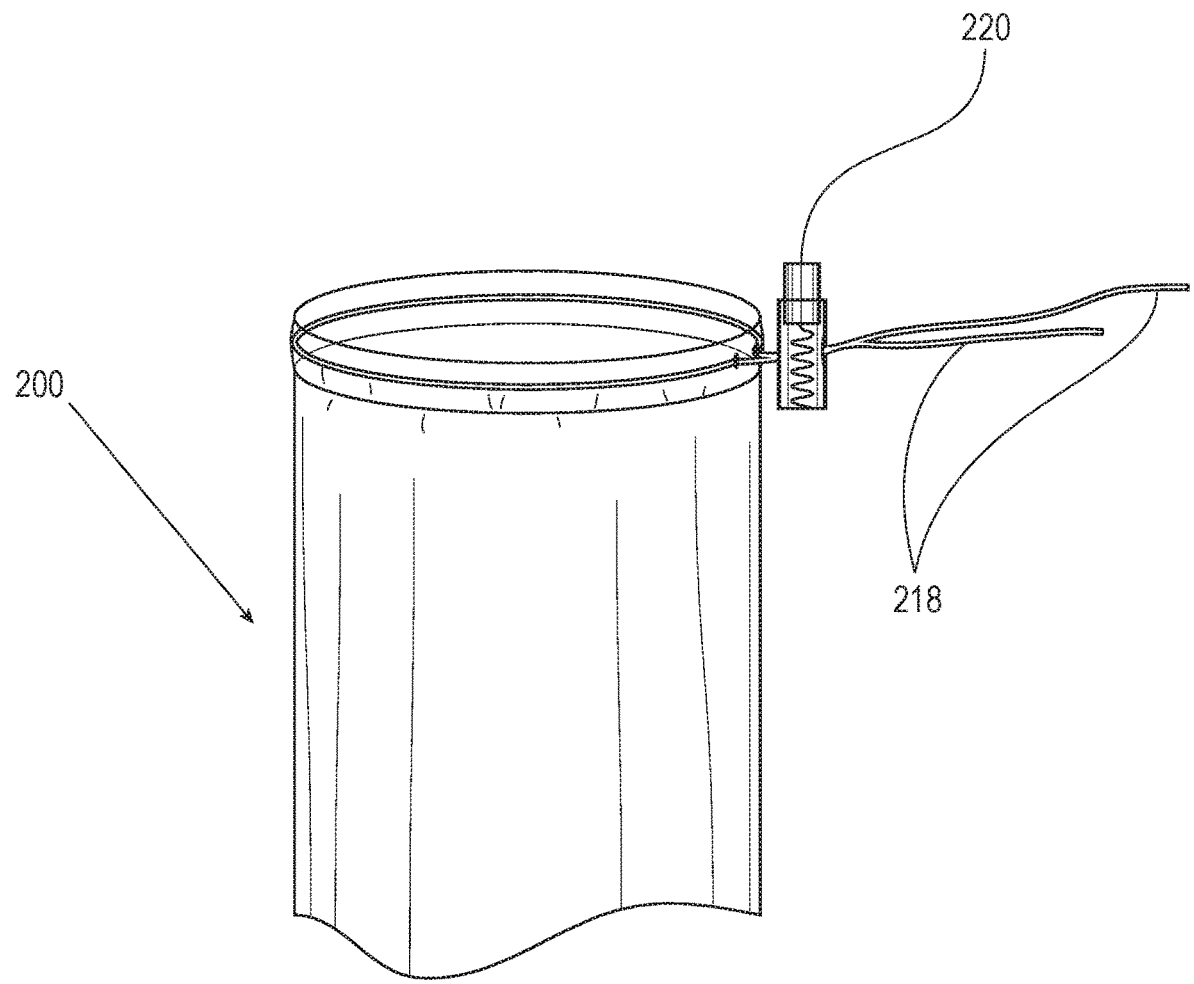
FIGS. 6A-C are partial perspective views of two embodiments of a tissue container closure mechanism.
Figure 6B:
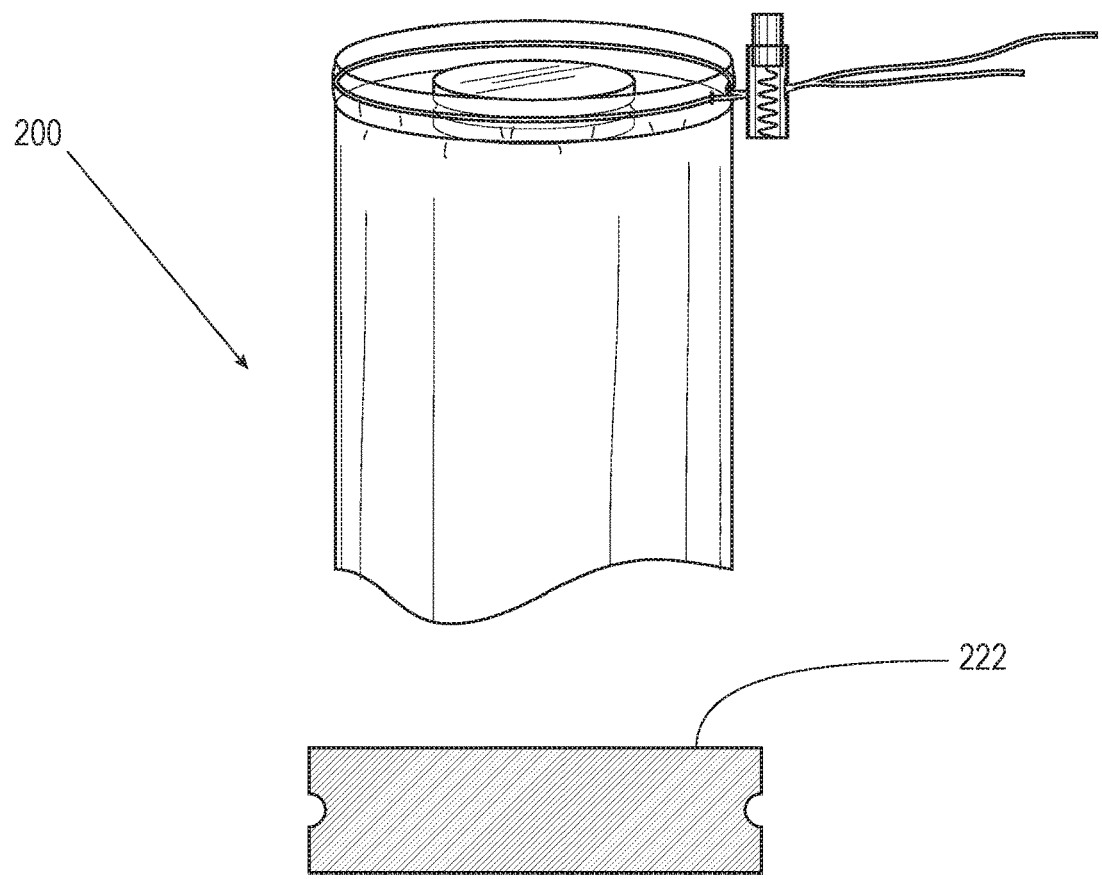
Figure 6C:
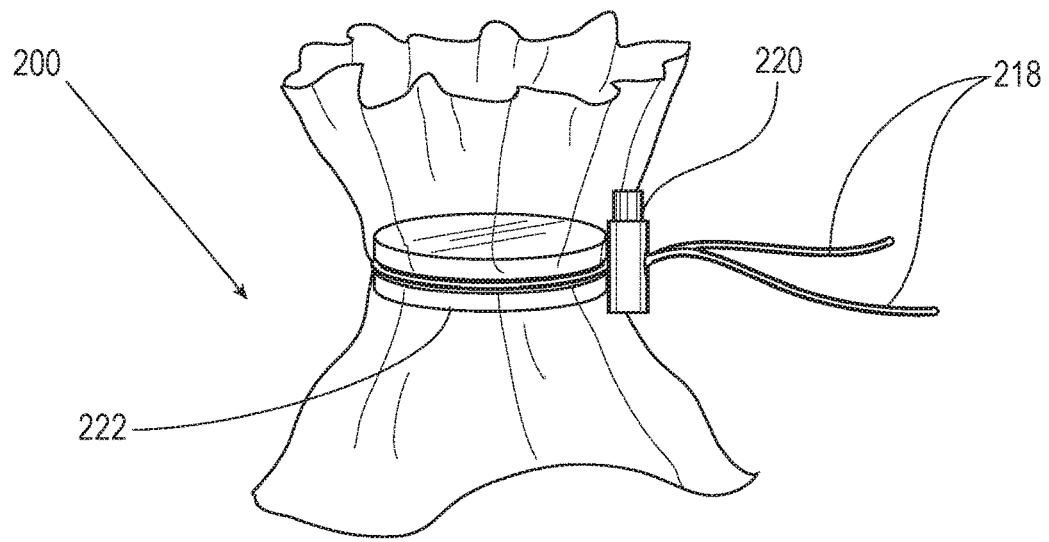
Figure 7A:
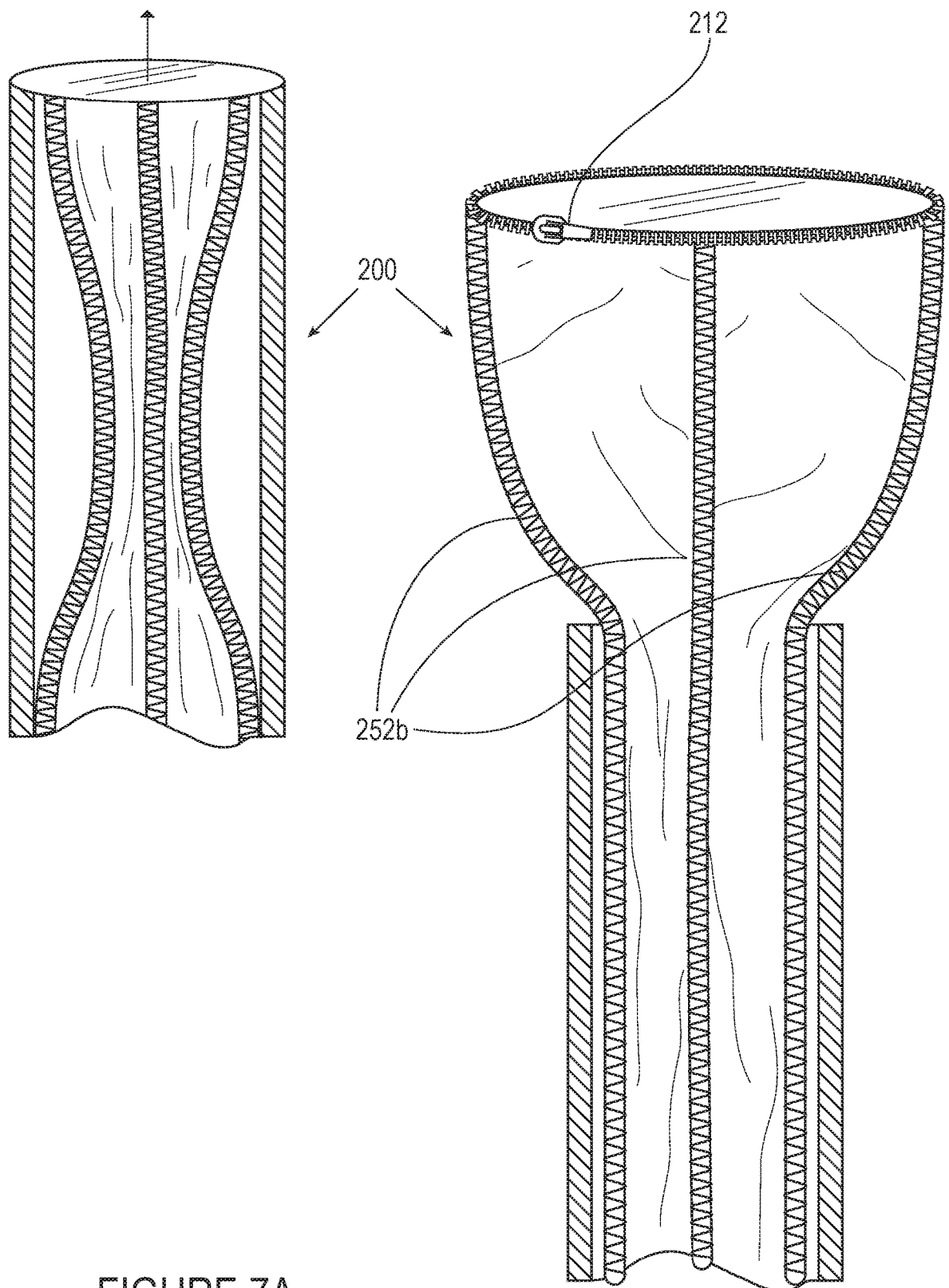
FIGS. 7A-B are various views of embodiments of a tissue container incorporating expandable spring mechanisms or features.
Figure 7B:
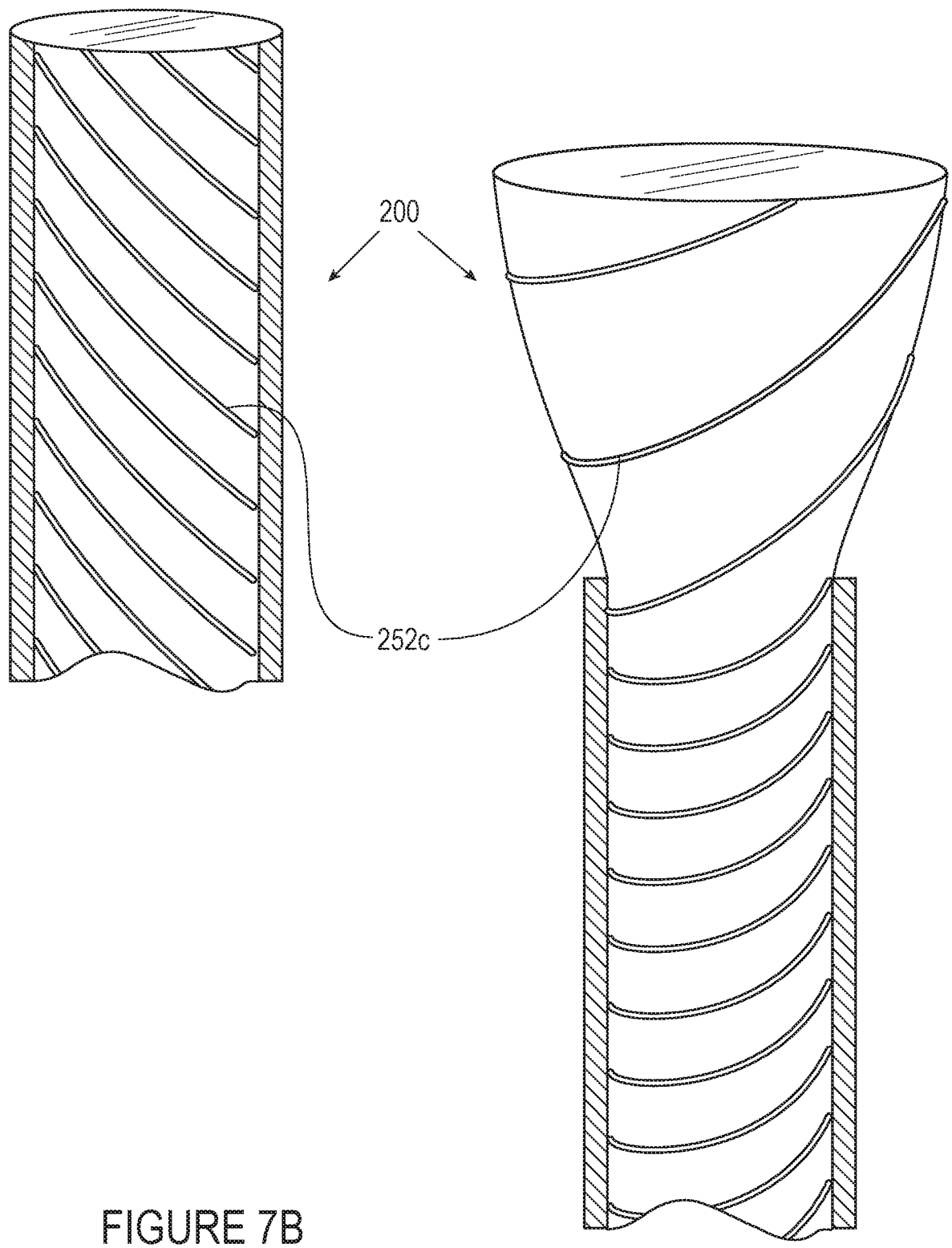

FIGS. 6A-C depict an embodiment of enclosure 200 having features that provide mechanisms for closing bag opening 206. During methods of using the system embodiments of the present disclosure, once a tissue specimen 20 has been placed into the container interior 204, it is desirable to remove the specimen from the patient's body in a way that minimizes the risk that the specimen (and attendant bodily fluids or other tissue) makes unwanted contact with the patient's body tissue and/or bodily fluids, during cutting or morcellation, particularly if it is suspected that cancer or pre-cancerous cells may be present in container 200. FIGS. 7A-B depict additional embodiments of container 200 including features designed to aid container 200 in opening to a configuration that facilitates the placement of a tissue specimen 20 into the bag interior 204 and allow container 200 to move into and maintain a specific three-dimensional configuration or shape. FIG. 7A shows a container 200 in which a spring consisting of reinforcing members 252, here in the form of straight members 252b that extend radially outward relative to a central longitudinal axis of container 200 once removed by the constraint imposed by, e.g., the body port or opening 22 or introducing sheath or cannula 650. Alternatively, the FIG. 7B embodiment includes a reinforcing member 252 in the form of a helically-shaped expansion spring 252c that is curved such that container 200 expansion once unconstrained is comparatively linear, e.g., along the spring's virtual/expansion axis, which such axis can generally be aligned with the central longitudinal axis of container 200. Once the target tissue 20 is within the bag interior 204, the container of FIGS. 7A and 7B can be closed via any suitable closing mechanism. The rigid or spring loaded container embodiment of FIG. 7B affords container 200 additional protection to help prevent container 200 from making contact with the morcellator blade 408 during the morcellation phase. Spring 252c also helps give container 200 a more open shape which facilitates placement of tissue such as specimen 20 therein.

FIGS. 8A-C are directed to a two-part container 200 embodiment in which a first container component 270 may be connected to a second container component 272 in order to securely close opening 206 and keep the contents, such as tissue 20, within the container interior 204. First and second components 270, 272 may be mated/secured to one another in any number of ways, including but not limited to radial loading until a spring engages a lock, or the container can be attached through a threaded or quarter turn screw mechanism. FIG. 8A shows an embodiment of enclosure 200 in a loading position in which first component 270 is folded into a configuration for delivery through a surgical or natural port and a portion of second component 272 is compressed into a frustum shape. In FIG. 8B, both components 270, 272 self-expand or are expanded by manipulation to a larger size. Ideally, a tissue specimen 20 is then placed into the second component 272 after container opening 206 has expanded. Expansion of components 270, 272 may be accomplished by any number of suitable mechanisms, such as by the inclusion of flexible elements within the components or attached to components 270, 272 that cause them to expand (e.g., spring steel or NiTi filaments or parts) or as homogeneous construction in which the material comprising components 270, 272 themselves gives them an inherent ability to expand from a collapsed configuration. Then, as shown in FIG. 8C, first and second components may be securely coupled; in this example by a counterclockwise twisting motion of first component 270 relative to second component 272 as shown by the arrows such that interlocking threads or similar mechanisms engage and effect coupling of the two components. Coupling of first and second components 270, 272 may also be accomplished by the use of tabs, hook and loop closures, zippers, magnets, tongue and groove seals, or any combination thereof to form a secure and ideally fluid-tight connection. During use, second component 272 could be inserted through a surgical or natural port, or it can be designed as part of the morcellation device 400.

Figure 9D:
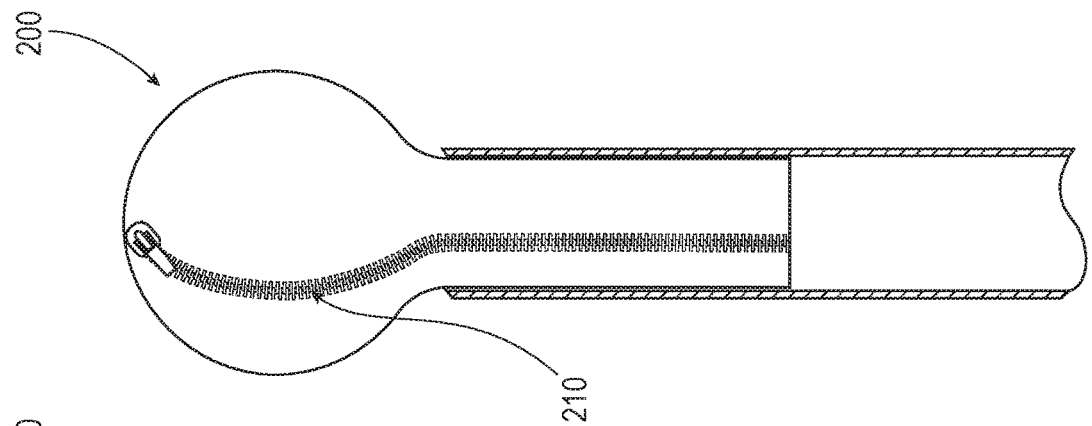
FIGS. 9A-D depict the operation of a tissue container configured to encircle a tissue specimen.
Figure 9C:
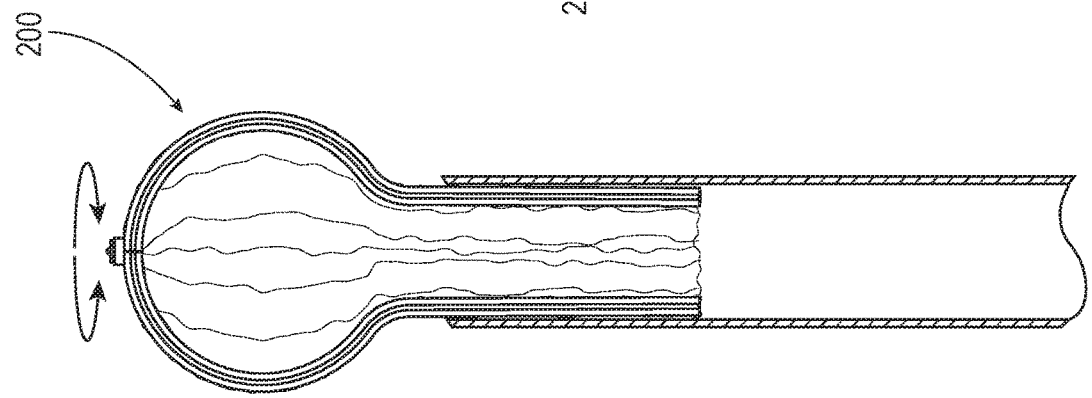
Figure 9B:
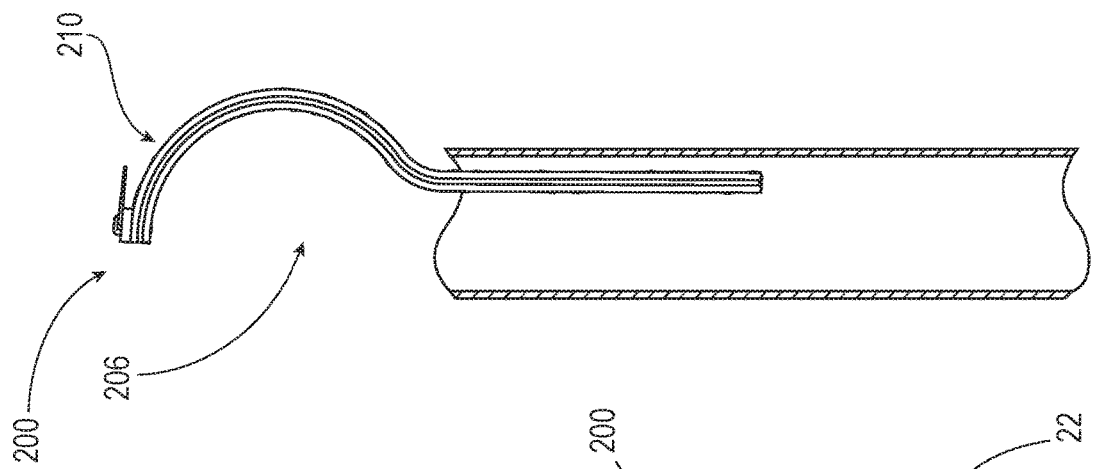
Figure 9A:
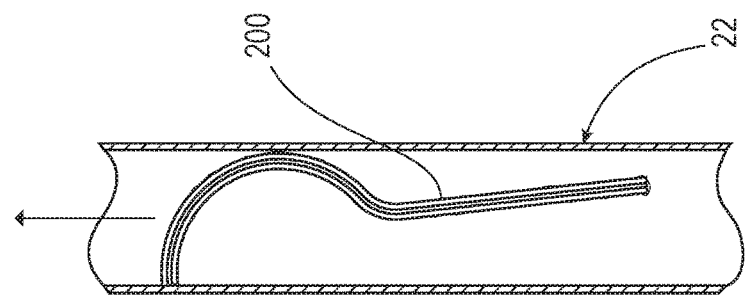

In another embodiment, container 200 is created through a smaller package which can encircle the specimen as shown as it sequentially unfolds. FIGS. 9A-D depict an embodiment of container 200 that takes on a spherical or semi-spherical shape, not unlike that of a lightbulb or plant bulb, when deployed. In this embodiment, enclosure 200 may take on a relatively straight configuration when collapsed for delivery through, e.g., a surgical or natural body port 22 in connection with the present disclosure. This is depicted in FIG. 9A. Once a distal portion 255 of container 200 extends as shown in FIG. 9B beyond a distal end of a surgical or natural body port, one or more wires (not shown) in proximity to the container opening 206 can be manipulated radially to open distal portion 255 of container and create an interior 204 into which a tissue specimen 20 may be placed. The material of container 200 may be made of a flexible but durable material or materials as described elsewhere herein so that when the wire or wires are moved as described, the lightbulb shape of container 200 forms as the specimen 20 is captured within its interior 204. Complete motion of the wire or wires around a full 360 degree or approximate 360 degree path (as shown in FIG. 9C) will allow the edge 206a of container 200 to mate with itself as seen in FIG. 9C. At this point an operator may use any number of closure mechanisms or features 210, such as a zipper 212, to close container 200 such that the tissue sample 20 and other contents are secured therein. Any suitable mechanism, such as a pusher rod or other closure member, may be used to close zipper 212. FIG. 9D shows this embodiment of container in the expanded and closed configuration. Another embodiment of container 200 contemplates zipper 212 moving the opposite direction to close container opening 200, effectively entrapping tissue specimen 200 in container interior 204. A cam mechanism may also be used to rotate the two spring/wire forming shapes between about 1 and about 360 degrees.

Other embodiments of container (not shown) include an accordion-shaped bag 200 that may be unfurled up to about 360 degrees once in the body cavity 30 and around tissue specimen 20, thus capturing it.

Figure 10A:
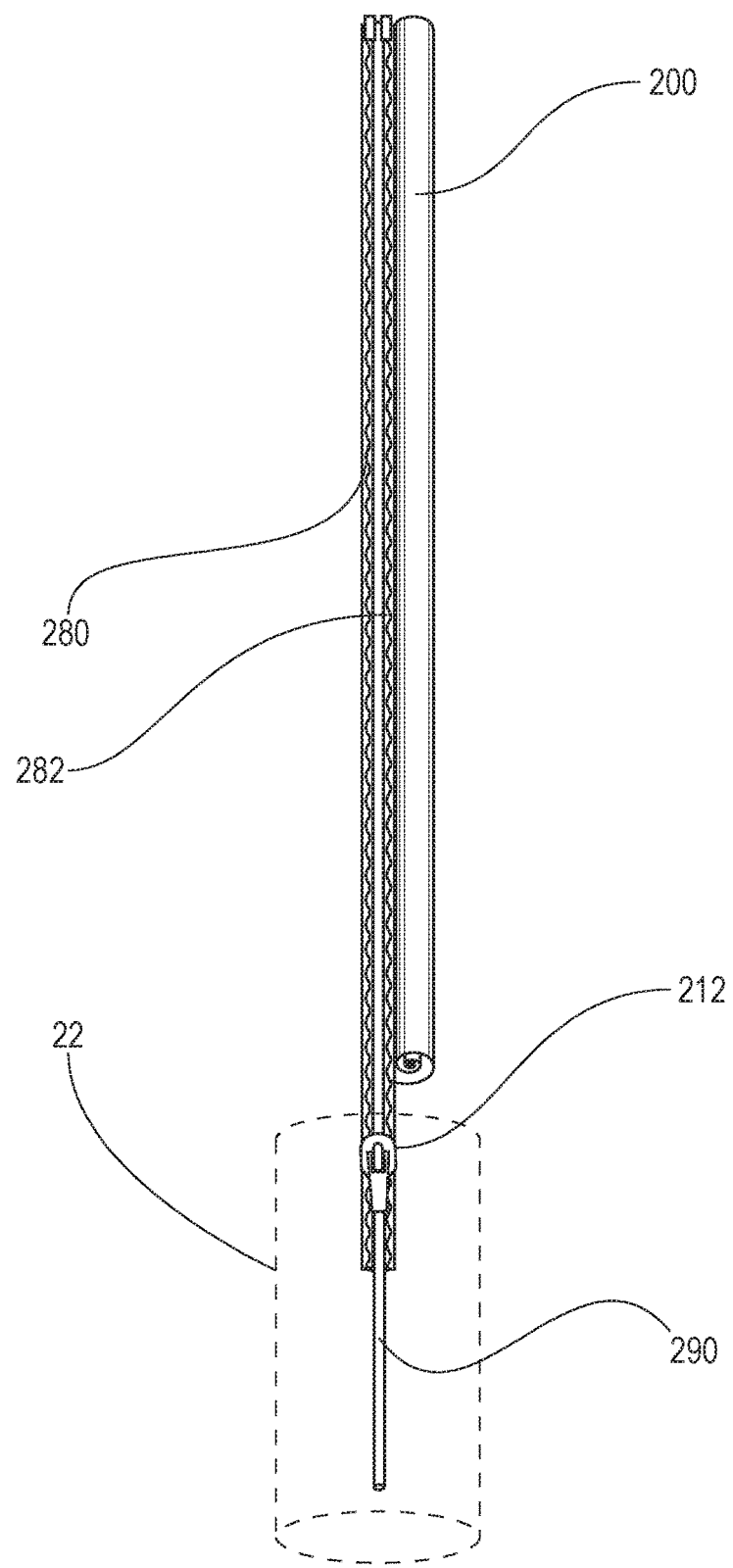
FIGS. 10A-C depict the operation of a tissue container that in use may initially be collapsed, presented through a cannula or port, used to capture a specimen via a circular opening and then closed automatically through the same cannula or port.
Figure 10B:
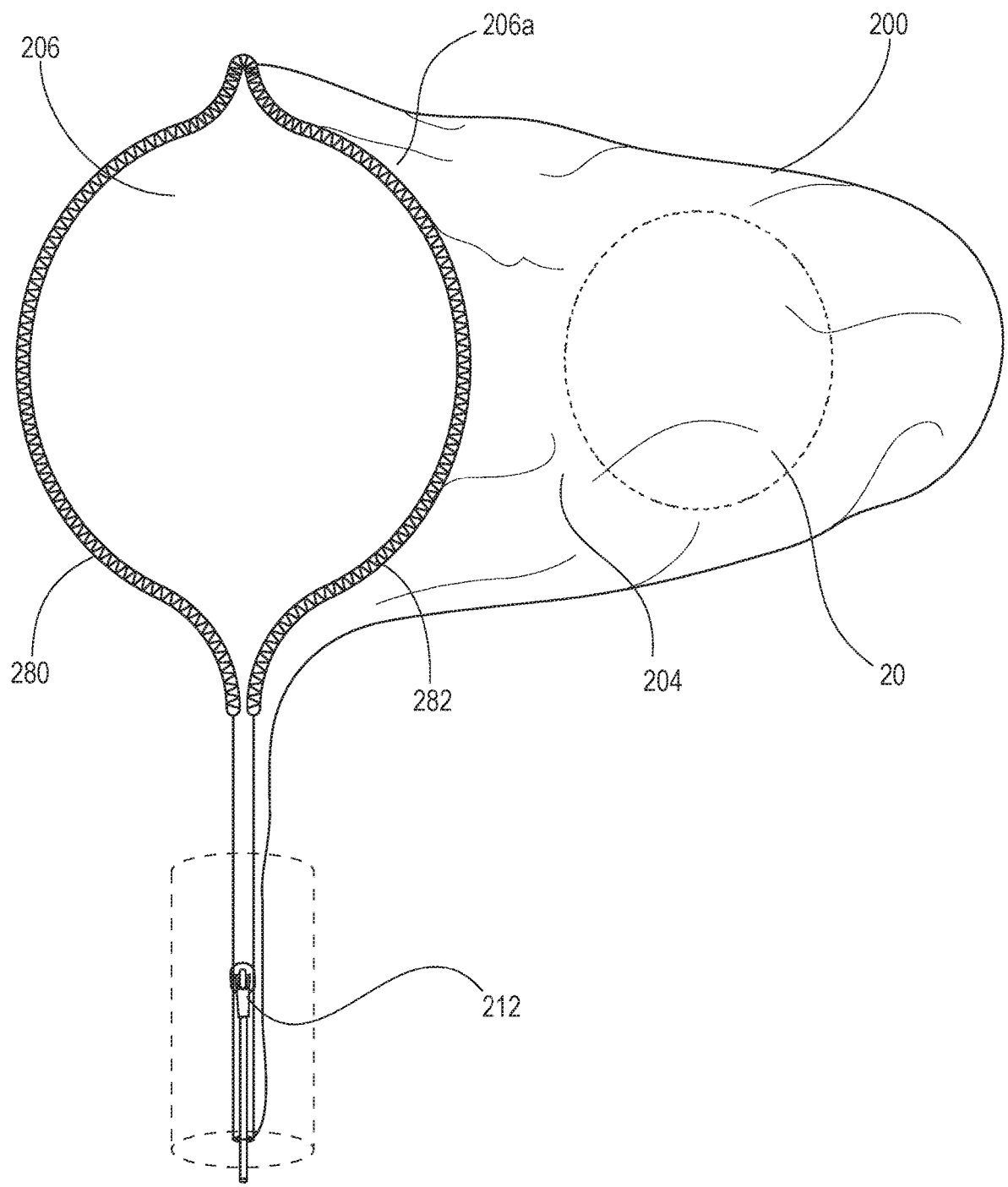
Figure 10C:
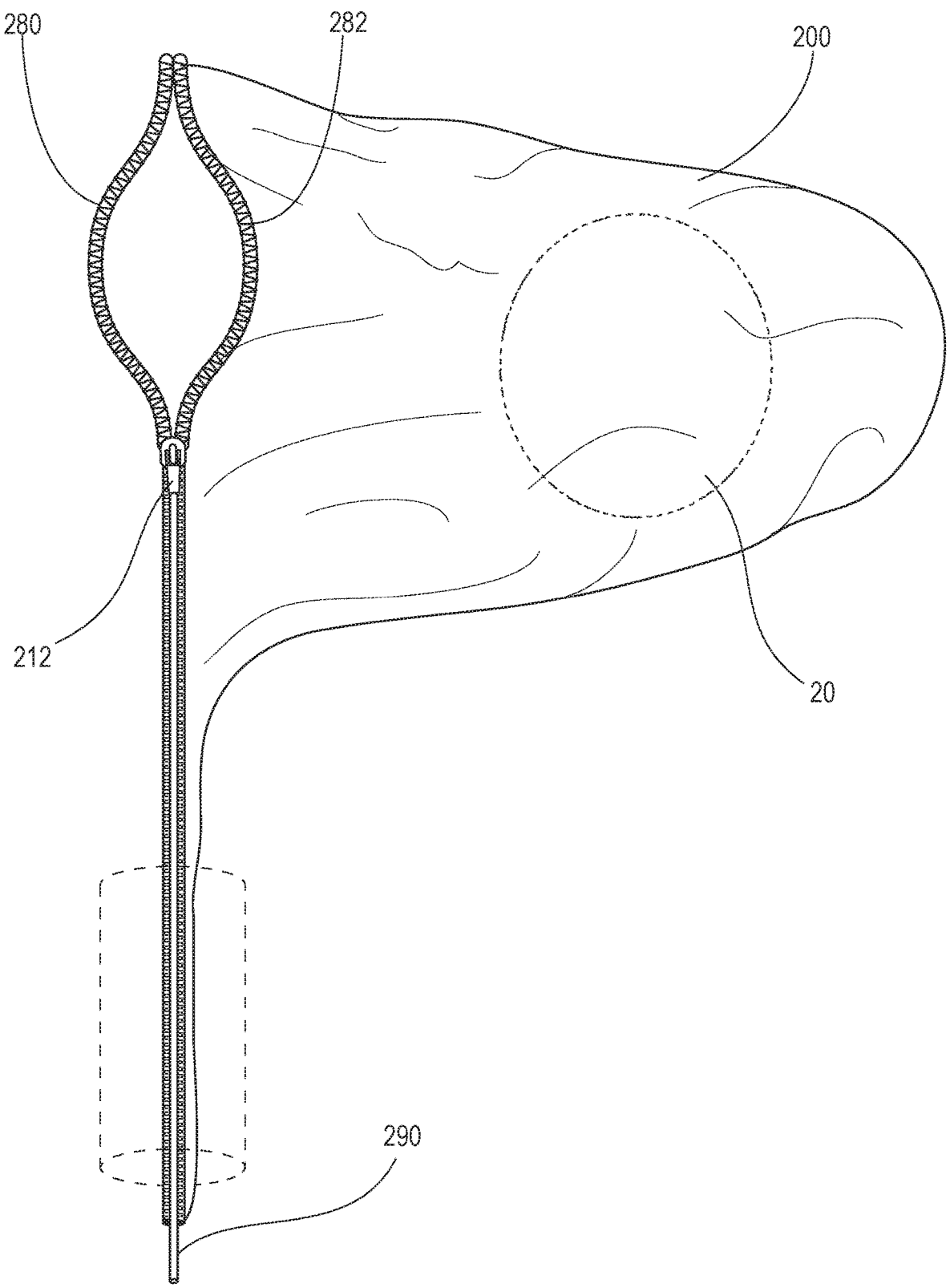
Figure 11:
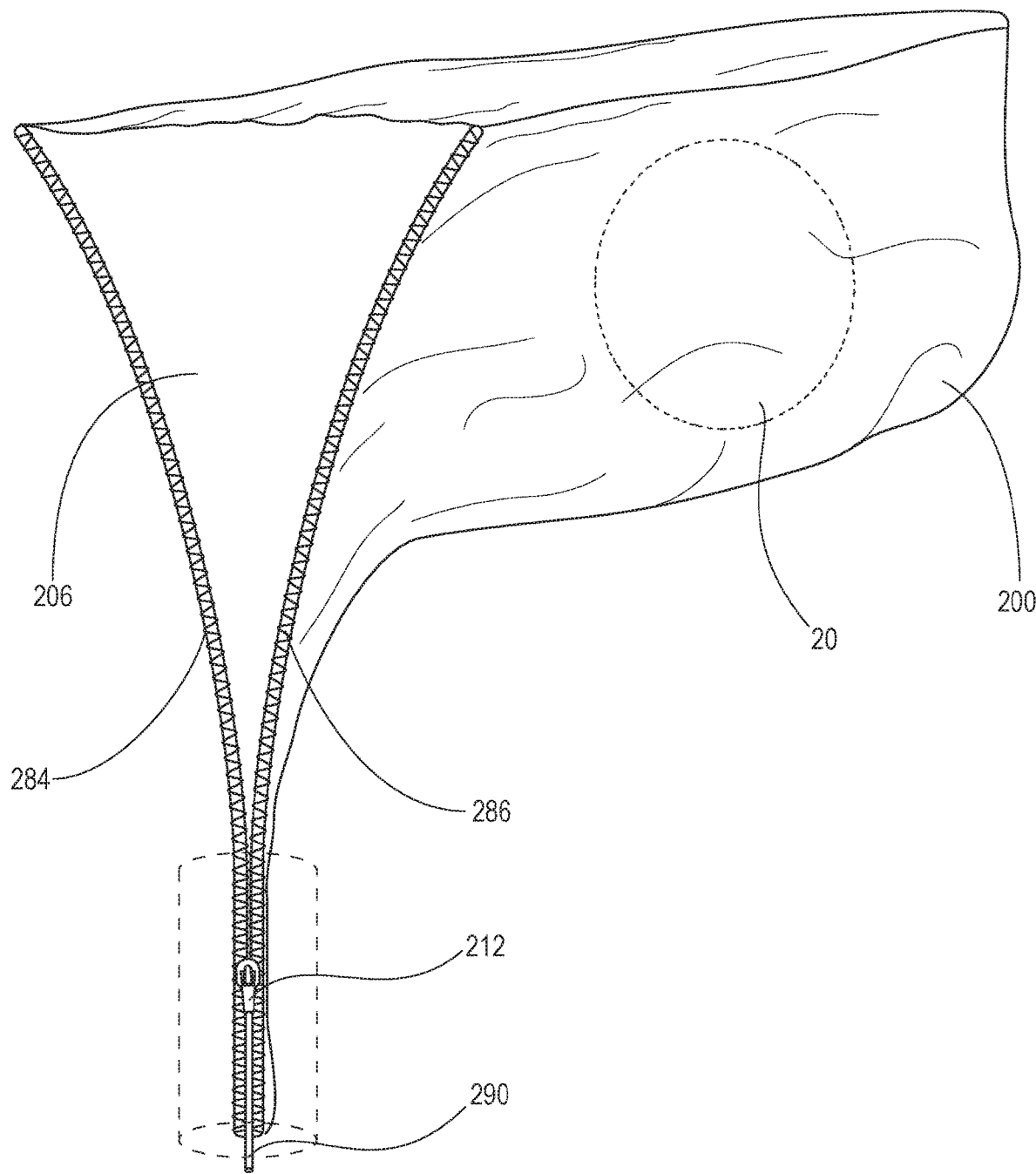
FIG. 11 depicts the capture mode operation of a tissue container similar to that of FIGS. 10A-C utilizing a triangular opening to capture a specimen instead of a circular opening.

Turning to FIGS. 10A-C, an embodiment of container 200 is shown in operation from deployment, capture of tissue specimen 20, and closure. This embodiment, along with others in which a closure mechanism is described for opening 206 and in which more than one opening is present, is useful for container closure in vivo—after the tissue specimen has been placed therein but prior to specimen 20 cutting or morcellation. For purposes of illustration, the schematic methods and container embodiments of FIGS. 10 and 11 show only one opening 206 through which a tissue specimen 20 moves as a physician or other user places specimen 20 within container interior 204. As described elsewhere herein, for container embodiments in which an opening 206 may be closed or sealed (e.g., the embodiments of FIG. 6-11) one or more additional openings 206 may be present. In particular, an additional opening 206 may be present in which a cutter or morcellator 400 is disposed, either integrally during manufacturing or assembly (such that container 200 and cutter 400 form an "all in one" container and cutting component) or by the physician or other user during the methods described herein. For example, in the embodiments of FIGS. 10 and 11, such an opening is not shown but may be present near the portion of container 200 shown disposed in body port 22. During use, a cutter or morcellator 400 (not shown), with or without a cannula 700, guard 300 or cannula having integrated protector elements (such as cannula embodiments 740, 770), in any combination, may be disposed within this additional opening in container near body port 22 and advanced into container interior 204 after the container closure mechanism 210 (in the case of FIGS. 10 and 11, zipper 212) is operated to close opening 206. Cutter 400 can then be activated, after performing any desirable tensioning or other steps as described herein, to cut or morcellate specimen 20 and to remove the processed specimen and any other tissue or bodily fluid contained in bag 200 out of the additional opening.

It is specifically within the scope of the present disclosure to employ methods using containers having one opening where that opening is not closed but rather moved outside the body port 22 and through which morcellator 400 may be deployed for tissue specimen 20 cutting and removal. It is also specifically within the scope of the present disclosure to employ methods using containers having more than one opening, which are contemplated for the containers shown in the examples of FIGS. 6-11 having closure mechanisms for one of the container openings, in which tissue may be cut/morcellated and removed through an additional opening. Variations of both methods and mechanisms/components to accomplish tissue capture and removal using containers with one or more openings are also within the scope of the present disclosure.

FIG. 10A shows this embodiment of container 200 in its compact form that can be inserted through a port 22 (such as one created by surgical incision or a natural opening such as a vagina, rectum, esophagus, etc.). Two pre-tensioned spring elements 280, 282 may be associated with container opening 206 as seen in FIG. 10B. These elements can be made of any medical grade material having physical characteristics sufficient to actively force container 200 open when deployed, to aid a user in opening container 200, or to at least not materially interfere when a user is opening container 200 to capture a tissue specimen as shown in FIG. 10B. This may be accomplished by way of, e.g., elements 280, 282 being comprised of a shape memory material or by the use of a removable sheath (not shown) that constrains elements 280, 282 until such time that the physician determines the enclosure 200 is to be opened—typically once it is in the body cavity 30. Note that at distal ends 280a, 282a, elements 280 and 282, respectively, may be joined together or otherwise integrated to form a single element so that the entire container edge 206a effectively is defined by elements 280, 282.

As shown in FIG. 10B, the opened bag 200 may take the shape of, e.g., a non-porous fluid-impermeable fish net, which can be manipulated on its proximal end 254 by the physician or surgeon for capturing tissue specimen 20 into the bag's interior 204. Container opening 206 is characterized by a generally oval or circular shape defined by edge 206a, a shape driven at least in part by the configuration of elements 280, 282 when deployed.

FIG. 10C shows the container opening 206 being closed with specimen 20 inside the container interior 204. This may be accomplished through the use of a stiff rod 290, which is attached at one end to a zipper mechanism 212, that can be pushed by a physician through the body port, or natural opening, and possibly through a cannula lumen if desired, to draw opposing sides of bag edge 206a together, forcing elements 280 and 282 to straighten as the container closes 200. Other mechanisms to close and seal container 200 as described herein are contemplated, including the use of a sliding sheath to mate the sides of container edge 206a and seal the opening 206 via, e.g., a sealable bag design. Once the container 200 is sealed, tissue specimen 20 can then be morcellated, through another predetermined opening 206 (not shown) in the bag 200 through which the cutter 400 is fit or disposed, or otherwise processed or manipulated; the device can then be extracted from the patient's body. In an all in one concept (not pictured), the container 200 can be physically attached to the morcellation device 400 through any suitable means or processes, such as, e.g., a co-molding process. Container 200 can include a hard retainer at this additional opening (not shown) that is sealed and attached to the tissue cutter.

FIG. 11 shows an embodiment of container 200 in which the opening 206 takes on a more triangular shape defined by edge 206a. As with the FIG. 10 embodiment, in its compact form the FIG. 11 embodiment can be inserted through a channel, a port 22 (such as one created by surgical incision) or natural opening (e.g., vagina, rectum, esophagus, etc.). Two pre-tensioned spring elements 284, 286 may be associated with container opening 206. These elements can be made of any medical grade material having physical characteristics sufficient to actively force container 200 open when deployed, to aid a user in opening container 200, or to at least not materially interfere when a user is opening container 200 to capture a tissue specimen as shown in FIG. 10B. This may be accomplished by way of, e.g., elements 284, 286 being comprised of a shape memory material or by the use of a removable sheath (not shown) that constrains elements 284, 286 until such time that the physician determines the container 200 is to be opened—typically once it is in the body cavity 30.

In this FIG. 11 embodiment, container opening 206 is characterized by a generally triangular or circular shape defined by edge 206a, a shape driven at least in part by the configuration of elements 284, 286 when deployed and the fact that their distal ends 284a, 286a, respectively, are not connected to one another but rather are connected by a portion of the container 200 material (in contrast to the FIG. 10 embodiment).

During use, the FIG. 11 embodiment may be closed as described above in connection with the FIG. 10 embodiment, once the container 200 is sealed, tissue specimen 20 can then be morcellated, through another predetermined opening 206 (not shown) in the bag 200 through which the cutter 400 is fit or disposed, or otherwise processed or manipulated; the device can then be extracted from the patient's body. In an all in one concept (not pictured), the container 200 can be physically attached to the morcellation device 400 through any suitable means or processes, such as, e.g., a co-molding process. Container 200 can include a hard retainer at this additional opening (not shown) that is sealed and attached to the tissue cutter.

Other container embodiments may include features that stiffen the container 200 and/or enable closure of a container opening associated with a closure mechanism 210 through a natural body port (e.g., transvaginally) without the need of assistance from tools deployed through other ports. In some embodiments, enclosure 200 may include stiffening elements and two openings having closure mechanisms 210 (in addition to the additional opening through which a cutter and optionally one or more additional components may be deployed), one or both of which can be closed with the use of a robot and/or instruments from the one or more other ports. Container closure could be accomplished by any number of mechanisms 210 or methods, such as the use of one or more drawstrings, magnets, zipper or any other closure mechanism 210 such as described elsewhere herein. In some embodiments, container closing may be accomplished through the natural body port; e.g., in a gynecological procedure, through a patient's vagina 32, such as when an open end of bag 200 captures the tissue specimen 20 (e.g., uterus) and one or more stiffening members in container provides the structure necessary to enable a physician or other user to employ a zipper, pulley or other mechanism associated with container 200 to close it. In other embodiments (not shown), container 200 may include a flap that may be closed by a physician or other user via a mechanism such as, e.g., a zipper or drawstring after tissue specimen 20 is captured within container interior 204, thus sealing container 200. In such an embodiment, container 200 may be closed by robotic and/or other instruments via one or more surgically-created ports other than a natural body port, such as, e.g., abdominal ports. In other embodiments, container 200 may include one or more stiffening members and a zipper or other closure mechanism 210 that closes bag 200 in a direction from the body's natural port (e.g., vagina) towards the distal end of the container or bag 200. This embodiment affords a way for the one or more stiffening members to be used to close container 200.

Other embodiments of container 200 may include closure mechanisms 210 involving one or more magnets, such as those that may be automatically triggered via a linkage of multiple magnets. Such a linkage can allow the container opening 206 to open wide enough to permit entrance of tissue specimen 20 therethrough and into container interior 204, but then the linkage can close the container and seal the tissue and liquids inside. For example, container 200 may include a series of magnetic strips along the bag's length that may be activated mechanically, magnetically, electromagnetically or otherwise to join together in a hinged relationship by virtue of magnetic force to close enclosure 200 after specimen 20 has been placed therein. Additional embodiments contemplated herein include the use of a magnetic closing mechanism in which adjoining portions of container edge 206a are lined with one or more magnets such that magnets of opposite polarity mate to join portions of the edge 206a together to close container opening 206. In one configuration, zippers as shown in the various figures and embodiments herein may be replaced by or supplemented with magnets to effect adequate and reliable, and perhaps more automatic, container closure.

Yet further mechanisms for closing container opening 206 as contemplated by the present disclosure include those in which the container distal end 255 near opening 206 (or any portion of container near an opening 206) may be rolled or folded upon itself such that the edge 206a mates to close opening 206, perhaps supplemented by a clip, hook and loop-type fastener, latching mechanism or the like on or associated with bag surface 202 to secure the folded or rolled portion of container into place.

As described herein, it may be useful to place axial tension on container 200 after the tissue specimen 20 is captured but prior to and/or during all or a portion of the tissue morcellation process. FIGS. 12-14 depict embodiments of the present disclosure in which tensioning of container 200 during use may variously be accomplished.

Figure 12A:
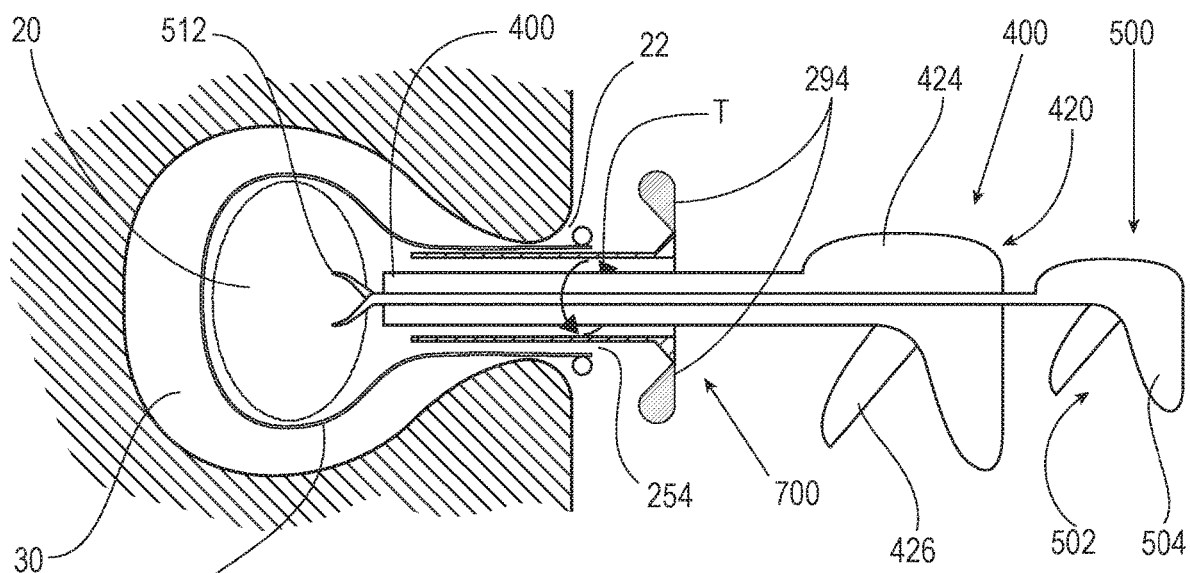
FIGS. 12A-C depict the operation of a tissue container utilizing a twist-to-tension feature.
Figure 12B:
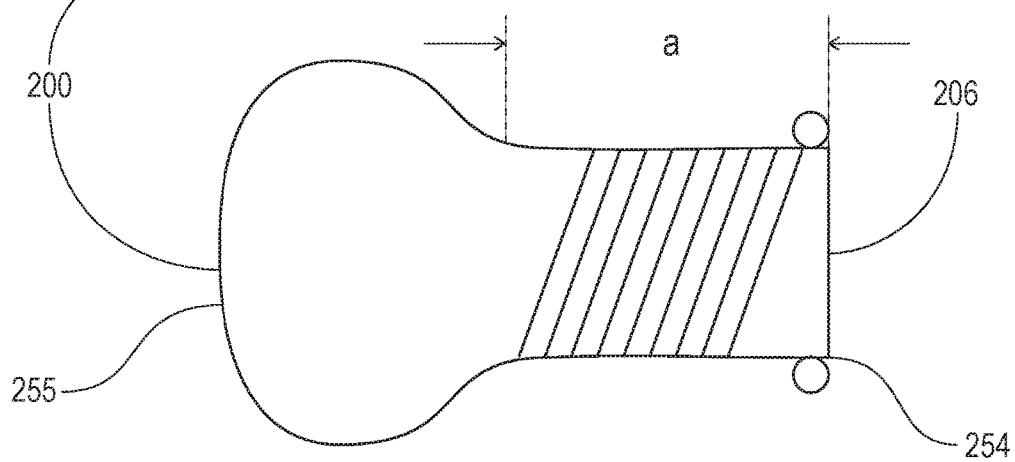
Figure 12C:
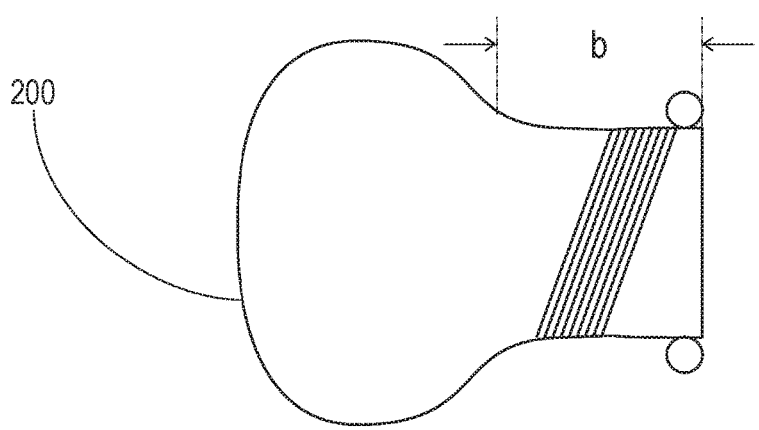

FIGS. 12A-C illustrate an embodiment of container 200 and its use in vivo with components of a system of the present disclosure where a portion of container 200 may be twisted, with or without the use of a handle 292, as a way to apply tension to container 200, thereby shortening its axial length and facilitate efficient and accurate processing of tissue specimen 20.

In the schematic of FIG. 12A, container 200 is shown deployed in a patient working cavity 30, having within its interior 204 a captured tissue specimen 20. A tissue grasper 500 is shown in apposition with the specimen 20 and extends out of a distal end 420 of cutter/morcellator 400. A proximal portion 502 of the tissue grasper terminates in a handle 504 that includes a trigger 506 for activating the tissue grasper distal portion 510. Likewise, a proximal portion 422 of cutter/morcellator terminates in a handle 424 that includes a trigger 426 for activating the cutter blade 408. A cannula 700 around which container 200 is placed, having a central lumen 702 through which are disposed cutter 400 and tissue grasper 500 is also shown in the patient's access opening 22 and at least partially into working cavity 30. A handle 254 is disposed at the proximal end 254 of container 200 in the vicinity of patient access opening 22. Handle 254 may take on the configuration as shown in FIG. 12, or it may be larger or have additional features to facilitate ease of use. Handle 254 may be attached onto or be an integral part of container 200; alternatively, handle 254 may be added onto the bag 200 during the procedure, after it is extracted from the patient port (e.g., vagina, etc.) and prior to the bag shortening step. Handle 254 may be operated manually or by any number of automated mechanisms, such as by the use of a motor used in connection with a geared transmission system or the like as described, e.g., below in connection with the embodiments of FIGS. 13 and 14.

In use, a physician or other operator applies tension on container 200 by twisting it, in one embodiment by use of handle 254, in the direction T indicated in FIG. 12A. This act of twisting shortens the bag 200, thereby putting tissue specimen 20 into contact with the container distal end 255 as shown in FIG. 12A. Together with the optional application of force on specimen 20 and/or by gripping at least a portion of specimen 20 with grasper 500, continued twisting brings tissue specimen 20 up against the morcellation blade 408 to facilitate the beginning of the process of cutting the tissue specimen 20. As the tissue specimen 20 is processed by the cutter, continued twisting of bag 200 and optional application of axial force via grasper 500 will facilitate a reliable and efficient cutting effort as enclosure 200 continues to shorten and the specimen 20 is reduced in size as it is processed by the cutting action of blade 408.

FIGS. 12B and 12C illustrate how container 200 may be shortened, depicting an initial linear dimension 'a' of a portion of enclosure 200 that is transformed to a shorter dimension 'b' by virtue of this twisting action. The difference between dimension 'a' and dimension 'b' (a-b) may vary, depending on the application for which the system is being used. In some instances, such as a hysterectomy, this difference can be approximately 20.0 centimeters, but could be as much as about 50.0 cm or more or as little as 1.0 cm or less.

FIGS. 13A-C depict another embodiment in which enclosure 200 may be tensioned by an automated telescoping mechanism 800 to effect efficient processing of the tissue specimen 20 as described above. Here, container 200, tissue grasper 500, cutter/morcellation device 400 and their various features and components are shown in vivo in FIG. 13A in similar fashion to FIG. 12A. Tissue specimen 20 is disposed in container interior 204.

FIGS. 13A-C show a retention piece or clamshell housing 812 attached to a proximal end 254 of container 200 in the vicinity of container opening 206. Retention piece 812 may be so attached after the opening 206 is in place outside the patient's body at opening 22 as shown in FIG. 13A; alternatively, embodiments may include a container 200 having a retention piece pre-attached to or integral with container 200. Clamshell 812 can include handles (not shown) as described above in connection with the FIG. 12 embodiment. These handles can be used in twisting container 200 as described herein or for simple axial tensioning along a long shaft as described below in connection with FIG. 20.

Retention piece 812 allows for ready manipulation of the system 800 and container 200 to effect the desired tension during the processing of tissue specimen 20. Housing 812 includes bearings 804 that are axially slidable on rails 806 to keep container 200 aligned in a relatively straight configuration as a lead screw or drive gear 834 powered by a motor 832 pulls container 200 out of the patient working cavity 30 and through opening 22 in a linear fashion. By automating the container retraction process, the physician or operator is free to have one hand on the morcellator 400 and the other hand on the tissue grasper/tenaculum 500 as the container is tensioned and retracted automatically by telescoping mechanism 800. A control module 802 (not shown) can be programmed to provide a specific level tension or axial force on container 200 during operation to keep tissue specimen 20 flush with or in apposition against the morcellator blade 408 as described above. Control module 802 can also be programmed or set to pull the entire bag or container through the patient's access opening 22 when the tissue specimen 20 is or has become by virtue of the cutting action of cutter 400 small enough to fit therethrough. This container tensioning system 800 can be attached to a cannula 700 or can be separate from cannula 700. And while telescoping mechanism 800 is shown in FIGS. 13A-C as being motor driven and controlled by a programmable control module 802, mechanism 800 may also be otherwise manually activated and operated by the physician as desired, semi-manual embodiments may be used, such as motors operated and controlled by the physician or other operator, or mechanical (non-electrical and/or non-automated) embodiments operated and controlled by the physician or other operator. In other embodiments, mechanism 800 may operate via a rack and pinion mechanism, either by hand or motorized with a control system to apply a constant or controlled but variable force on container 200 or to operate under velocity control, etc.

FIGS. 14A-C depict another embodiment in which enclosure 200 may be tensioned by linear motion that is achieved through a telescoping or helical cam mechanism 820. Here, container 200, tissue grasper 500, cutter/morcellation device 400 and their various features and components are shown in vivo in FIG. 14A in similar fashion to FIGS. 12A and 13A. Tissue specimen 20 is disposed in an interior 204 of bag 200.

Mechanism 820 includes a helical or cylindrical tube 822 as shown in the cross-sectional views of FIGS. 14A-B. Within a central lumen 824 of tube 822, typically on an interior wall is disposed a helical groove, ridge or other feature 838 suitable for receiving or otherwise engaging with a clamshell element 812, not unlike that of the FIG. 13 embodiment. As tube 822 is rotated along a central longitudinal axis, either by a motor 832 as shown in FIGS. 14A-C or by hand or other mechanical means (not shown), container 200 is then drawn linearly down the cylinder lumen 824 by the cooperation of clamshell element 812 and cooperating bearings 804 in the groove or ridge feature 838. Alignment shafts or guide rails 830 and associated bearings help keep proximal end 254 of container 200 in proper alignment and to prevent rotation of enclosure 200. An optional bearing 828 disposed at a distal end 825 of helical tube 822 enables mechanism 820 to spin with respect to the various components of the present disclosure (e.g., container 200, cutter 400, grasper 500, cannula 700, etc.). Between 1 and 4 or more shafts may be used.

A drive gear 834 and a driven gear 836 are shown in FIGS. 14A-C, and in cross section along with rails 830 in FIG. 14C. A motor 832 powers rotational movement of drive gear 834 to which it is connected, which in turn effects rotational movement of driven gear 836 that rotates tube 822.

In an alternative configuration (not shown), helical cam mechanism 820 may be disposed within an interior 204 of container 200 and operate as described herein. In such a configuration, container 200 may be drawn linearly around the outside of tube 822 by the cooperation of clamshell element 812 and cooperating bearings 804 in groove or ridge feature 838 that is located on an exterior surface of tube 822 rather than within a lumen 824 of tube 822.

Figure 15A:
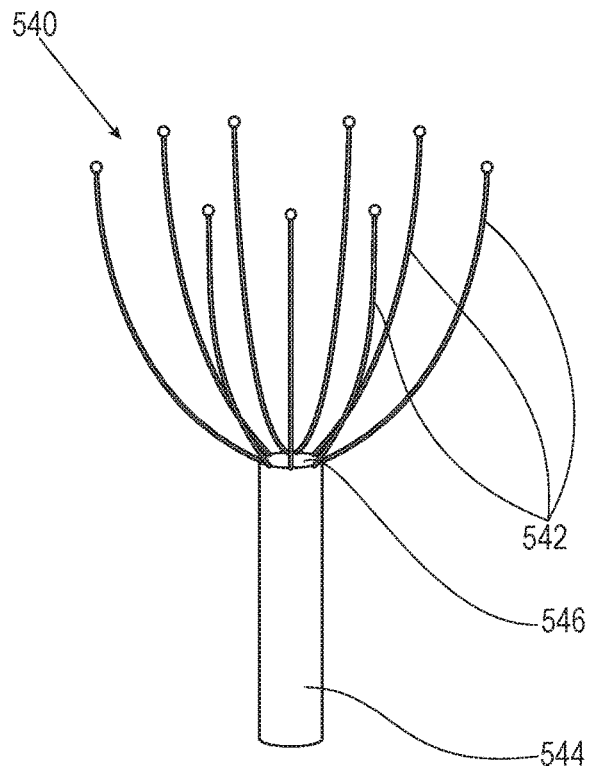
FIGS. 15A-D depict the operation of a tissue grasper having tines.
Figure 15B:
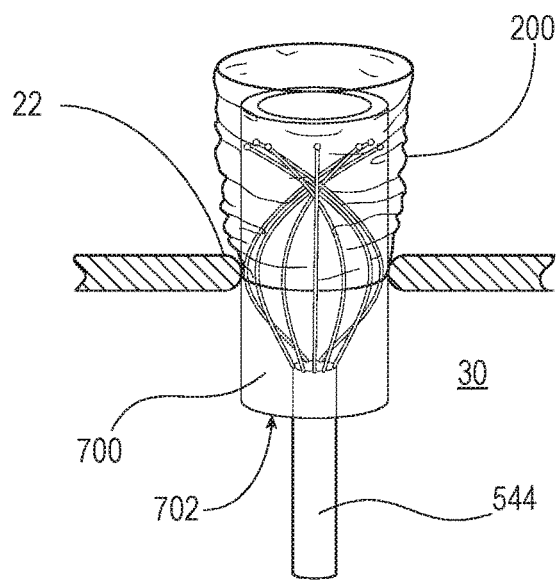
Figure 15C:
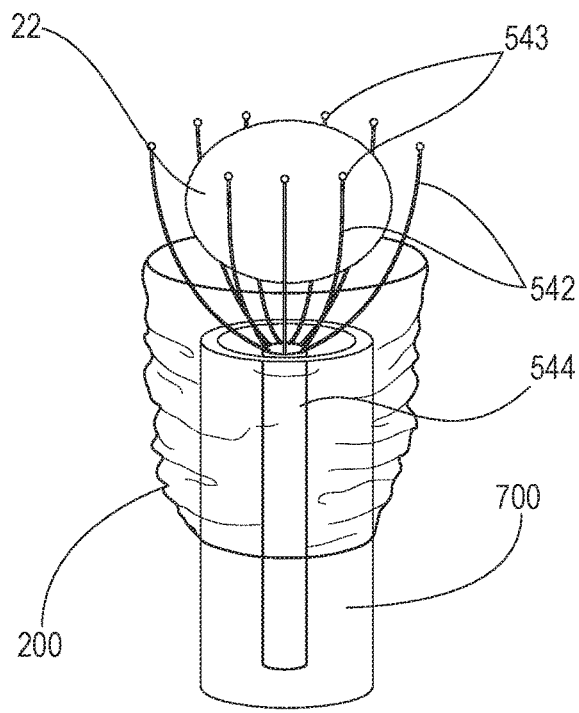
Figure 15D:
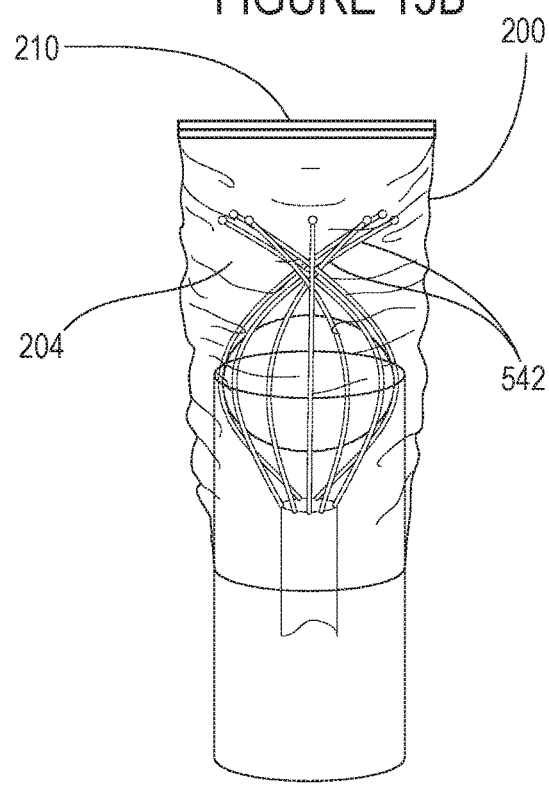

FIGS. 15A-D depict an embodiment of an introducer 544 and a blunt-tined tissue grasper or tenaculum 540 and a method of its use with the systems and components of the present disclosure. In FIG. 15A, grasper 540 is shown as including any number of tines 542 extending from an interior volume or lumen 402 of a cutter or morcellator 400. Tines 542 on their proximal end (not shown) may be connected to or integrated with a pusher or other instrument that may be manipulated, with or without a handle and/or trigger mechanism to move tines 542 of grasper 540 through cutter lumen 402 and into an interior 546 of introducer 544 as shown in FIGS. 15B-D.

Tines 542 may be made from any suitable biocompatible material, and in particular can include plastic or metallic materials that exhibit spring-like or even shape memory behavior so that they take on a desired configuration (such as that shown in FIG. 15A) when disposed outside of any constraining structure (e.g., cutter 400 and/or introducer 544). The number of tines 542 may be optimized, along with their cross-sectional shapes and how they are configured and arranged relative to one another, to balance the requirements of being able safely and reliably to capture and move a tissue specimen 20, maintain a desired shape when deployed, and be flexible enough to collapse within the any constraining component such as cutter 400 and introducer 544. In the open, fully unconstrained configuration of grasper 540 shown in FIG. 15A, tines 542 extend beyond a distal end 420 of introducer 400, springing to a predetermined "capture" arrangement as would be assumed within a patient working cavity 30 for placement of a tissue specimen within a volume created among the tines as so deployed.

In FIG. 15B, tines 542 are shown extending out from a cutter distal end 420 as discussed with respect to the view of FIG. 15A. However, here, tines 542 have not taken on their fully open or unconstrained shape as they are partially constrained within a central lumen 702 of cannula 700. Here, introducer 544 has been placed within the body of a patient, perhaps into a working cavity 30 but in the view of FIG. 15B at least through a patient's access opening 22 for use according to methods of the present disclosure. Container 200, which optionally may be integrated with introducer 544, is shown surrounding distal end 548 of introducer 544 and is within the interior of patient's body.

FIG. 15C depicts grasper 540 capturing a tissue specimen 20 after tines 542 have been axially extended beyond introducer distal end 548. In this particular sequence, tissue specimen 20 has been captured from patient cavity 30 and lies within the assembly of tines 542. Specimen 20 and a portion of tines 542 are being moved into an interior of container 200 through container opening 206 and towards the cutter/morcellator distal end 420 on which a blade 408 may be disposed. Optional atraumatic tips 543 may be disposed on an end of one or more tines 542 to prevent or mitigate damage to container 200 or tissue other than tissue specimen 20. In FIG. 15D, the grasper 540 and specimen 20 are now completely contained within the interior 204 of container 200. Via other tools such as may be used via a laparoscopic port or via another closure mechanism 210 as variously described herein, the container opening 206 is now closed and sealed along its edge 206*a*, safely securing specimen 20 therein. At this point, specimen may be prepared for morcellation as described elsewhere herein, and grasper 540 may be advanced out of the distal end 548 of introducer 544, all within the interior 204 of sealed bag 200, so that the specimen 20 may be released from the tines 542 and the tines may be retracted axially through the lumen 402 of cutter. The physician may then manipulate container 200, cutter 400 and any other instruments (such as a traditional grasper shown elsewhere herein) to pull tissue specimen towards blade 408 for morcellation and removal through the patient's body.

One aspect of the systems and method described herein is the concept of a guard or protector element or component 300. Among other benefits, guard 300 helps to prevent container or enclosure 200 from contacting the cutting mechanism 400. Guard 300 also inherently helps to prevent cutter 400 or other components of the present disclosure from damaging or engaging with tissue in the patient's body that is outside the container interior. In a gynecological example, such tissue may include, e.g., the bowel and/or bladder or other tissues that may be in the vicinity of the patient's pelvic cavity in which the system of the present disclosure is deployed. Other tissues in other cavities, such as, the abdominal or thoracic cavities, may also be inherently protected by guard 300 during use. Guard 300 can take several configurations. In one embodiment such as that shown in FIG. 1, guard 300 is a cone-like element taking on a shape of, e.g., a collapsible or partially collapsible funnel that can compress and enter a deployed container interior 204 through a patient port then expand and accommodate the tissue specimen 20 that is to be removed. In FIG. 1, guard 300 is slightly or moderately asymmetric relative to its central axis, such that it is not a right circular conical shape (or frustum thereof) but rather an oblique circular conical shape (or frustum thereof). However, guard 300 may take on a conical shape in the form of a right cylindrical cone or frustum in some embodiments. The asymmetry of guard 300 shown in FIG. 1, forming a frustum of an oblique cone, aids in guiding tissue specimen 20 to a particular portion of cutter blade 408, as does cannula asymmetric extension 776; benefits of this guiding action is discussed below in greater detail.

This embodiment of guard 300 is shaped such that a tensioned bag 200 containing specimen 20 cannot make contact with the cutter 400 and/or tissue grasper/tenaculum 500. Guard 300 possesses adequate hoop strength to prevent it from collapsing, fully or partially, on or near blade 408 while guard 300 is axial tension with container 200. This embodiment of guard 300 also has sufficient stiffness to prevents it from contacting blade 408 when loaded radially. The guard 300 could include ribs of spring steel or shape memory material, such as nickel titanium alloys, which could be coated in silicone, PTFE, ePTFE or other plastic which can be molded around or layered above or below the ribs.

Figure 16A:
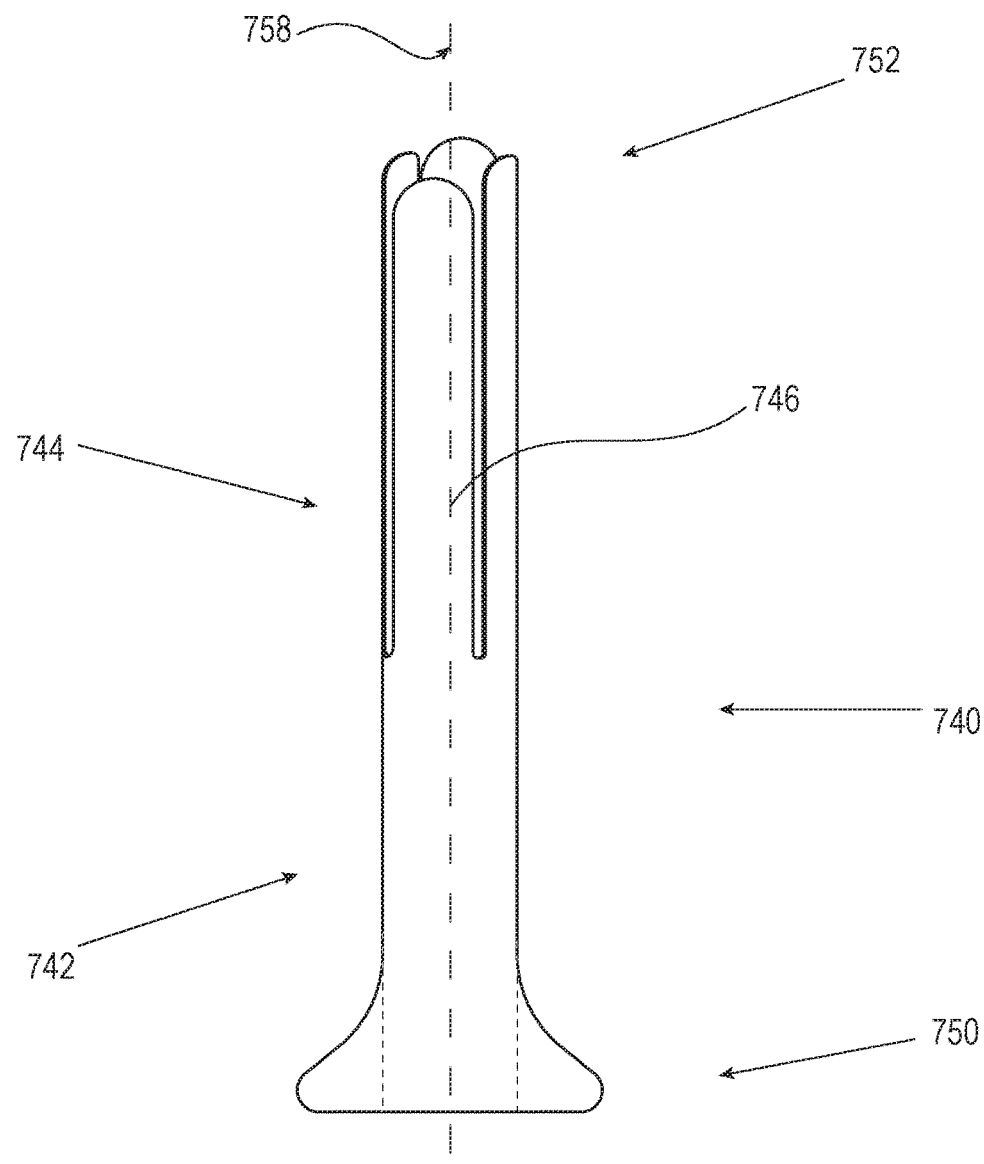
FIGS. 16A-B depict a cannula integrated with a guard or protector portion having flexible/expandable protector elements.
Figure 16B:
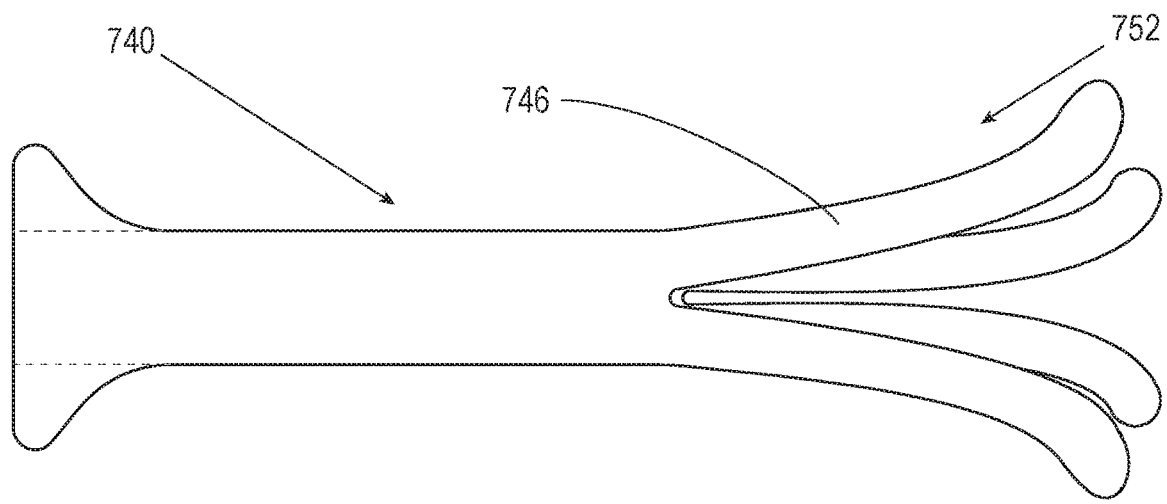

FIGS. 16A-B depict a cannula embodiment 740 having a main portion 742 and a protector portion 744. Protector portion 744, which can function as a guard 300 to protect container from damage during cutting and which can also aid in guiding a tissue specimen 20 towards cutter blade 408, is shown including a number of elements 746. Protector elements 746 in this embodiment are integrated as part of cannula 740. A cannula proximal end 750 may incorporate a flared feature as shown in FIGS. 16A-B for ease of handling by a physician or other operator. Cannula proximal end 750 may also or instead include one or more handles (not shown) for similar ergonomic and operational advantages.

There can be anywhere from one to thirty or more protector elements 746 that are a part of cannula protector portion 744 (four such elements 746 are shown in FIGS. 16A-B). Elements 746 may be attached to cannula main portion 742 or may be of an integral, seamless construction such that cannula 740 is a unitary member. Elements 746 are designed to provide enough stiffness to serve their guarding and guiding functions but to have enough radial flexibility relative to a cannula central axis 758 to bend and take on a variety of configurations. In one construction, protector elements 746 can be spring-loaded. Elements 746 may be made from a shape memory material such as a nickel titanium alloy, a spring steel alloy, a plastic or other flexible metal such that the they can collectively have a small diameter when passing through the patient opening 22 or other port, and open to a larger diameter, either by activation or release from a constraint (or both) once inside the patient's working cavity 30. Elements 746 may include rubber or other relatively soft components on their distal tips to help prevent container damage, particularly from puncture, during the various steps in the methods described herein. In addition, a physician or other operator may use grasper 500 to grip at least a portion of specimen 20 and pull the tissue specimen 20 axially towards the cannula distal end 752 into contact with the protector elements 746 in general alignment with the cannula central axis 758. If the size of specimen 20 is large relative to the diameter of central lumen 702, this action will cause protector elements 746 to bend out radially to accommodate the specimen 20 therewithin. This action combined with the design features that permit elements 746 to bias inward but spring outward radially as described above demonstrates the utility of this embodiment 740 of cannula.

Once positioned as described, tissue specimen 20 may be drawn towards the cutter/morcellation 400, and in particular blade 408, by, e.g., tensioning of container 200 while optionally maintaining axial tension on specimen 20 by grasper 500, etc., as described elsewhere herein. As container 200 is tensioned, protector elements 746 provide a barrier between the morcellation blade 408 and container 200, protecting enclosure 200 from being pierced, torn or otherwise damaged during the cutting process to maintain the integrity of the container and preventing leakage of tissue or bodily fluids into the patient's body.

Figure 17A:
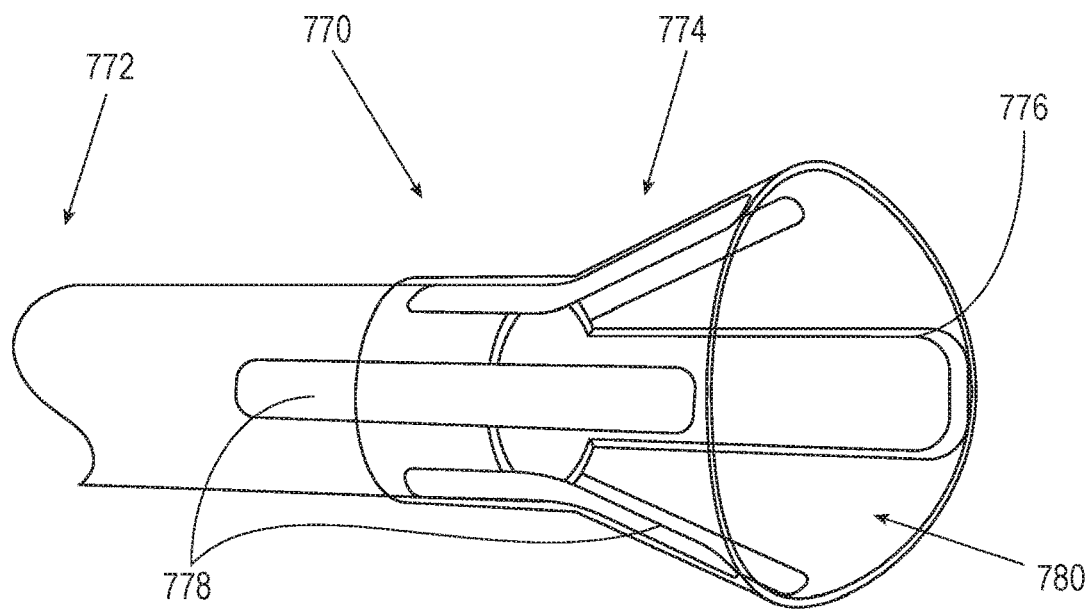
FIGS. 17A-C are various views of a cannula integrated with an asymmetric guard or protector portion and flexible/expandable protector elements encased in a protective material.
Figure 17B:
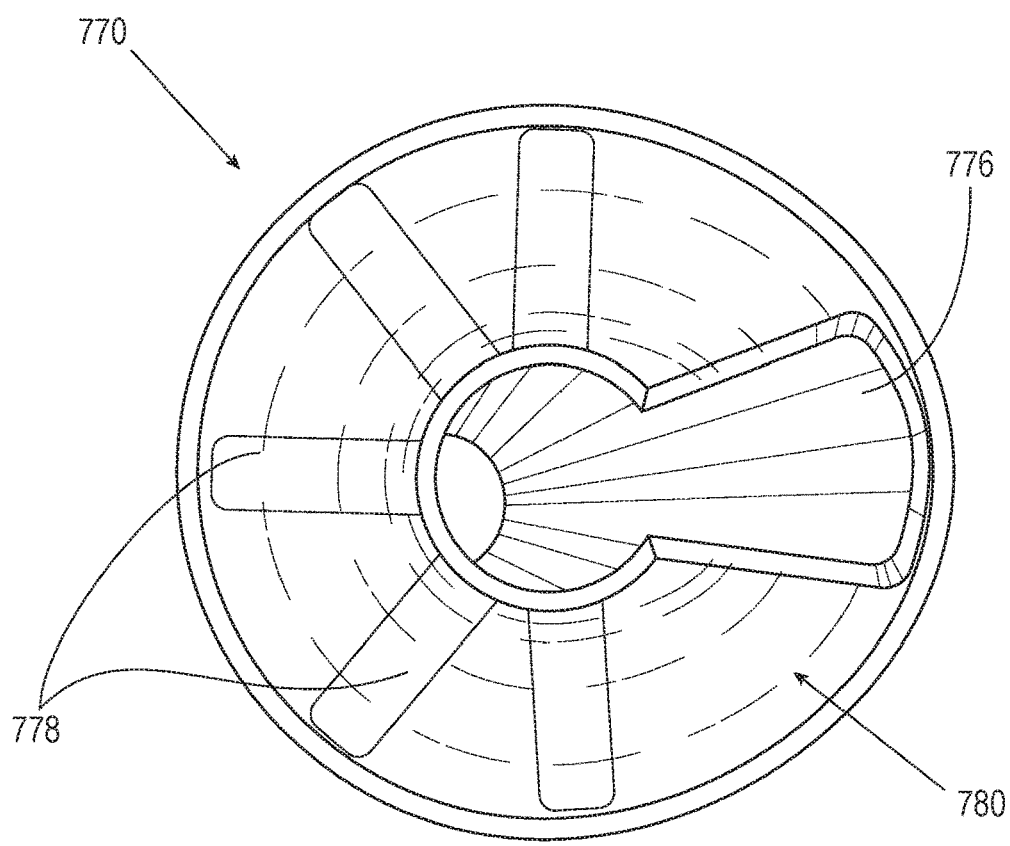
Figure 17C:
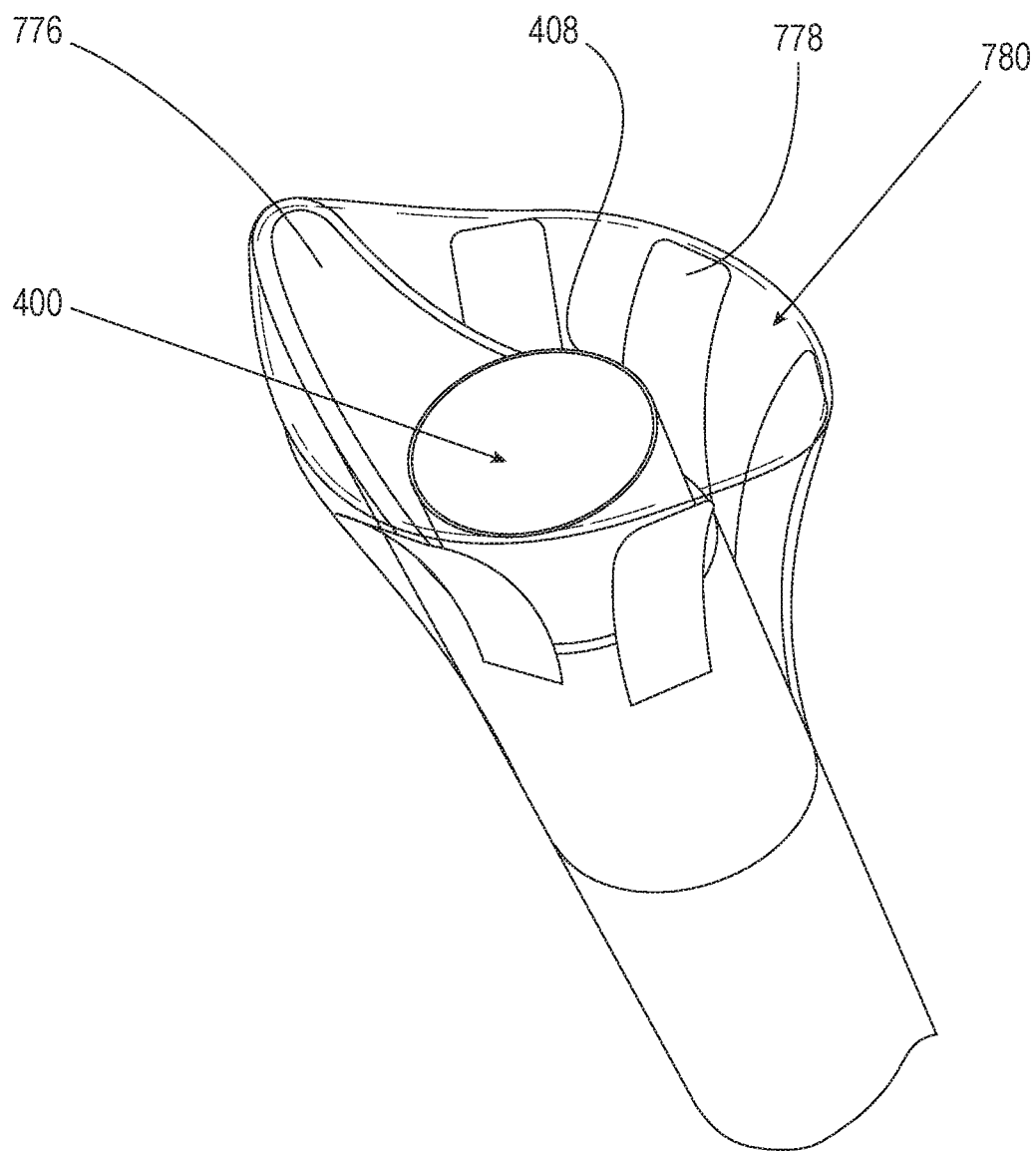

In another embodiment of the present disclosure, FIGS. 17A-C depict various views of cannula 770 integrated with a guard/extension 776, protector elements 778 and an enclosing element 780. FIGS. 18A-D depict cross-sectional (FIG. 18A), schematic end-on (FIG. 18B) and schematic side (FIGS. 18C-D) views of a portion of a system according to the present disclosure that incorporates the cannula 770 of FIGS. 17A-C, while FIG. 19 schematically depicts a system incorporating the elements of FIGS. 17-18 that utilizes a manually powered cutter 400.

Turning to FIGS. 17A-C, cannula 770 includes a protector portion 774 adjacent a main portion 772. Integrated with or attached to protector portion 774 is an extension 776, at least one protector element 778, and an enclosing element 780.

During methods of the present disclosure, it is advantageous to protect container 200 from being damaged by the blade 408 of the cutter/morcellator, whether or not that blade 408 is actively being used to process the tissue specimen 20 as described herein. It is also advantageous to guide tissue specimen 20 as it is processed by cutter 400 such that it "feeds" or can be preferentially directed to a portion of the system of the present disclosure such that a designated area of the blade 408 contacts the tissue specimen 20 as that specimen is drawn against the cutter 400 for processing. This embodiment presents design characteristics that facilitate these advantages.

In general, cannula 700, which may be inserted in the patient access opening 22, whether that opening is surgically created or a natural opening (e.g., vagina, rectum, esophagus, etc.), serves as a conduit through which a cutter/morcellator 400 may be inserted and tissue specimen 20 withdrawn according to methods described herein. Several approaches may be taken in utilizing the various embodiments of cannula 700, including its insertion into the opening 22 after container 200 has been placed into the patient working cavity 30 and before or after tissue specimen 20 is captured therein.

The cannula embodiment 770 of FIGS. 17-19 is also well-suited to accomplishing the various methods of the present disclosure as will be discussed below. Cannula 770 includes a main portion 772 having a proximal end 782 and a protector portion 774 having a distal end 784. As with the cannula protector portion 744 of FIGS. 16A-B, cannula protector portion 774 protects the bag or enclosure 200 from damage during tissue processing. Extension 776 is shown in the embodiment of FIGS. 17-19 as being an integral part of cannula protector portion 774 at cannula distal end 784. Extension 776 may also be a separate member that is attached to cannula distal end 784 and need not be made of the same material as the rest of cannula 770.

In the embodiment of FIGS. 17-19, extension 776 serves primarily to drive how tissue specimen 20 is cut or processed by cutter 400 during the methods disclosed herein. In particular, extension 776 will help to preferentially guide or position tissue specimen 20 such that cutter blade 408 is preferentially placed on a tangent to tissue specimen 20 near its outer surface 20a as seen in the schematic of FIG. 18B. As the cutter operates on specimen 20 in this manner, blade 408 creates a "peel" cut into specimen 20, much like the operation of an apple peeling machine, rather than "coring" into the specimen.

Figure 18A:
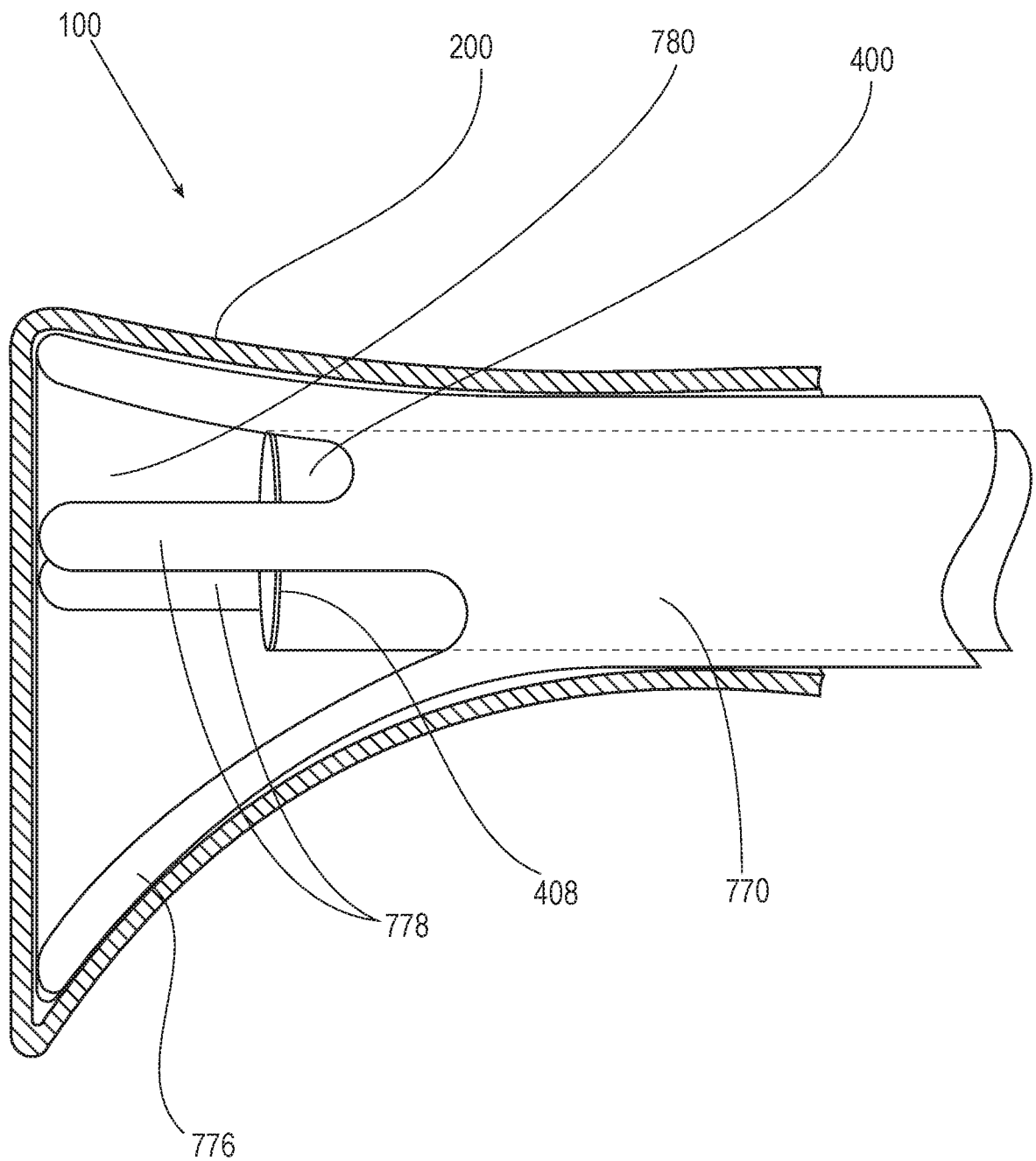
FIGS. 18A-D are various views of an end of the cannula of FIGS. 17A-CF.
Figure 18B:
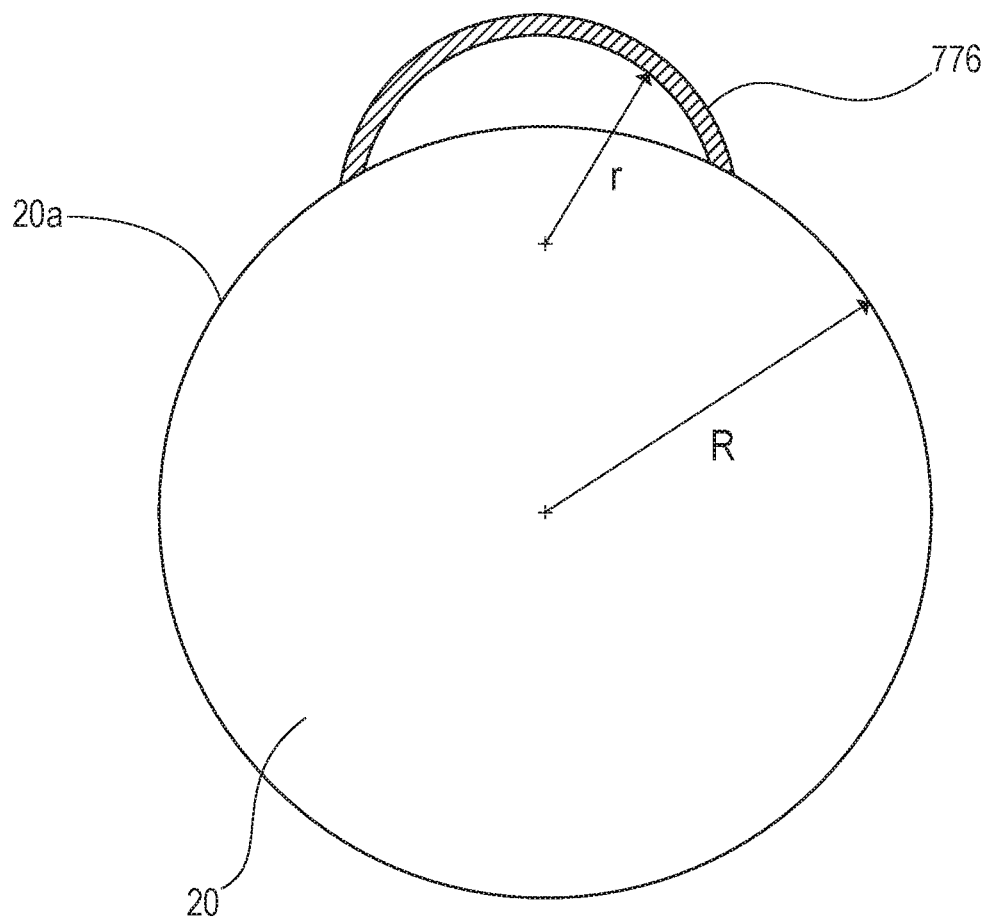
Figure 18C:
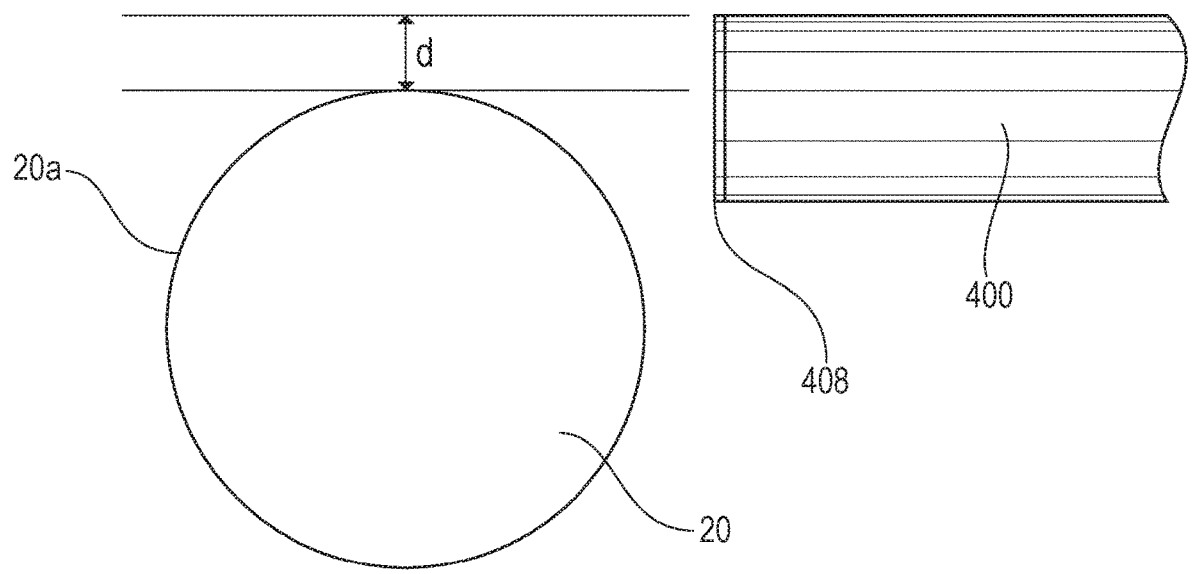
Figure 18D:
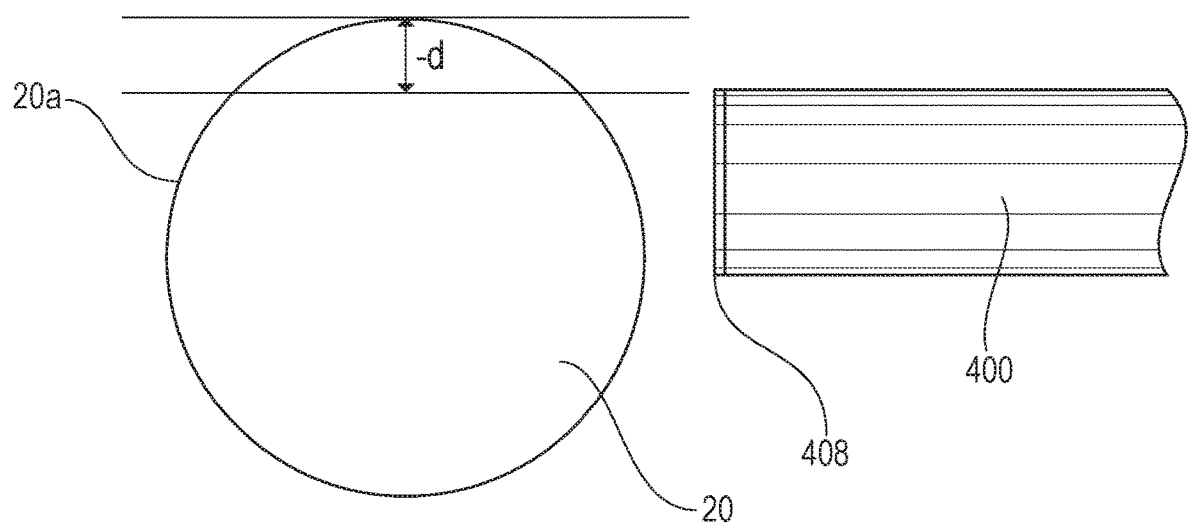
Figure 19:
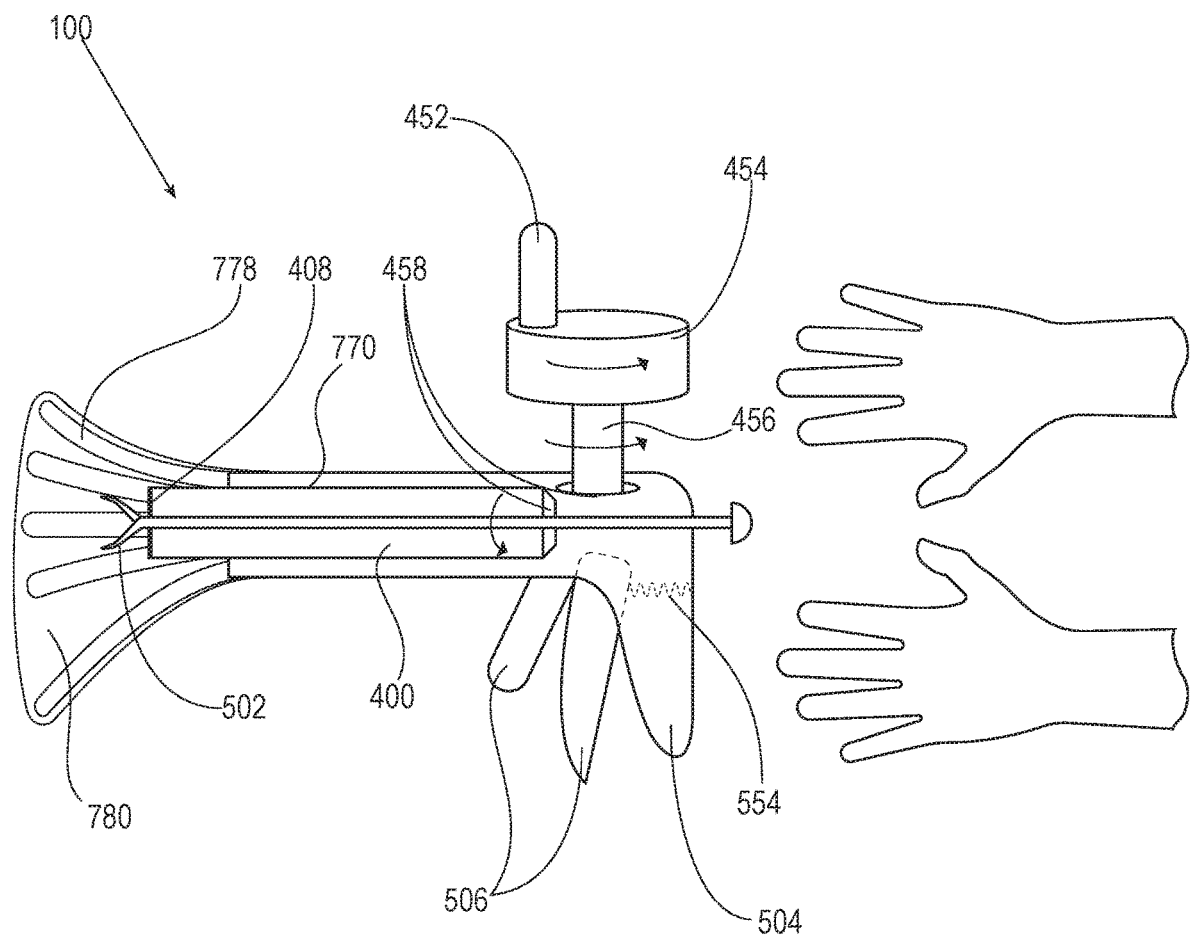
FIG. 19 is a side view of an embodiment of a system for tissue capture and removal featuring a hand-operated cutting mechanism.

FIGS. 18B-C show tissue specimen 20 interacting with extension 776 in an end-on view (FIG. 18B) and a side view (FIG. 18C) of the FIGS. 17-19 embodiment. A radius of curvature r for extension 776 may be designed to be sufficiently smaller than an idealized radius R of tissue specimen 20 such that an upper extent of cutter 400 is a positive distance d relative to a tangent to specimen outer surface 20a as shown in FIG. 18C. In contrast, if extension 776 radius of curvature r is not sufficiently small relative to radius R of specimen 20, an upper extent of cutter 400 is a negative distance relative to a tangent to specimen outer surface 20a as shown by the distance −d in FIG. 1d is a positive value with reference to a tangent to specimen surface 20a, systems 100 employing the embodiments of FIGS. 17-19 will tend to ensure such a "peel" cut of specimen 20 is effected by cutter 400 rather than a "coring" type of cut.

Such a configuration helps to control the tissue cutting process and gives the physician or other user confidence that, in what can be a "blind" process if no visualization instruments are used, tissue specimen 20 is being processed in a reliable and effective manner. It also serves to protect container 200 from being damaged by blade 408 as extension 776 can generally be made more durable and rigid than protectors 776. In the cross-sectional view of FIG. 18A, enclosure 200 is shown surrounding cannula 770 to illustrate, in a fully tensioned configuration where tissue specimen is no longer in bag interior 204, how protector portion 774 protects container 200 from damage during cutting/morcellation of tissue specimen 20 as described above.

A protector portion 774 having or more protector elements 778 may also be included in the embodiment of cannula 770. Protector portion 774 can function as a guard to protect container 200 from damage during tissue specimen cutting and can also aid in guiding specimen 20 towards cutter blade 408. Protector elements 778 in this embodiment are integrated as part of or attached to cannula 770. A cannula proximal end 782 may incorporate a flared feature and/or handle, as discussed in connection with the embodiment of FIGS. 16A-B for ease of handling by a physician or other operator.

There can be anywhere from one to thirty or more protector elements 778 in this embodiment 770 of cannula protector portion 774 (four such elements 778 are shown in FIGS. 17-19). Elements 778 may be attached to the main portion 772 of cannula 770 or may be of an integral, seamless construction such that cannula 770 is a unitary member. Protector elements 778 are designed to provide enough stiffness to serve their guarding and guiding functions but have enough radial flexibility to bend and take on a variety of configurations. In one construction, protector elements 778 can be spring-loaded. Elements 778 may be made from a shape memory material, a spring steel alloy or other flexible metal such that the they can collectively have a small diameter when passing through the patient opening 22 or other port, and open to a larger diameter, either by activation or release from a constraint (or both) once inside the patient's working cavity 30. Elements 778 may include rubber or other relatively soft components on their distal tips to help prevent container damage, particularly from puncture, during the various steps in the methods described herein. In addition, a physician or other operator may optionally use grasper 500, via gripping or holding at least a portion of specimen 20, to pull the specimen axially towards the cutter 400. If the size of specimen 20 is large relative to that of protector portion 774, this action will cause protector elements 778 to bend out radially to accommodate the specimen 20 therewithin. This action combined with the design features that permit elements 778 to bias inward but spring outward radially as described above demonstrates the utility of this cannula embodiment 770.

Incorporated with or attached to protector elements 778 on the cannula protector portion 774 may be an additional protective layer or element 780. As seen in FIG. 17-19, layer 780 may take the form of relatively thin material, such as a durable plastic material including urethane, polyurethane, thermoplastic resins such as polyester (e.g., PET), silicone, PTFE, expanded PTFE (ePTFE), etc., that can be made to encapsulate or otherwise cover one or all surfaces of protector elements 778. Element 780 may be constructed of multiple layers or components. Element 780 is compliant enough and is designed to be able to sustain flexure motion as protector elements 778 bend during use, while still being durable so that container 200 is protected from damage by any of protector elements 778 during use. Element 780 may also partially or fully cover and/or encapsulate extension 776. The choice of material used and/or any surface or other treatment for element 780 may also facilitate ease of use as tissue specimen 20 comes in direct contact with element 780 during the methods of the present disclosure. For example, if element 780 is constructed from PFTE or ePFTE, it may be in either in an extruded tubular or (multiple) sheet form and can be engineered to have optimal isotropic or selectively anisotropic mechanical properties (such as, e.g., permeability, tensile strength, stiffness, tear resistance, abrasion resistance) to facilitate motion of tissue specimen 20 thereover, be biocompatible, and adequately to protect container 200 and protector elements 778. As described previously with respect to container 200, element 780 may be coated with and/or constructed using one or more layers of hydrophilic or hydrophobic materials and/or other lubricating materials or otherwise treated to provide a low-friction environment for interacting with tissue specimen 20. Such coatings or layers may be discrete and applied during manufacturing in sequential fashion (e.g., three-dimensional printing, other known deposition techniques) or may be in a composite or alloy-like form during manufacturing and/or as-fabricated. Having a low-friction and/or lubricious surface for element 780 can facilitate methods of tissue cutting and removal according to embodiments described herein, as the specimen 20 can spin or otherwise move relatively easily against element 780. Alternatively, all or a portion of element 780 may be constructed or treated to have a surface finish that is relatively rough, for example, near cutter blade 408 so that the tissue specimen is stable as it is being morcellated or cut. Differential surface finishes, treatments, or materials used for element 780 in any given embodiment, therefore, are contemplated herein.

In some embodiments, including those in components shown in FIGS. 16-19, features or elements can be included to limit the maximum opening size of the frustum or cone-shaped protector portions 744, 774 in their expanded configuration (as such configuration is exemplified in the views of FIGS. 16B, 17A-C, and 18). This may be desirable in methods disclosed herein where the body cavity 30 in which the systems are disposed may have sensitive organs or structures, for example, that could be damaged or otherwise negatively affected by a freely-expansive protector portion 744, 774. These limiting features, not shown in the Figures, may be, e.g., one or more circumferentially-disposed stiffening element(s) included around protector portions 744 and/or 774 in one or more locations, such as a distalmost edge, one or more intermediate locations, or even on a more proximal location thereon. Such limiting features can also serve to increase the hoop strength and resistance to radial deformation when the portions 744 and/or 774 take on their expanded shapes. In addition, such limiting features may also help to facilitate contraction of portions 744 and/or 774 during withdrawal of the components shown from the patient's body. Such stiffening elements may be incorporated as integral components of portions 744 and/or 774 and may, for example, comprise the same materials and design features of protector elements 746, 778 or may even be part of such protector elements.

Additional features, not shown, may also be incorporated into some embodiments, including those components shown in FIGS. 16, 17 and 18 of the present disclosure, to compress portions 744 and/or 774, and their components, for entry into a cavity such as a body cavity 30 and work in concert with protector elements 746 and/or 778. These features, similar to elements found in an umbrella, can include for example metallic or plastic snaps, hook and loop-type fasteners, zippers, or other mechanisms that may be released or activated by a physician or other user, manually or automatically, during deployment of portions 744 and 774.

FIG. 19 shows an embodiment of a system 100 of the present disclosure in which a cannula 770 as described above in connection with FIGS. 17-18 may be operated manually to effect cutting or morcellation of a tissue specimen by cutter 400. The embodiment of FIG. 19 illustrates one of several ways embodiments of the present inventions, and systems 100, may be configured. While the FIG. 19 embodiment shows manual operation of a version as described in connection with FIGS. 17-18, any of the embodiments, configurations, or component varieties contemplated by the present disclosure may be used with a manually operated cutting operation.

System 100 as shown in FIG. 19 includes a distal portion 110, proximal portion 120, cannula 770 integrated with guard elements, a tissue grasper or tenaculum 500, and a rotating cutter or morcellator 400. A container or bag 200 for tissue specimen 20 is not shown for purposes of illustrative clarity. On a proximal portion of 120 are disposed various control elements for operating the components described herein. A grabbing trigger 506 is operable by a physician or other user to open and close the teeth or jaws 512 of tissue grasper 500 and is disposed with grasper handle 504. A grasper axial trigger 506, which may include a ratcheting feature for ease and precision of use, may also be incorporated with grasper handle 504. In use, once grasper trigger 506 is operated to grab or hold at least a portion of tissue specimen 20 within teeth or jaws 510, the physician or other operator may activate axial trigger 506 to effect axial motion of grasper shaft 550 in a proximal direction to pull tissue specimen 20 towards cutter blade 408. This motion may be facilitated by a ratcheting mechanism (including spring 552 and other components not shown for clarity) to allow the physician or other user to move tissue specimen 20 in specific increments, as small as 1.0 mm or less (or greater if desired and as may be optionally selected by the physician or other user in some embodiments), during the procedure, to ensure reliable and safe operation.

It should be noted that although in FIG. 19 the embodiment described shows a handle 504 as being a part of tissue grasper 500, a handle of system 100 may be integrated as part of cannula 700, cutter 400, and still serve as a holding location for the physician or user to operate the various embodiments of system 100 as described herein. A handle may also be a separate component that is part of a system 100 but not incorporated as part of any given system component. As such, the labeling of handle 504 as part of grasper 500 is, while an embodiment of the systems described herein, is not meant to limit the location or configuration of a handle used in a more general sense to operate the systems described herein.

Disposed on the proximal portion 110 of the FIG. 19 system 100 embodiment is a component for manual operation of cutter 400. Here, a rotatable shaft 456 is disposed within a housing of system 100 and connected by a bevel gear system 458 (seen in schematic cross section in FIG. 19) to cutter 400. This shaft 456 is part of a hand crank 450 that also includes a handle 452 attached to wheel 454. Handle 452 and wheel 454 may be ergonomically optimized to facilitate ease of use; for instance, wheel 454 may have a platform-like surface on which the physician or other operator may rest his or her hand during a cranking maneuver to effect precision, minimize unwanted motion of system 100, and prevent operator fatigue. During the appropriate moment in the procedure as described variously herein, a physician or other operator may begin the tissue specimen cutting/processing step by rotating the cutter blade 408 by turning hand crank via the handle 452 and the relative motion of shaft 456 through bevel gear system 458. Of course, other versions of manually-powered embodiments, such as a moving foot pedal treadle system, ratcheting mechanisms, and the like, may be used in embodiments of the present disclosure instead of the hand crank 450 configuration as shown. The use of such a manual system as an alternative to an automated system or semi-automated system (both of which are also within the scope of the present disclosure) may afford greater control and precision when processing tissue specimens 20. Such a system may be of particular utility to cut through or otherwise process tissue specimens that are not homogeneous and that may have more dense or tough portions that require extra attention. Another advantage of the manual cutting system of FIG. 19 is that the physician or other operator may very readily reverse the direction of cutting, operate the cutter 400 in a "stop-start" fashion, etc. to maximize the effectiveness of the procedure. As discussed below, different embodiments of blade 408 that may be used with the present disclosure may be particularly amenable to use with a manually-operated cutter. It is within the scope of the present disclosure for other configurations of a manually operated cutter 400 to be utilized, and the particular configuration and components of the system as illustrated in the FIG. 19 embodiment should in no way be construed as limiting. For example, manually powered capability may be a feature of any of the components of system 100 disclosed herein, including combinations thereof (e.g., containers, manipulators, blades, guards, and their combinations etc. as may otherwise be described under the terms of power morcellation).

Figure 20:
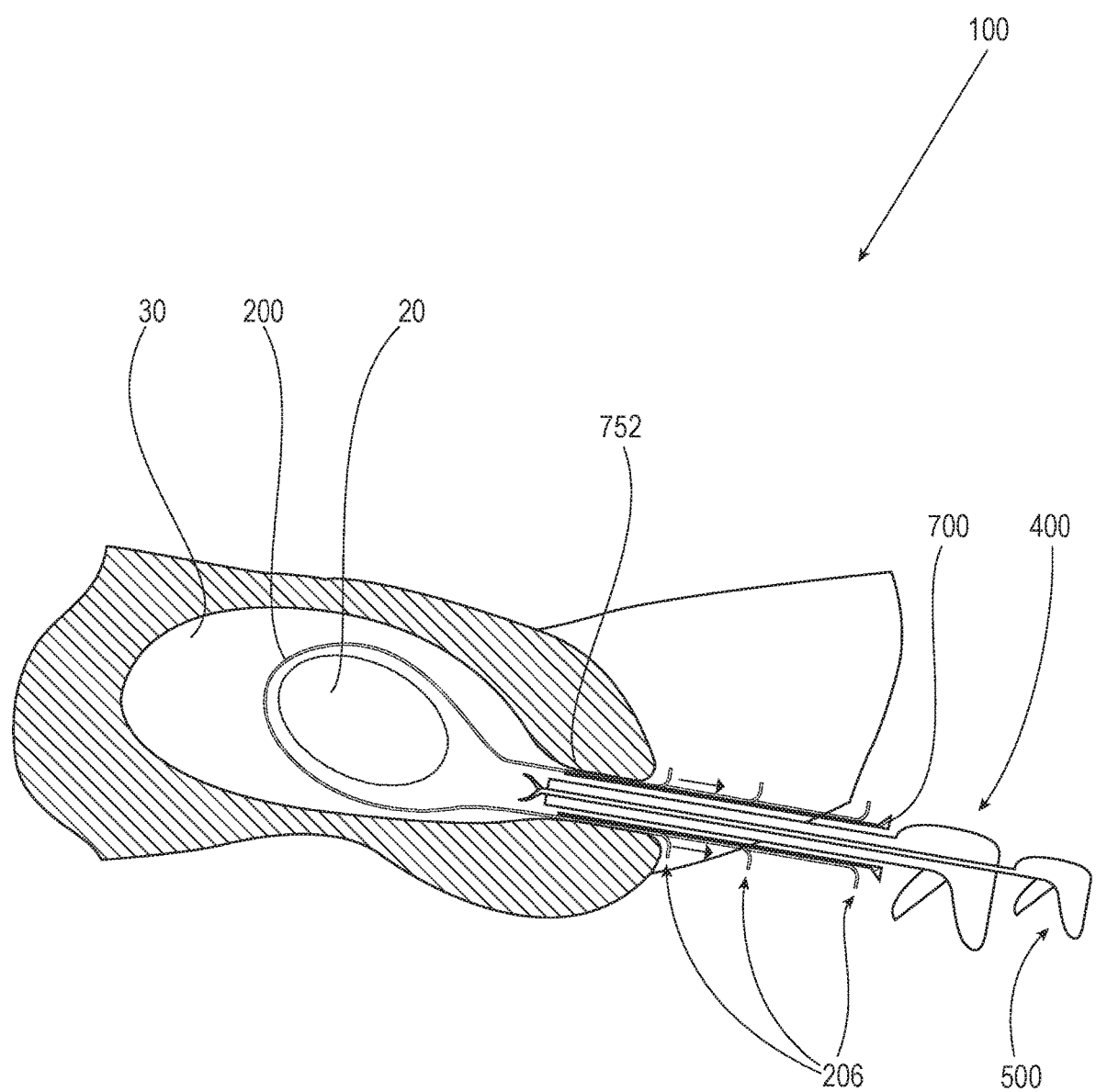
FIG. 20 depict a method of use of an embodiment of a system for tissue capture and removal including a pullback tensioning feature.

FIG. 20 schematically depicts an embodiment of system 100 illustrating a way that, in the context of a transvaginal procedure as described herein, advantageous tensioning may be effected without the necessity of rolling up or otherwise gathering the open end 206 of container 200 as tissue 20 is processed. In this example, the length of cannula 700, cutter/morcellator 400 and grasper or tenaculum 500 can be specified such that if container 200, with the specimen 20 therein, is pulled far enough towards the cannula distal end 752 that it would accommodate the distance required within the abdomen to pull the uterus or specimen 20 closer to the edge of the patient cavity 30 near the vaginal cuff and the desired zone of morcellation. This technique can be used instead of rolling up the container 200 as described elsewhere herein. Tension can be placed on the container 200 either by hand or with an apparatus (not shown) that controls the container tension. Container 200 may include one or more handles 292 (not shown) as described elsewhere herein, and such handles may be either permanently attached to bag 200 or may be affixed thereto during the procedure as the enclosure 200 is extracted from the patient's body. The embodiment shown in FIG. 20 may be configured for the same type of operation (no need to roll up container) in other, non-gynecological applications as discussed herein.

Figure 21:
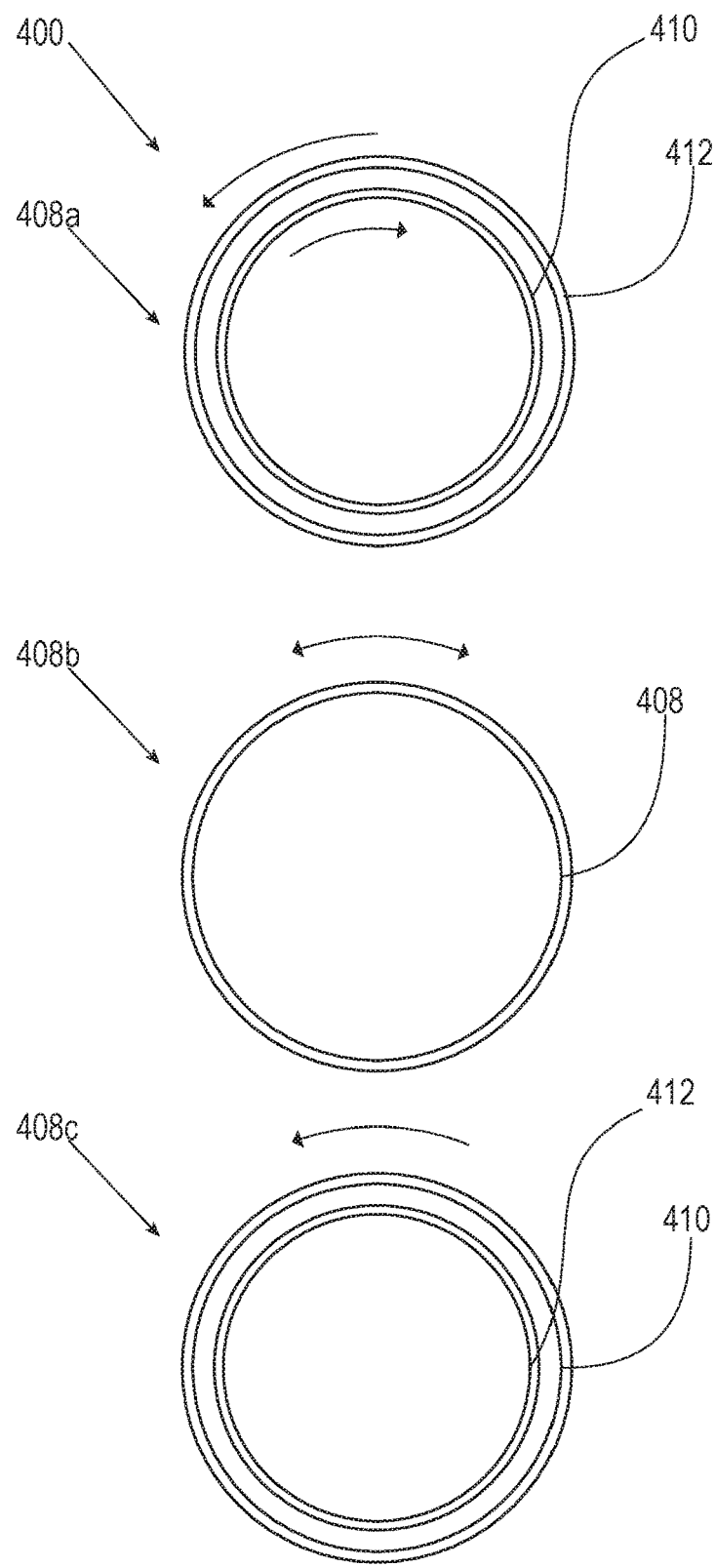
FIG. 21 depicts various views of cutter embodiments according to the present disclosure.

FIG. 21 depicts various views of cutter 400 embodiments that may be used in embodiments and methods of the present disclosure. Such cutter/morcellator 400 embodiments are described herein by way of example; other cutter embodiments, blade configurations, and designs may be used with systems and in methods of the present disclosure.

In the end-on view of cutter blade 408, cylindrical blade varieties 408a, 408b and 408c are shown in FIG. 21 in an end-on view. Blade 408a is an example of an opposing blade configuration in which an inner blade 410 component and an outer blade component 412 may be concentrically disposed and configured to rotate in opposite directions. The surface of such blade components 410, 412 may have different finishes, teeth types, or may be made of different materials to effect optimal cutting through what might be fibrous or difficult tissue within specimen 20, and may be particularly useful with a hand-operated cutting motion as described in connection with FIG. 19. Blade 408b is illustrative of a blade that can be operated in an oscillating or reversing rotational mode in addition to cutting in one direction only (all blade embodiments may be operated in unidirectional or oscillating modes). Blade 408b may be amenable to an automated and/or motor-driven cutter 400 to effect higher-rpm or oscillation frequencies for cutting through particular tissue types 20 of interest. Blade 408c is illustrative of a dual blade system in which one of blades 410, 412 is stationary during the cutter operation and one rotates as indicated. Such a blade configuration may assist the physician or user in having the cutter assist in obtaining greater purchase of tissue during the cutting process for a more stable and reliable operation, as the stationary blade can penetrate the tissue upon the application of axial force into the tissue as the other blade rotates to process the tissue. In all blade 408 embodiments of the present disclosure, the edge may be serrated, smooth, or have other features to optimize the cutting of tissue as described herein. The blade 408 may be equipped with additional capability, such as radio frequency (RF) energy application, to assist in the cutting operation (or alternatively other components of the systems herein may include a dedicated and separate RF tool). If RF energy is used on blade 408, it may be unnecessary to use rotational motion for blade 408 to cut through tissue. And although blades 408a, 408b and 408c are shown at the end of a cutter 400 in the form of a standard right cylinder so that its cross-sectional shape is that of a circle, cutter 400 and/or blade 408 may take on other shapes as appropriate, including those that have cross-sections representing a crescent, semi-circle, irregular, etc., with or without RF-energy supplementation.

Another embodiment of a cutter blade 408 (not shown) involves a cylindrical structure similar to that of 408b but contains within its inner volume a rotating and/or oscillating blade, perhaps triangular in shape, that moves within the structure's inner volume to axially exit its distal end and cut tissue as it rotates. Such a blade may be an integral part of or attached to a second cylinder concentrically disposed within the first cylindrical structure's inner volume; the second cylinder serves as a carrier for the liner/triangular blade or blades of which the second cylinder is a part.

Other cutter 400 embodiments are within the scope of the present disclosure, including those that utilize optical (e.g., laser), vibrational, fluid (e.g., hydro-jet), or other modalities, singly or in combination with one another or with any of the means described above, to cut tissue as known to those of skill in the art.

Figure 22A:
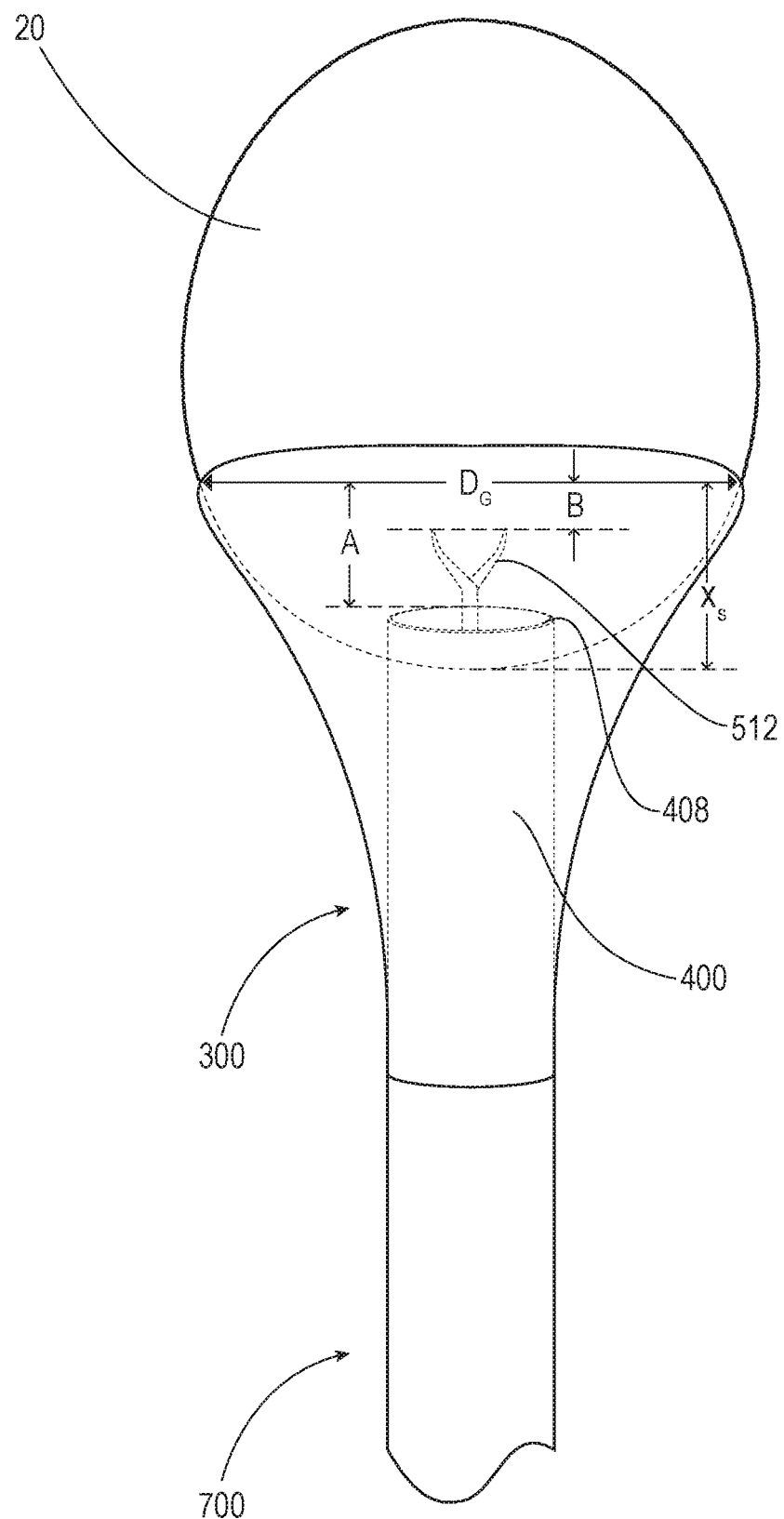
FIGS. 22A-B illustrate in schematic form various dimensional relationships among tissue components of a system of tissue capture and removal.
Figure 22B:
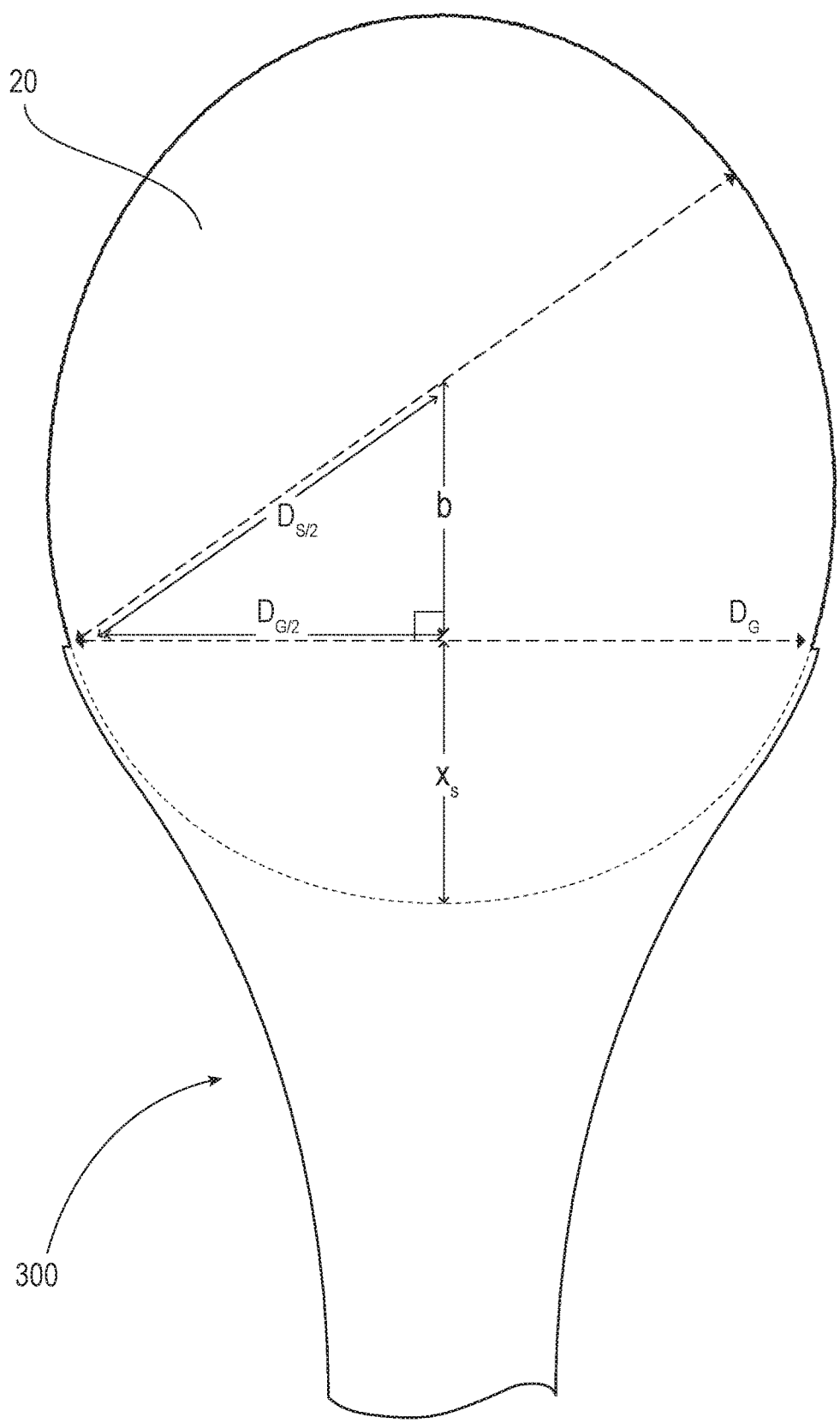

FIGS. 22A-B illustrate nondimensionalized spatial relationships useful in configuring systems and methods of the present disclosure so to help ensure an optimal clinical outcome. In these schematics, a cannula 700 distal end 752 is seen having a guard 300 integrated with or attached thereto such that the guard flares out to a maximum diameter. This is shown in FIG. 22A as plane $D_G$. Tissue specimen 20 is shown in apposition to cannula distal end 752 and partially within the volume created by cannula distal end 752 to a depth $x_s$. Specimen 20 has a maximum diameter $D_S$. A distal portion 510 of tissue grasper or tenaculum 500, showing jaws 512, is seen extending out of cutter central lumen 402 in the vicinity of blade 408 and generally in alignment with the central axes of cannula 700 and cutter 400. The symbol A in FIG. 22 represents a distance between a line representing a plane of the guard at its maximum diameter $D_G$ and the distal extent of cutter 400 at blade 408. The symbol B in FIG. 22 represents a distance between a line representing a plane of the guard at its maximum diameter $D_G$ and a distal end 548 of grasper 500 at jaws 512. $D_G$ can be specified so that it matches the size of specimen 20 and so that it controls $x_s$, the depth of the specimen into the guard as measured from the line at $D_G$. In one embodiment, both distances A and B are less than $x_s$. Such an embodiment helps to ensure the specimen 20, which is relatively large compared to the guard 300, comes into contact with both the cutter 400 (particularly blade 408) and tissue grasper 500.

FIG. 22B in turn exhibits how such parameters may be idealized to solve for a specimen depth $x_s$. A right triangle is shown having sides $D_G/2$ and b, and a hypotenuse $D_S/2$.

The Pythagorean theorem posits the sum of the squares of the two sides of a right triangle equals the square of the triangle's hypotenuse. In this context:

$$\left(\frac{D_G}{2}\right)^2 + b^2 = \left(\frac{D_S}{2}\right)^2$$

In FIG. 22, specimen depth $x_s$ is represented by $$x_s = \frac{D_S}{2} - b$$

such that $$b = \sqrt{\left(\frac{D_S}{2}\right)^2 - \left(\frac{D_G}{2}\right)^2}$$

And thus one can solve for specimen depth $x_s$ by:

$$x_S = \frac{D_S}{2} - \sqrt{\left(\frac{D_S}{2}\right)^2 - \left(\frac{D_G}{2}\right)^2}$$

Therefore, one may calculate specimen depth $x_s$, knowing that an ideal solution involves a specimen depth being less than dimensions A and B in FIG. 22A, by designing the maximum diameter $D_G$ of guard 300 relative to the maximum diameter $D_S$ of tissue specimen 20 expected to be used therewith.

As shown in the idealized way in FIGS. 22A-B, the symmetric cone afforded by guard 300 and how specimen 20 lines up therewith would result in a "coring" type of specimen cutting as opposed to the "peeling" type of specimen cutting as described herein in connection with the embodiments of FIGS. 17-19. Therefore, these spatial relationships can be calculated in the context of a non-symmetrical conical guard protector portion where a tangent to the tissue specimen 20 surface 20a is placed at the blade 408. In any configuration, however, the desire for the dimensions of a cone-shaped guard component to allow for a relatively large tissue specimen to come into contact with the cutter 400 and grasper 500—components that are not designed to protrude beyond the opening of the guard—dictates ideal dimensions of the guard cone. It is also contemplated that because either or both of cutter 400 and grasper 500 may also be usefully disposed, even if only for a brief moment during use, above the line representing a plane of the guard at its maximum diameter $D_G$, the distances A and B may have negative values relative to $D_G$.

Exemplary Methods of Use

FIGS. 23A-F illustrate a method of use of the systems 100 of the present disclosure. It is presented as a method of performing a transvaginal procedure, such as a hysterectomy, but the techniques detailed herein may be used elsewhere in the body without departing from the spirit of the embodiments disclosed herein.

Figure 23A:
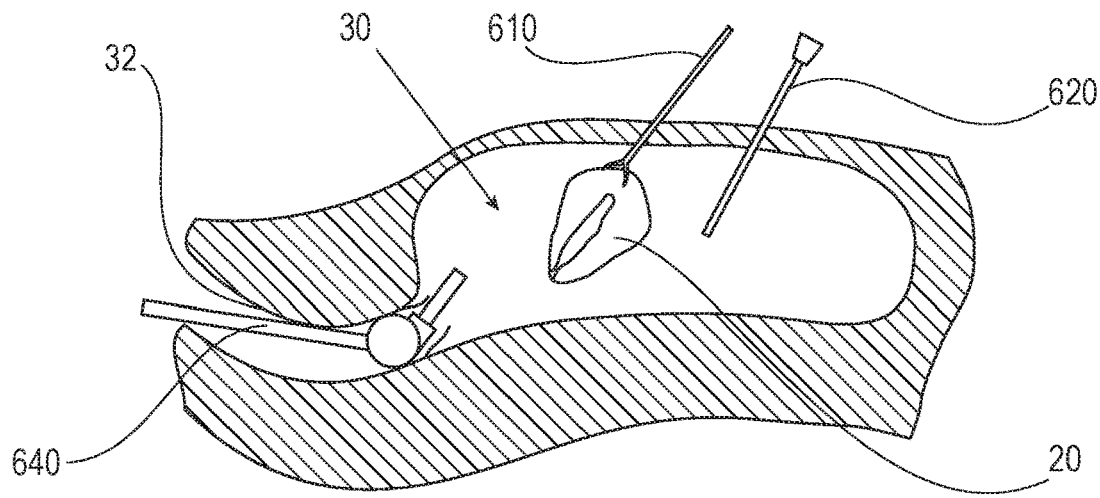
FIGS. 23A-F illustrate a method of use of a system of tissue capture and removal.

Prior to the steps outlined below in connection with FIGS. 23A-F, a physician or surgeon will prepare a patient by using known techniques to prepare the tissue specimen 20, which in this example may contain a uterus and possibly other tissue and organs (such as one or both ovaries, fallopian tubes, connective tissue, etc.), for removal from the body. As known by those of skill in the art, this may be performed via any number of approaches, such as, e.g., by performing a minimally invasive hysterectomy, perhaps robotically, through the use of standard laparoscopic instruments. This is schematically represented in FIG. 23A: one of any number of laparoscopic instruments 610, which may involve a tissue manipulator, cutter, or similar tool, has gained access via a surgically-created port to a patient's pelvic cavity 30. Cavity 30 may be insufflated using known techniques to create working and visualization space in cavity 30 via, e.g., insufflation instruments delivered through one or more ports in the patient's body. A laparoscope 612 is shown accessing cavity 30 by a second surgically-created port to allow the surgeon to visualize the procedure and his or her use of the tools. A uterine manipulator 640 (such as the VCARE DX uterine manipulator sold by ConMed Corporation of Utica, N.Y.) is shown disposed in the patient's vagina 32. At the moment in time represented by the schematic of FIG. 23A, tissue specimen in the form of a uterus 20 has been excised from its connective tissue, including the level of the cervix, and is being held in the pelvic cavity 30 by instrument 610. A distal end of the uterine manipulator 640 may have been utilized to assist in the process of preparing the uterus 20 for removal as known by those of skill in the art. For ease of illustration, other tissue such as one or both ovaries, the fallopian tubes, and other tissue intended for removal are not shown but may be considered part of the tissue specimen 20 referred to and shown herein as uterus 20.

Figure 23B:
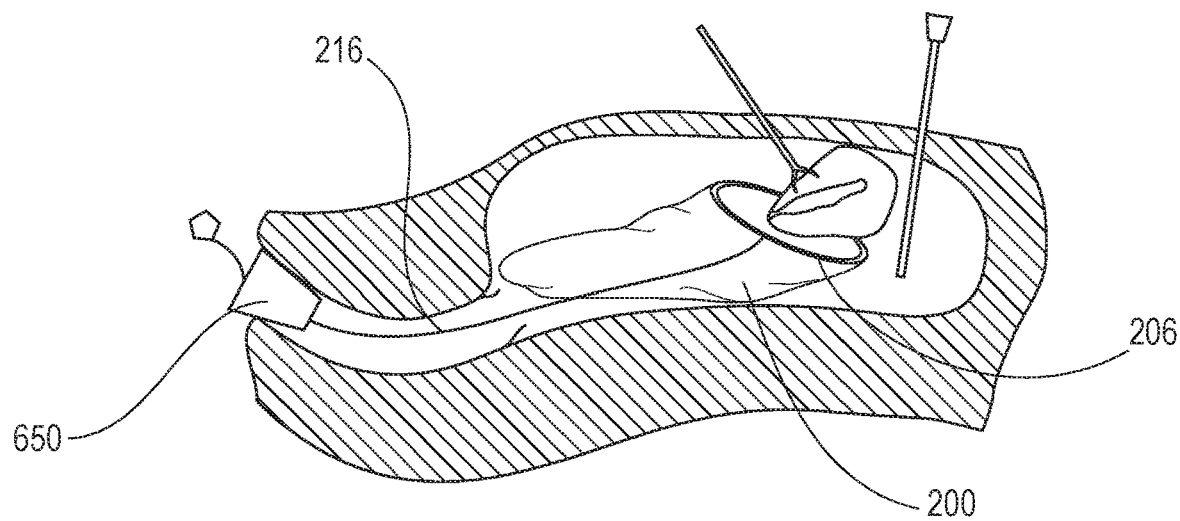

FIG. 23B shows a transvaginal insertion of bag or enclosure 200 into the vaginal opening, through the vagina 32 and into pelvic cavity 30. Uterine manipulator 640 has been retracted and removed from the body through the vagina. A tether, drawstring, or other element 216 is shown extending through the vagina 32 and out of the vaginal opening 34 to provide for manipulation of container 200 by the physician or other user. Tether or element 216 may be flexible or may have a stiffer construction, in particular in its column stiffness, to facilitate optimal container manipulation. Uterus 20 is shown being captured by container 200 and placed into an interior 204 by the assistance of tool 610.

Occluder 650, and as shown, vaginal occluder 650, can then be place in vagina 32 as shown in FIG. 23B, with tether 216 optionally extending therethrough, to establish/reestablish and maintain insufflation of cavity 30 as known to those of skill in the art through, e.g., the introduction of a gas such as carbon dioxide through one of the surgically-created ports in the pelvic or abdominal cavity 30. In other embodiments, a high flow insufflator may be used to maintain insufflation of cavity 30 even as gas escapes through the vaginal canal, without use of an occluder or other means, due to the higher gas flow rates it affords.

Generally, occluder 650 may be placed trans-vaginally, trans-pelvically, or via any other body orifice or surgical incision, and may be in a variety of lengths (for example, between about 30.0 mm or less and about 300 mm or more, including up to approximately 1,000 mm or more) and diameters (for example, between about 10.0 mm and about 80.0 mm) to accommodate a variety of surgical or natural openings or ports. In some embodiments, occluder 650 provides a snug fit against the walls of the opening or port into which it is disposed, optionally through the use of a seal, and by choosing the appropriate size. When a snug fit between occluder 650 and the opening or port is accomplished, fluid leakage around an outer diameter of sheath may be minimized or even eliminated. This may be useful when it is desirable to achieve and/or maintain pneumo insufflation of a body cavity 30 containing specimen 20 to be captured and removed. Occluder 650 may contain a central lumen through which other instruments may be disposed or deployed, such as tether, drawstring or similar instrument 216, a tissue cutter 400, a tissue grasper or tenaculum 500, or the like. Occluder 650 may include a blade guard to protect healthy tissues as well as the container 200 from accidental damage.

Figure 23C:
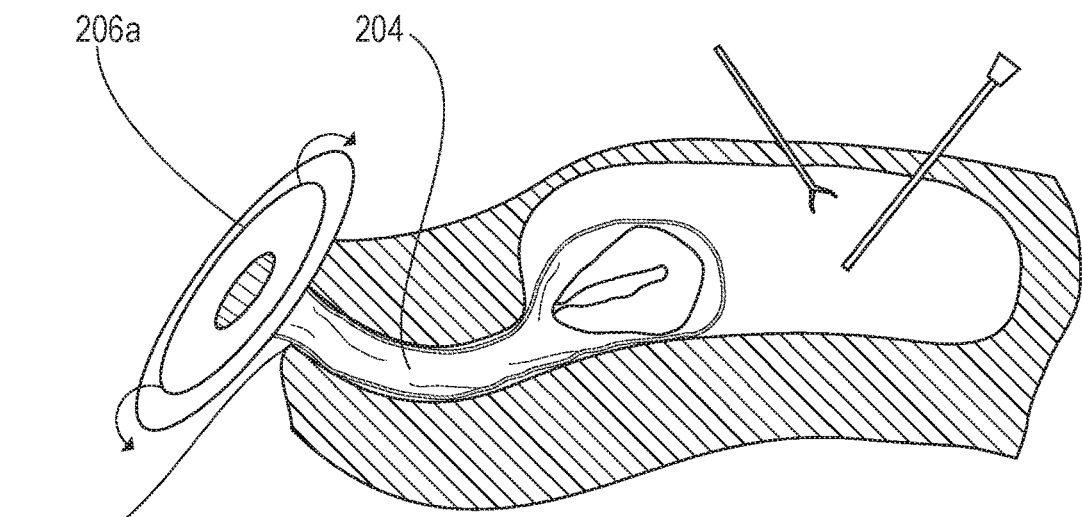

In FIG. 23C, the physician or other operator uses tools such as tether 216 and possibly tool 610 to manipulate container 200 with specimen 20 placed therein so that container opening 206 defined by container edge 206A is pulled through the vagina 32 and out the vaginal opening 34. Container may next be tensioned using various techniques as described herein to pull the uterus 20 near or even against the vaginal cuff within pelvic cavity 30. FIG. 23C depicts container 200 now oriented such that the opening 206 is outside the patient's body. Container edge 206a may be rolled in on itself in the direction shown to foreshorten container 200, effecting the aforementioned tension to bring uterus 20 in abutment with, adjacent to, or at least closer to the patient's vaginal cuff in the pelvic cavity 30. Instruments 610 and 612 may remain in their ports as shown to assist the physician or other user in completing the procedure.

Depending on the type of insufflation that may be used during this exemplary procedure, container 200 as tensioned and put into apposition against the vaginal wall at opening 34 may rapidly or even instantaneously produce an adequate seal against fluid, including insufflation gas, from leaking out through the vaginal canal and opening 34. As such, any plug used to reestablish insufflation as described above, including occluder 650, may then be removed from the patient's body. In some embodiments occluder 650 may be expelled from opening 34 simply by the action of the physician or other operator pulling container edge 206a and opening 206 out of the patient's body through vagina 32 and opening 34. This placement of container 200 as shown in FIG. 23C allows for insufflation (or re-insufflation) of the pelvic cavity 30 to provide an optimal viewing and working environment for the physician or other user to complete the exemplary procedure, perform necessary suturing, tissue cauterization, etc., without the need of additional tools.

Figure 23D:
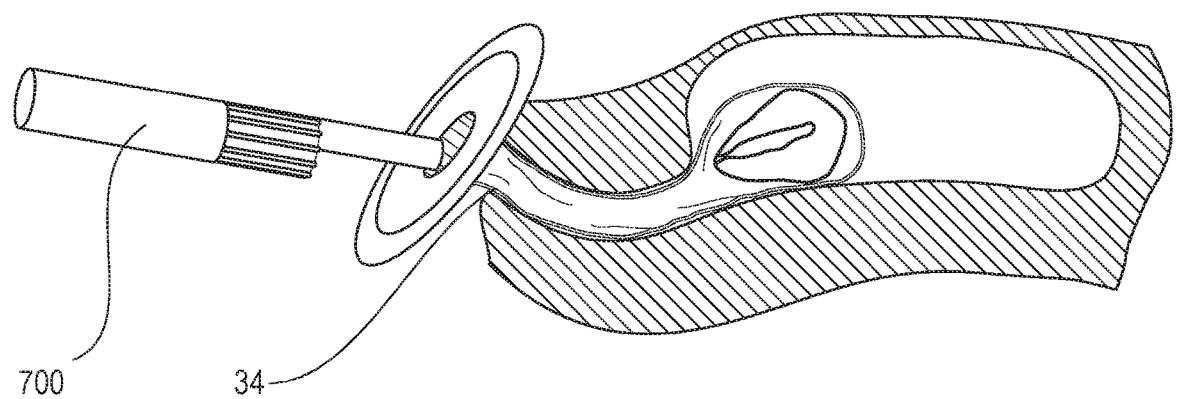
Figure 23E:
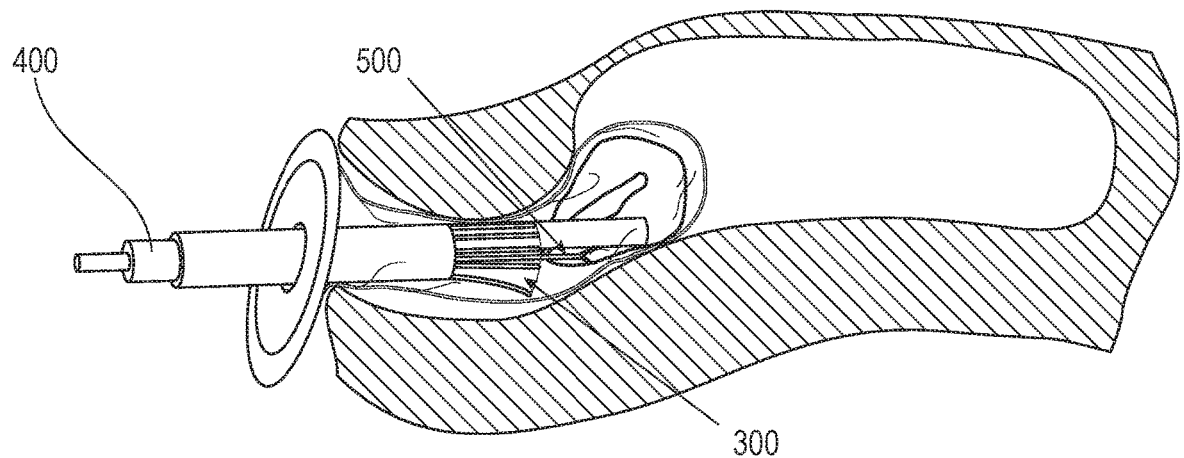
Figure 23F:
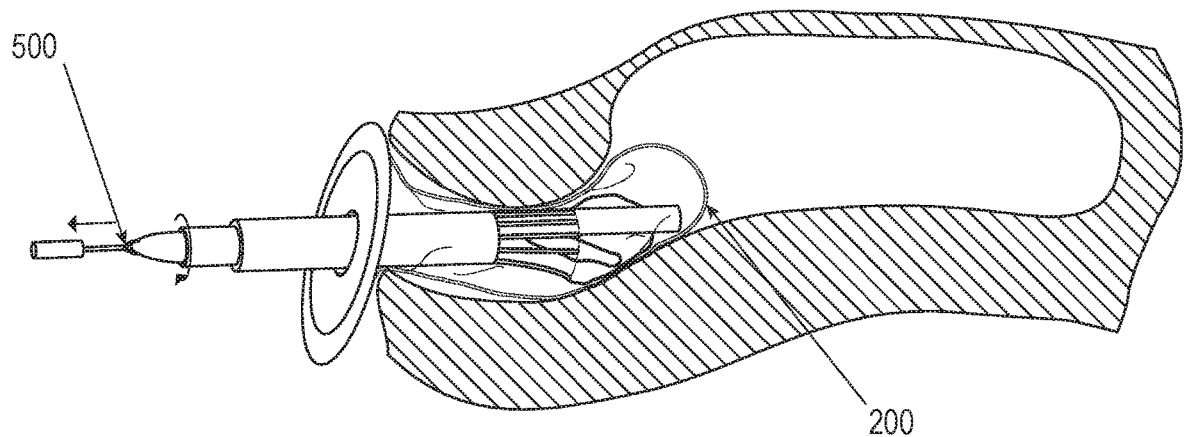

Turning to FIGS. 23D-F, a cutter/morcellator 400 is shown accessing the interior 204 of enclosure 200 through cannula 700 while proper tensioning is maintained on container 200 to keep uterus 20 in position for removal. Any guard 300 or protector structure elements, such as those described herein, whether integrally forming a cannula protector portion 744 or attached to cannula at its distal end 752. Cannula 700 has been inserted into the patient's vagina through opening 34, via interior 204 of the previously-placed container 200, either first or simultaneously with cutter 400. Any guard 300 or protector feature present may expand against the vaginal wall near the vaginal cuff in the vicinity of cavity 30, or wholly within cavity 30, to facilitate insufflation if needed. FIG. 23E shown distal portions 752, 548 of cannula 700 and cutter 400, respectively, approaching uterus 20. Instruments 610, 612 are not shown for clarity of illustration but may be utilized at any time to aid in positioning uterus 20 as needed. Extension 776 of the cannula embodiment 770 is shown in FIG. 23E as disposed within bag interior 206 and adjacent uterus 20 so to preferentially facilitate bringing the uterus into the gap 788 created between cutter distal end 548 and extension 776 as described in connection with the embodiment 770 of cannula described herein with reference to FIGS. 17-19. It should be noted that other cannula embodiments described herein, including without limitation cannula 740, may be used in the procedure described in connection with FIGS. 23A-F as well as other procedures and methods of the present disclosure.

FIG. 23E also shows a tissue grasper or tenaculum 500 being disposed in the central lumen 402 of cutter 400 so that Such a grasper 500 may be a custom, heavy duty tool, or one of many commercially available to physicians. Grasper gripping elements or jaws 510 grasps a portion of uterus 20 and the operator may retract grasper axially and/or maintain axial tension on grasper 500 to bring uterus 20 closer to cutter blade 408, and the cutter may be then activated after or during this tension being applied through grasper 500 to cut uterus 20. As cutter 400 is operated, either manually or automatically as described herein, the physician or user may continue to apply tension to container 200 and axial tension on grasper 500 to keep uterus 20 in contact with blade 408. Uterine tissue 20 will be cut/morcellated to the extent that the rotating cutting action in connection with the applied tension, pulls the tissue through lumen 402 of cutter and out of the patient's body at a proximal portion 422. This may be accomplished relatively quickly. During this tissue cutting and removal process, guard 300 or features such as protector elements 746, 778, enclosing element 780 and extension 776 described elsewhere herein serve to protect container 200 from damage, aiding the function of enclosure 200 in the present disclosure to fully contain the tissue specimen 20, including any cancerous or pre-cancerous cells associated therewith, and keep such tissue from being left in the pelvic cavity 30, vagina 32, surgical ports, etc. in undesirable fashion.

After uterus 20 is processed as described above and when tissue specimen 20 is or has become by virtue of the cutting action of cutter 400 small enough to be removed from the patient's body, cutter 400 and cannula 700 may be withdrawn from the interior 206 of container 200. Simultaneously with or after the withdrawal of cutter 400 and cannula 700, container 200 may be pulled in its entirety out of the patient's body through vagina 32 and vaginal opening 34. The procedure may then be completed with routine suturing, cauterization, etc. as necessary.

One advantage of the transvaginal approaches described herein, including the method described in connection with FIGS. 23A-F, is that by processing tissue within container 200 but through the vagina 32, less cutting is necessary. Morcellating or processing tissue using other techniques, such as by a surgical incision (i.e. a "mini-laparotomy") or by use of a PNEUMOLINER sold by Olympus America, Inc., can require an incision on the order of about 5 cm or greater in size. In comparison, transvaginal removal of tissue does not require as much morcellation or tissue processing/cutting, as the vagina is a relatively large, flexible port, naturally occurring. Moreover, minimal cutting/processing of tissue specimens 20, such as the uterus 20, presents a faster process as the tissue need be morcellated only to the extent that it can be readily removed through the vagina. Larger, less processed portions of the tissue sample removed via these techniques may be more attractive to pathologists studying the tissue specimen 20 as the larger portions are likely to have suffered less violence as they are removed.

Figure 24A:
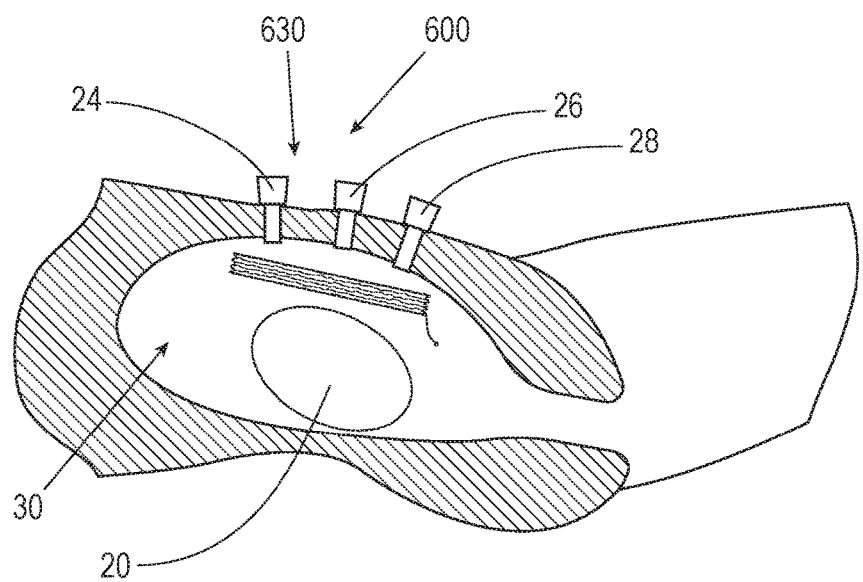
FIGS. 24A-F illustrate another method of use of another system of tissue capture and removal.
Figure 24B:
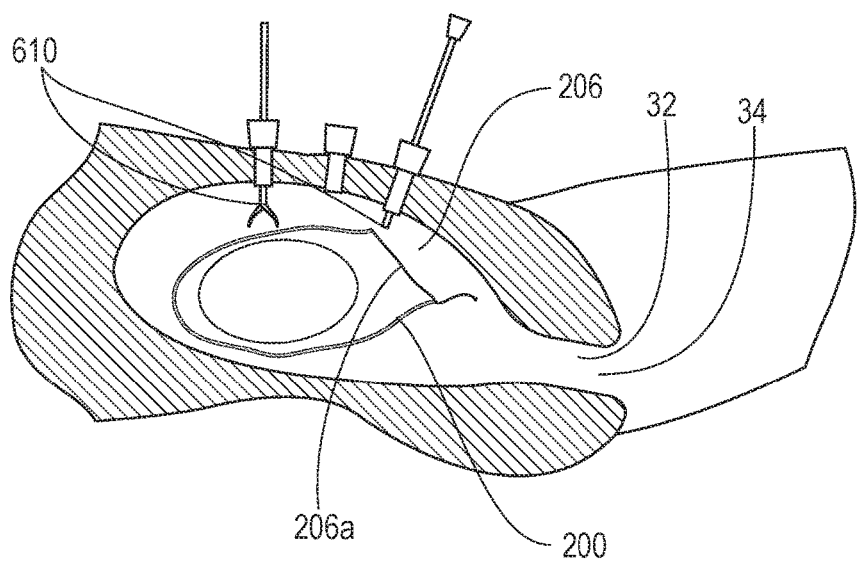
Figure 24C:
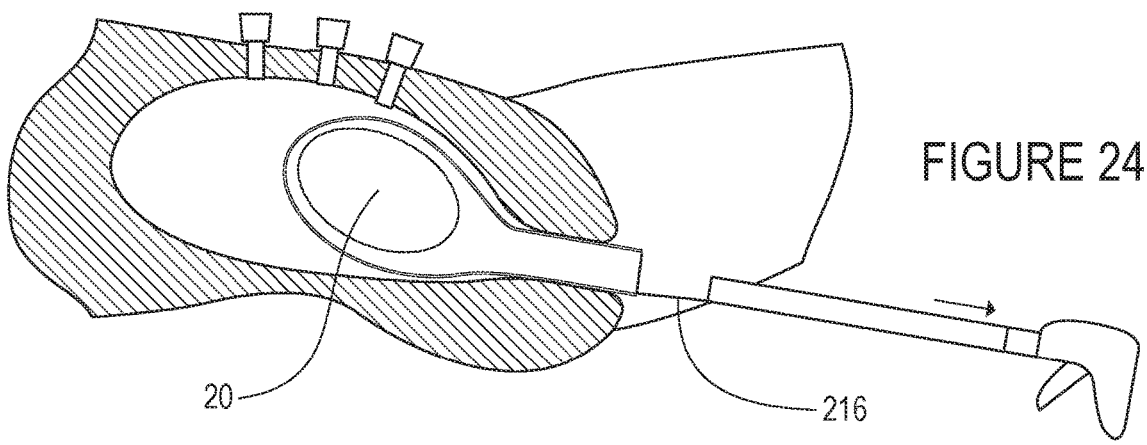
Figure 24D:
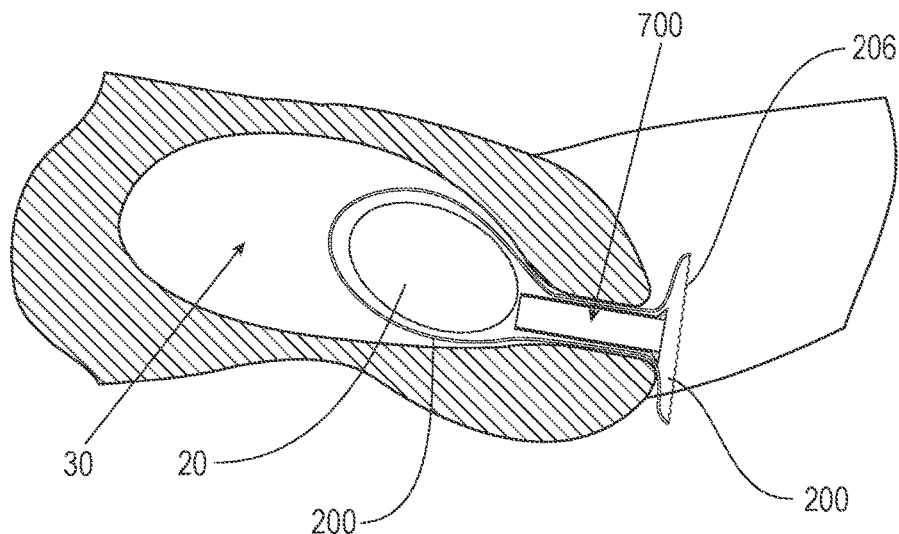

Another transvaginal method of use is shown in connection with FIGS. 24A-F. In this embodiment, laparoscopic techniques are utilized and the uterus 20 is detached using traditional methods. A collapsible containment device or bag 200 is then introduced into the patient's pelvic cavity 30 through the vagina 32, through one of ports 24, 26 or 28 as shown in FIG. 24A, or through a small abdominal incision such as a port site with the port momentarily removed. The physician or other user places specimen 20 into the container interior 206 through the help of a robot and/or with instruments such as instrument 610, 612 that are guided through the abdominal ports 22 or instruments guiding through the vagina 32. An end of container containing opening 206 is then pulled out by the physician or other operator through the vagina (or other port) with an instrument such as, e.g., a grasper 500 pulling on tether 216 connected to container 200 as shown in FIG. 24C. In this embodiment, a cannula 700 is next introduced into the vagina 32 as shown in FIG. 24D. Cannula 700 may be of the appropriate diameter and length for the patient being treated, and serves to create a smooth working channel for the cutter/morcellation equipment 400. An optional guard 300 (not shown) or a cannula equipped with protective features described herein may also be used to help guide the tissue specimen 20 into the cutter 400 and to protect the enclosure 200 from being damaged. Such protective features may also be part of the cutter 400 and/or tissue grasper 500.

Figure 24E:
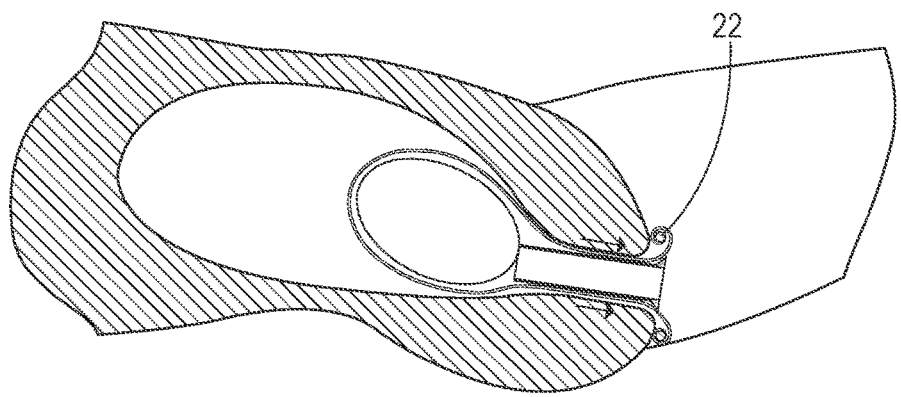

FIG. 24E shows that by pulling edge 206a of container with respect to the cannula in a proximal direction away from pelvic cavity 30, which may be done prior to insertion of cannula 700, during or after insertion of cannula 700, the physician or other operator can concomitantly draw the specimen 20 closer to or against the vaginal cuff, and when cannula 700 is in place, near or against cannula distal end 752 (and if in place, blade 408 of cutter 400) while also providing the desired tension for tissue cutting as described elsewhere herein. As described below, an optional ring 294 can be placed on container edge 206a to aid the physician or other user in this step or other tensioning techniques and equipment as described elsewhere herein may be employed. Cutter/morcellator 400 is placed through cannula lumen 702, either simultaneously with the introduction of cannula 700 or afterwards, so that the uterus or specimen 20 can be morcellated. Tissue grasper or tenaculum 500 is shown disposed through cutter lumen 402 for grasping uterus 20 to align it with cutter blade 408 and for applying additional tension to facilitate specimen processing.

An optional ring or rolling device 294 can be placed or inserted on or integral with the edge 206a of container 200 to aid the physician or other user in the step of pulling on container 200 to bring specimen 20 closer to cannula distal end 752. In FIG. 24E ring 294 is seen rolled towards the container interior 204 or towards an exterior of container 200. Rolling device is represented in FIG. 24 as a toroid having a circular cross section; however, other geometric shapes can be used to bunch, wrap or wind container 200 to create any desired tension.

In addition to the use of various protective features as described herein either as a guard 300 or protective features on cannula 700 and/or cutter, application by the physician or other user of tension on container 200 can prevent the container from being drawn towards the blade 408, avoiding damage to container 200. Other features such as, e.g., mechanical stops 753, detents, pins, notches, or other mechanisms can be used to position the edge of cutter/morcellator blade 408 precisely relative to the cannula distal end 752. Cutter blade 408 can be positioned within about 3.0 mm to about 5.0 mm of the cannula distal tip 752; alternatively, cutter blade 408 can be positioned within about 0.0 mm to about 50.0 mm of cannula distal tip 752. Additionally, after it is advanced through the cannula lumen 702, blade 408 may be positioned within about 3.0 mm to about 5.0 mm from the cannula distal tip 752 or within about 0.0 mm and about 50.0 mm from the cannula distal tip 752. There can also be a precise spatial-axial or radial-relationship between the grasper 500 and the cutter blade 408 as well as between the tenaculum 500, including jaws 512, and the cannula distal end 752. For example, a maximum distance between the far reach of the tenaculum grips 512 and the blade 408 could be about 10.0 mm, but could range from about 0.0 mm to about 250.0 mm. The maximum distance between the maximum reach of the tissue grasper/tenaculum grips 512 and the end of the cannula could be between about 0.00 mm and about 5.0 mm, but could range from about 0.0 mm to about 250.0 mm.

Figure 24F:
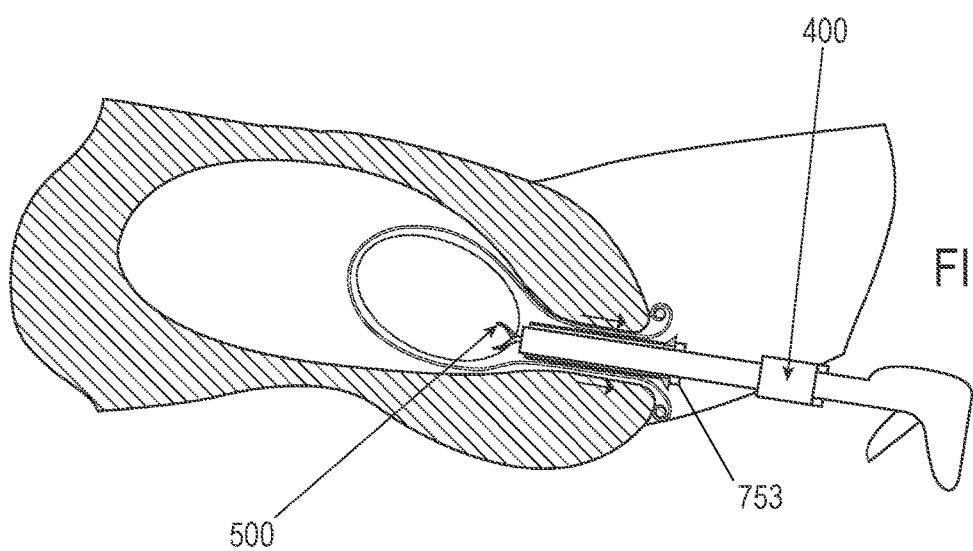

As cutting/morcellation progresses according to this method, portions of tissue specimen 20 will be transported through the cannula central lumen 702 and out of the patient's body; in this case, the vagina 32. During the cutting process, the uterus 20 is enclosed safely within bag interior 204 to achieve the objectives described herein. FIG. 24F illustrates that morcellation only needs to be performed until the uterus 20 is small enough to be pulled out of the port, in this example, vagina 32 and vaginal opening 34. Once cutting and tissue specimen 20 removal is complete, cutter 400, tenaculum 500, and container 200 may be removed from the patient's body and the procedure may be completed as described herein.

Figure 25A:
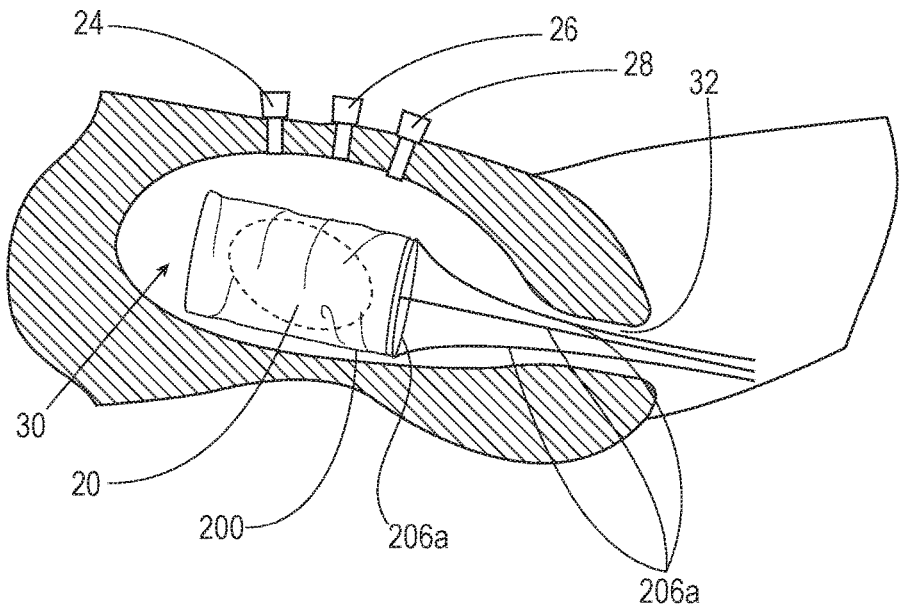
FIGS. 25A-C illustrate yet another method of use of a further system of tissue capture and removal.
Figure 25B:
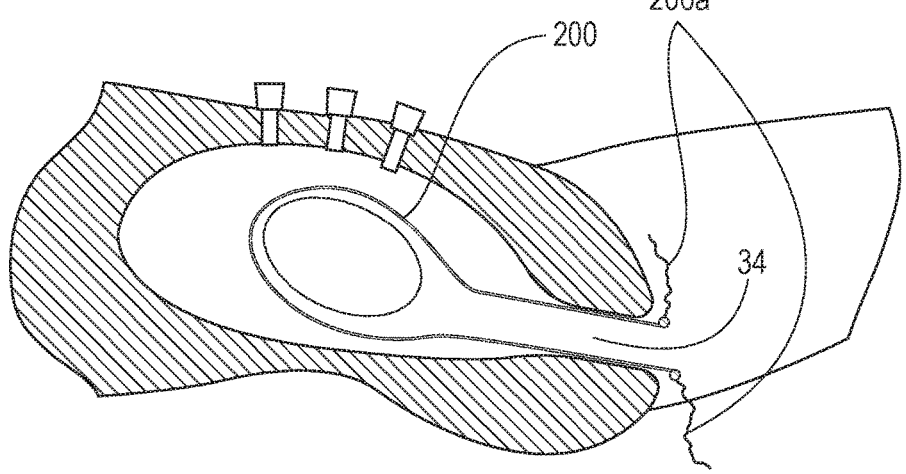
Figure 25C:
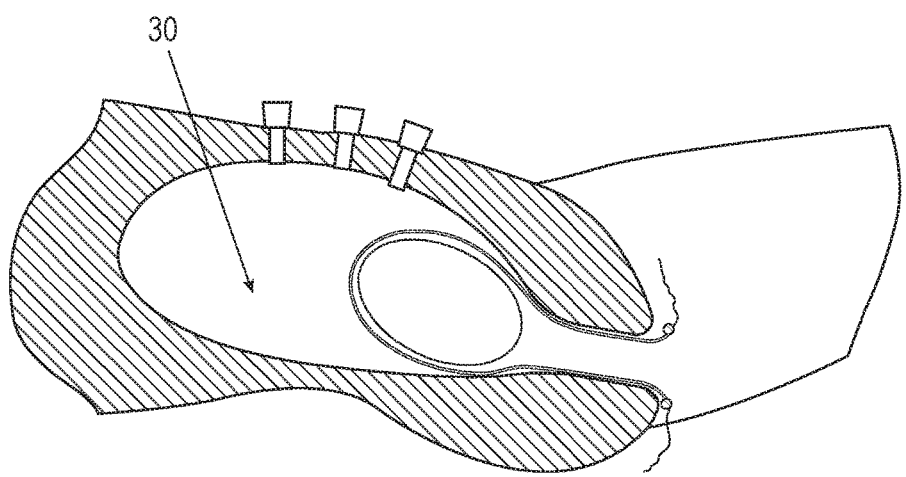

FIGS. 25A-C depict another method of using the various systems and components of the present disclosure in a hysterectomy context. As with the embodiments of FIGS. 23-24, standard techniques may be used to access and detach uterus 20 from within the pelvic cavity 30, and the techniques described herein may be used to deploy container 200, capture tissue specimen/uterus 20 within the container interior 204, optionally employ cannula 700 and/or tissue grasper 500 and employ cutter 400 to cut and process uterus 20 and remove it through the vagina 32 as previously described. In the embodiment of FIGS. 25A-C, however, bag 200 contains multiple tethers, strings or flexible wires 216 attached to or incorporated as part of container distal end 255 near opening 206. Three such tethers 216 are shown in FIGS. 25A-C as extending through the vagina 32 out through the vaginal opening 34 and assist the physician or other user in entrapping and capturing specimen 20, particularly if instruments 610 deployed from surgical ports are of little help. As with other systems and methods described herein, the physician or other user prepares the tissue specimen 20, in this case uterus 20, using standard techniques; typically laparoscopic and/or robotic using tools 610 and/or scopes 612. Container 200, which may be stored in compact form (e.g., in a collapsed, accordion-like configuration or rolled to a small diameter sufficient for deployment through a port) is deployed into the patient's pelvic cavity 30 either through the vagina 32 or via another port, such as one surgically created in the pelvic wall. Alternatively, small members made, e.g., of plastic or thin cloth (not shown) can be included so to aid in maintaining container 200 in a compact or collapsed position. These members or ties may be engineered to break or detach under sufficient force applied on the tethers or strings 216 so to fully deploy enclosure 200 for specimen capture.

Next, the physician or other user, via one or more of tethers 216 and/or tools 610, 612 and optionally via tools introduced transvaginally (not shown) or laparoscopically, unfurls or opens container 200 captures uterus 20 and places it into container interior 204 through opening 206. FIG. 25A depicts the uterus 20 captured wholly within container interior 204 and all three tethers 216 leading out of cavity 30, through vagina 32 and out of the patient's body via vaginal opening 34. If, e.g., container 200 happens to be positioned on the opposite side of the specimen 20 from the vaginal port, the multiple strings or tethers—anywhere from about two to about 10 or more—may be utilized by the physician or other user to help capture specimen 20 within container interior 204. FIGS. 25A-B show how and then container edge 206a may be drawn towards the vaginal cuff, pulling container 200 and captured uterus 20 along by the physician or other user pulling or tensioning the ends of the strings/tethers 216; this in turn tensions container as described elsewhere. At this point, the specimen 20 may be cut/morcellated/processed and removed via the techniques described herein via use of cutter 400 and optionally grasper 500, and container 200 may be removed from the vagina 32 through opening 34 and routine items may be attended to in order to complete the procedure.

Rather than being flexible or string-like, one or more of tethers 216 in the embodiment shown in FIGS. 25A-C or any of the others described herein may be relatively stiff or wire-like. This embodiment can aid the physician or other operator in the step of capturing specimen 20 with less or even no assistance from additional ports, such as ports in the example of FIGS. 25A-C created in the patient's pelvic wall through which one or more tools 610 or scopes 612 may be deployed. In one mode of operation, for example, relatively stiff guides 216 enable the physician or other operator, working with guides 216 as deployed through a natural port such as vagina 32, to place the container 200 on a distalmost or far side of the uterus relative to the vaginal cuff, by placing the uterus 20 directly between the container 200 and the vaginal cuff at the former location of the cervix in the pelvic cavity 30. Once enclosure 200 is properly situated, these relatively stiff members 216 can be pulled in an axial direction out of the patient's body by the physician or other user, and the uterus 20 can be captured, pulled towards and even against the vaginal cuff within container interior 204 and processed or morcellated as described elsewhere herein.

Figure 26A:
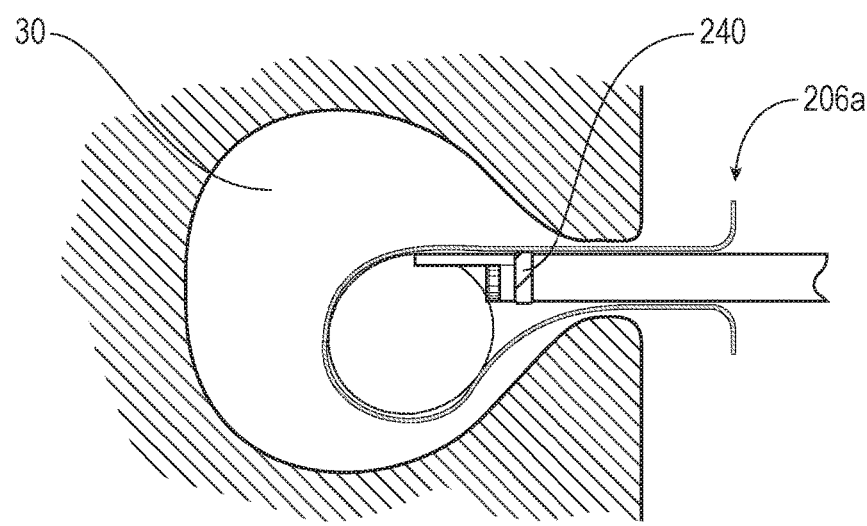
FIGS. 26A-D schematically depict another embodiment of the present disclosure and method of use.
Figure 26B:
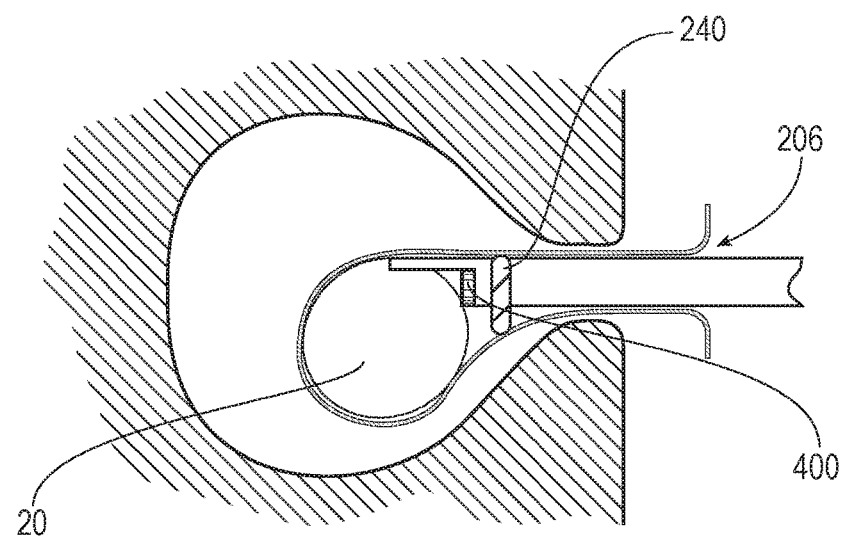
Figure 26C:
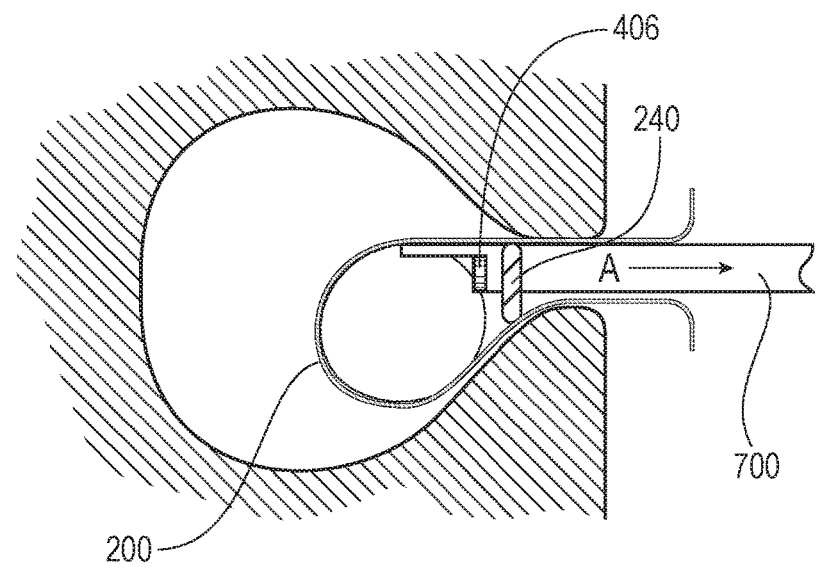
Figure 26D:
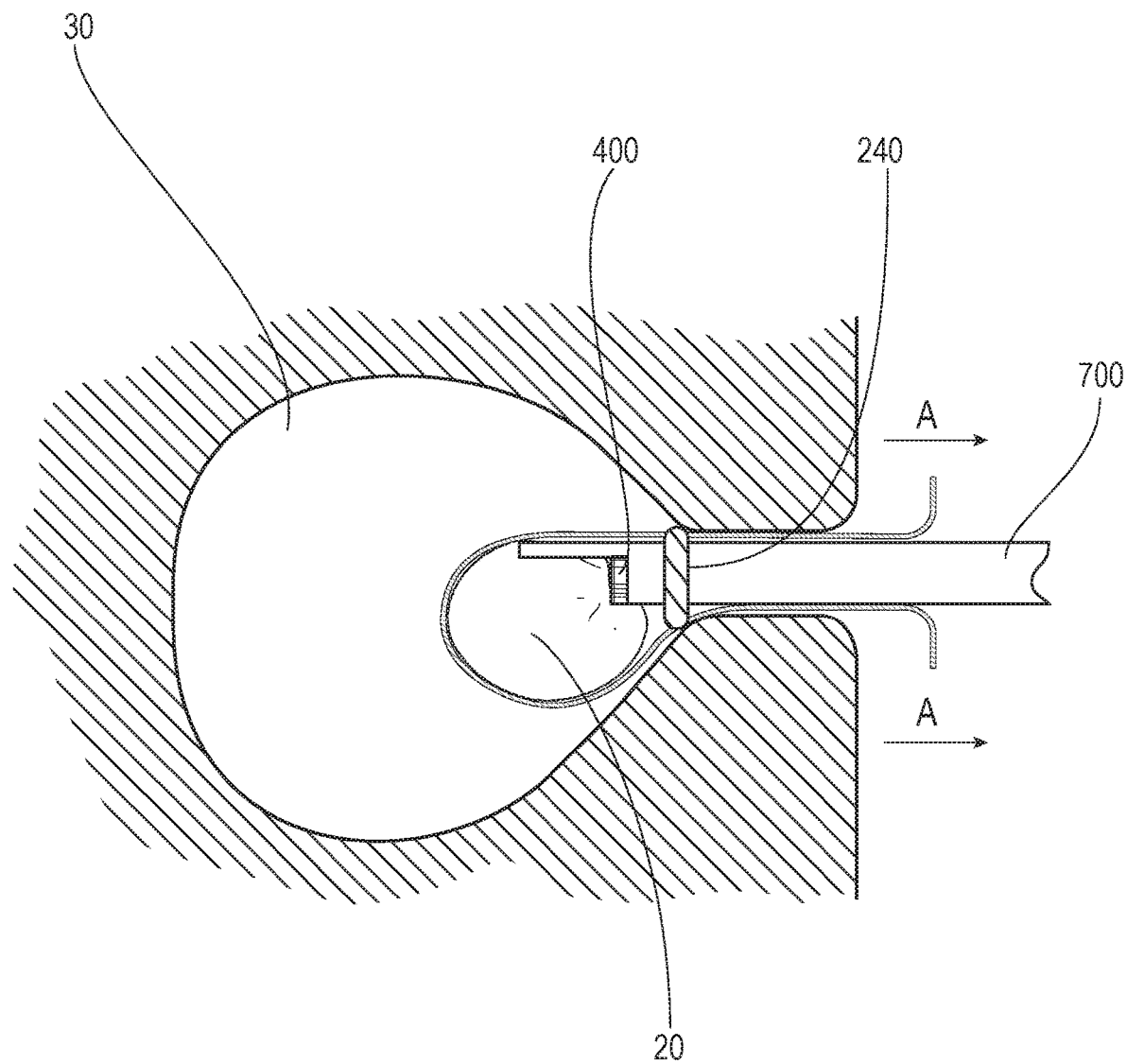
Figure 27:
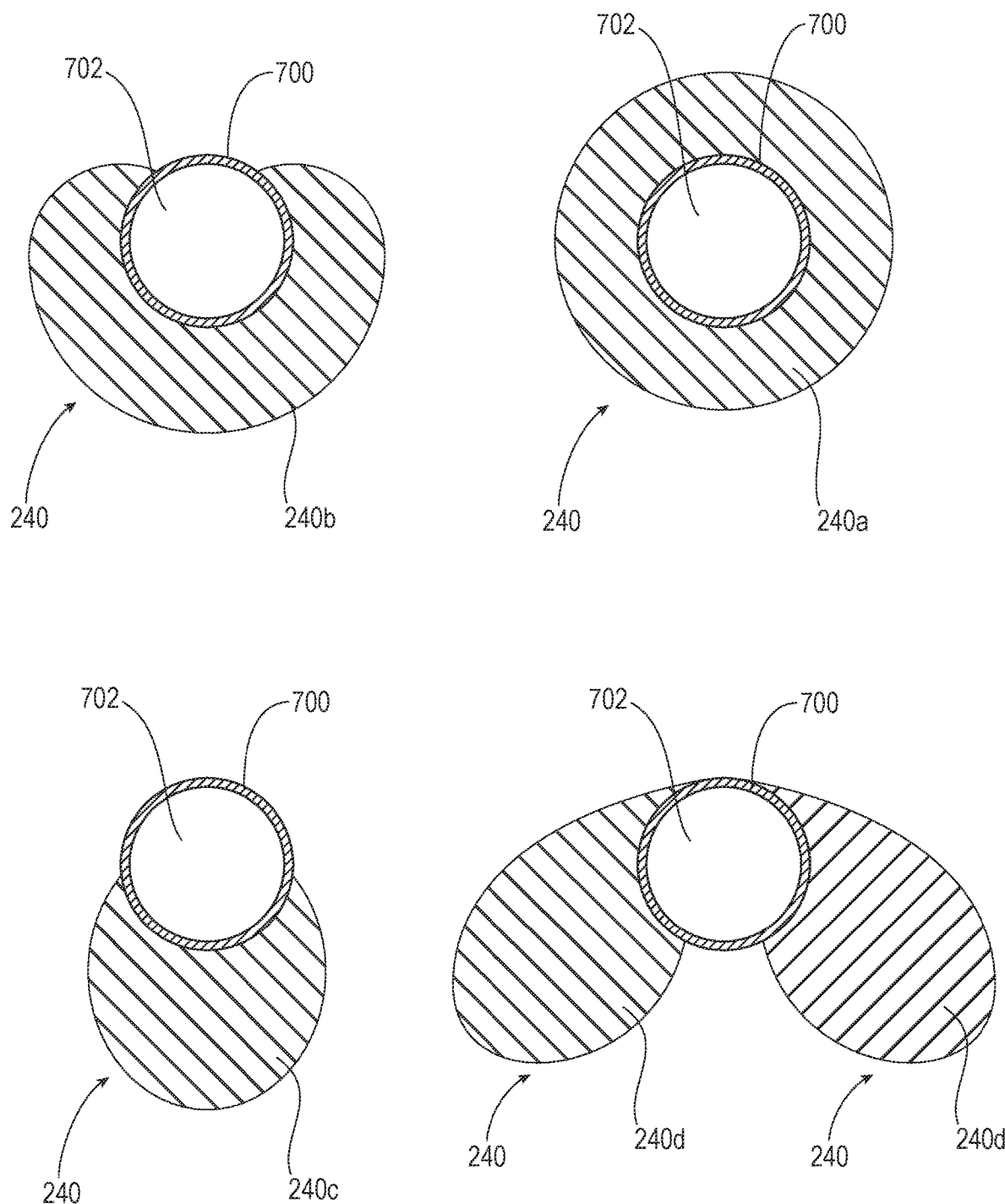
FIG. 27 illustrates various locking member embodiments that may be used with embodiments of the present disclosure.

FIGS. 26-28 schematically depict additional embodiments and methods of their use. FIG. 26A depicts a system 100 of the present disclosure deployed in a patient's body cavity 30, such as a pelvic or abdominal cavity, with tissue specimen 20 captured within container 200, and container opening 206 is disposed outside the patient's body and extending from the port (natural or surgically-created) so that container edge 206a placed as shown. Cannula 700 with cutter 400 are also shown as disposed within container interior 204, consistent with other embodiments and methods described herein.

An additional component in the form of a locking member or balloon 240 is seen as disposed on or around cannula 700 in the embodiments of FIGS. 26-28. While locking member or mechanism 240 is described herein as a balloon having an expandable surface when inflated, other locking components 240 that may be expanded, moved or actuated by fluid means or even by one or more alternative mechanisms, including, e.g., pneumatic pistons, motor-driven lead screws, expanding linkages similar to those used to open and close an umbrella, and the like are contemplated. The description herein is presented in the context of a balloon locking mechanism 240 although such other forms of a locking mechanism may be used.

More than one locking member or balloon 240 may be present in embodiments of the present disclosure, and for purposes of illustration only one balloon is described below. Balloon 240 may be inflated from an uninflated state shown in FIG. 26A to an inflated state shown in, e.g., FIGS. 26B-D to effect its purpose during use. While not shown in the figures, the one or more balloons 240 may be inflated by use of an inflation port, channel, tube or other means attached to an interior 242 of balloon 240. This port, channel, tube or other means may be in fluid communication with a source of inflation fluid (e.g., gas, saline, or other suitable fluid) that may be controlled by a physician or other user to inflate balloon 240 in a controlled manner as desired during methods of use. Balloon 240 may also in some embodiments be deflatable such that a precise amount of inflation (in case of, e.g., inadvertent overinflation or the need for repositioning system 100) may be employed to maximize the effectiveness of system 100 during use. A valve may or may not be present to provide additional control of balloon 240, and inflation/deflation may be controlled manually or automatically, under, e.g., pressure or volume control (via use of devices such as an ENDOFLATOR, etc.).

When locking member 240 is a balloon, it may be made from any suitable medical grade biocompatible material, including urethanes, silicones, plastics of various types, elastomers, PTFE and ePTFE, and be made of single- or multi-ply construction. Balloon 240 may include coatings and/or surface treatments, particular on its outer surface, so to aid it in performing its role as described below during methods of the present disclosure. Balloon 240 may be affixed to cannula 700 or other component by methods known by those of skill in the art, including, e.g., the use of adhesives, welding, mechanical fasteners, or combinations thereof, or balloon may be integrally formed with cannula 700 or other component. Balloon 240 may also include a material on its outer surface, such as, e.g., a covering of a rigid material, a surface treatment, panels, rigid sections, etc. Other forms of locking mechanism 240 may also include such elements.

FIG. 26A depicts a locking member in the form of a single balloon 240 disposed on cannula distal end 752. The precise location of balloon 240 on cannula 700 and/or on other components usable in the present disclosure, and the actual number of balloons used may vary, as may the shape of the balloon(s) when inflated. For instance, between one and five or more balloons may be used, in identical or varying shapes, in system 100 depending on the anatomy into which the system is disposed and the methods and steps used in performing the tissue capture and removal procedure. As may be seen in the examples depicted in the end-on views of balloon 240 embodiments disposed over a cannula 700 in FIG. 27, balloon 240 may be of a simple toroidal shape 240a, a semi-circular shape 240b that does not extend around the entire circumference of cannula 700. A single lobe balloon 240c is also seen along with a dual lobe balloon 240d. Such lobed configurations for balloon 240 may be useful in applications in which a preferential apposition against body tissue or other components of system 100 is desired, such as when the anatomy of the patient requires. Three, four or more lobed balloon configurations are contemplated for certain embodiments. Other shapes amenable to optimized clinical use, such as tapered or crescent shapes and the like may also be used.

After system 100 having locking member or balloon 240 is placed in the desired location by a physician or other user and tissue specimen 20 is captured within container 200 as shown in FIG. 26A, balloon 240 may be inflated as depicted in FIG. 26B. The precise timing of balloon inflation may vary according to the procedure being undertaken and physician preference, but generally it will be inflated prior to the tissue cutting or morcellation process.

Recall that in systems of the present disclosure and accompanying methods, it is useful to employ components and techniques to bring tissue specimen 20 into close proximity of or apposition with cutter 400; namely, blade 408. As previously discussed, this may be accomplished by several means: hand or automatic tensioning of bag 200 so to pull specimen 20 closer to cutter 200, the use of a tenaculum or grasper 500 to pull specimen closer to cutter 200, etc. Balloon 240 affords yet another tool, which may be used singly or in combination with other techniques (e.g., bag tensioning) or components (e.g., grasper 500) to help the physician or other user to achieve this same objective. Ensuring that specimen 20 is placed kept into close proximity or contact with cutter 400 within container interior for tissue processing is a useful aspect of the present disclosure. In one respect, balloon or locking member 240 allows cutter 400 and cannula 700 to be locked in the direction of the body port 22 so that when tension is applied to the container 200 (e.g., by a physician or other user pulling), the cutter 400 and cannula 700 remain locked in to provide counter-tension to the system. FIG. 26B shows that tissue specimen 20 has been moved into apposition with blade 408 by, e.g., tensioning bag 200 and/or by proximal movement of cannula 700. An advantage of balloon 240 is that users of systems 100 of the present disclosure that include one or more balloons may not need a grasper 500 in order to effect the proper apposition and tensioning of specimen 20 as desired. This provides an alternative, simple procedure capture, cut and remove tissue specimen 20. In fact, in some embodiments, balloon 240 may replace altogether the need for grasper 500. An embodiment that does or does not have the grasper can incorporate a uterine manipulator (not shown) that can be inserted through a central lumen of the cannula or the cutter.

As the physician or other user moves components of system 100 (e.g., cannula 700 and/or container 200) proximally in a direction A so to pull specimen 20 close to or in apposition with blade 408, balloon 240 as shown in FIG. 26C concomitantly moves in the same proximal direction until it abuts the patient's tissue surface within cavity 30. In this fashion, balloon 240 is "anchored" against the patient's body tissue in the cavity 30, for instance, against a cervical opening in a pelvic cavity. This frees the physician or other user from having to hold cutter 400 in a particular axial location or position during the cutting process. As a result, the physician or other user may concentrate more fully on tensioning or pulling bag 200 as described elsewhere in the present disclosure and to operate cutter to process specimen 20. FIG. 26D depicts this tensioning on bag (as shown by arrows A) outside the patient's body as the cutter 400 disposed inside cannula lumen 702 is activated to cut or morcellate specimen 20. Balloon 240 serves to anchor the system 100 in place as seen in FIG. 26D, preventing cannula 700 from otherwise moving proximally in the direction of arrows A; this provides counter-traction such that the bag 200 is applying force on the tissue specimen 200 in the direction of cutter 400.

In addition to obviating the need for a tissue grasper 500, systems of the present disclosure employing one or more balloons affords several other advantages, including serving as a guard by the balloon or balloons acting as a barrier between cutter 400 (especially blade 408), optionally grasper 500, and the container interior 204 into which the cutter is disposed and the grasper may be disposed. The balloon or balloon may be properly sized and located on or near the distal end 752 of cannula 700 to create geometric tenting points that physically prevent container 200 from coming into contact with, or even close to, blade 408 or the optional grasper 500, including jaws 510. As such, these systems may also supplement the function of a guard 300 or protector feature as discussed herein, and may in some embodiments obviate the need for a guard or protector feature altogether, increasing simplicity of operation, lowering system cost, reducing procedure time, etc. The simplicity of such a system 100 employing one or more balloons is a particularly advantageous feature, as during a method of use, the physician or other operator engages the cutter 400 to process the tissue specimen 20 once the system is in place in the patient's body and pulling on container (via any number of techniques discussed herein) to maintain the desired tension, complete the tissue morcellation process, and remove the container from the patient's body. Such a process may be used in any of the methods or applications described herein, including gynecological procedures such as hysterectomies, etc.

Figure 28A:
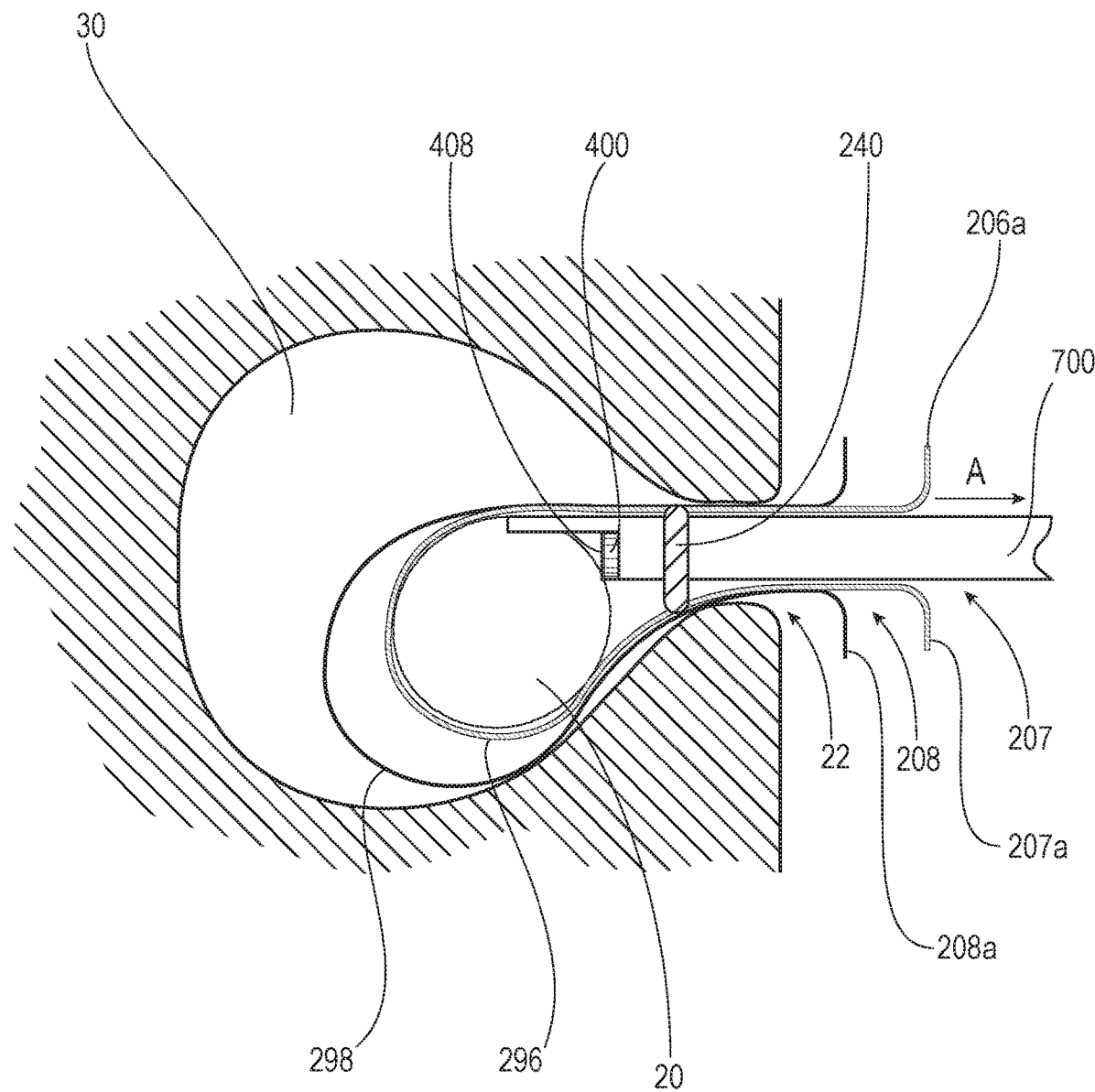
FIGS. 28A-C depict embodiments employing one or more balloons and two separate containers.
Figure 28B:
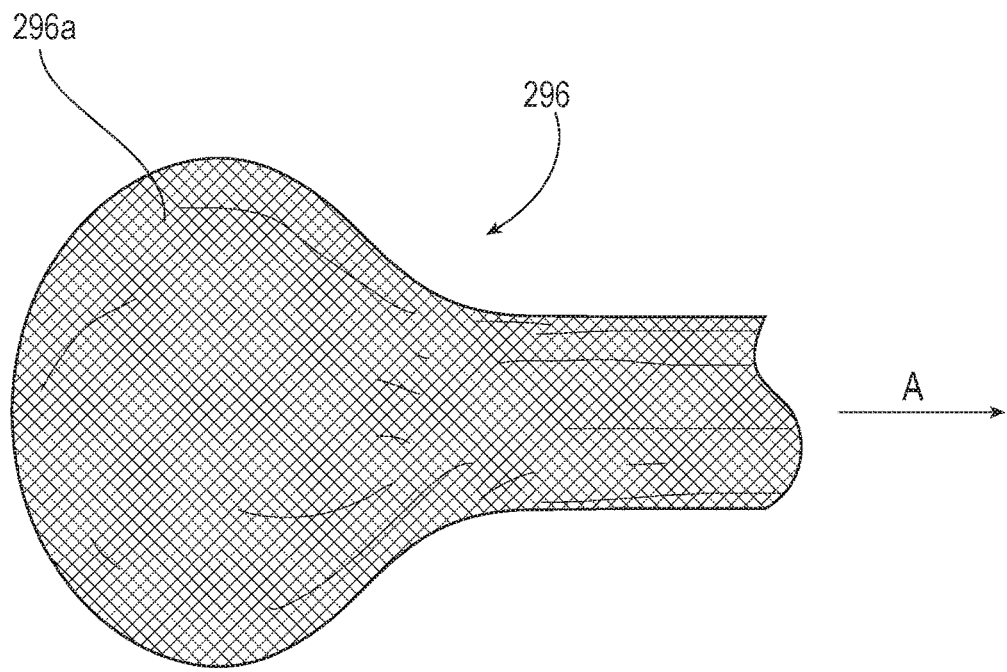
Figure 28C:
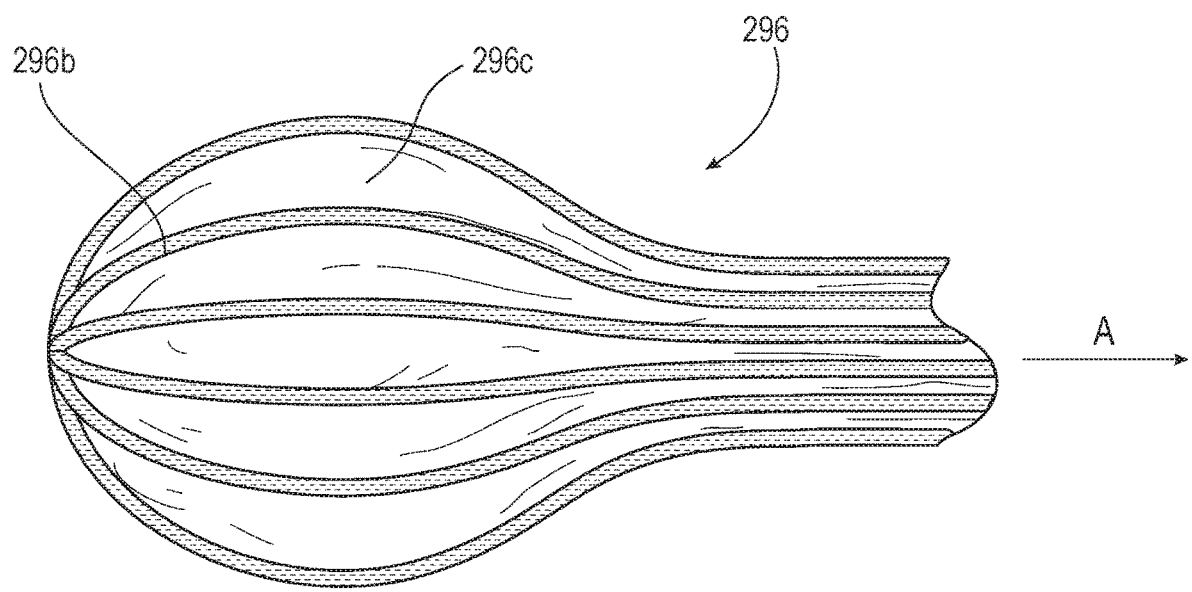

Turning to FIGS. 28A-C, system embodiment 100 employing one or more balloons 240 and two separate containers 200 is illustrated. This embodiment of system 100 may also be suitable for use without a tissue grasper, uterine manipulator, or other tool to assist in positioning the tissue specimen 20 in preparation for and during the cutting process.

FIG. 28A depicts a system 100 of the present disclosure deployed in a patient's body cavity 30, such as a pelvic or abdominal cavity, with tissue specimen 20 captured within a container 200 having two bags or containers inner bag 296 and outer bag 298. Openings 207 and 208 of each of inner and outer bags 296 and 298, respectively, are disposed outside the patient's body and extending from the port (natural or surgically-created) so that inner container edge 207a and outer container edge 208a are placed as shown. Cannula 700 with cutter 400 are also shown as disposed within an interior of inner container 296, consistent with other embodiments and methods described herein. FIG. 28A also shows that inner container 296 having specimen 20 therewithin is itself disposed within an interior of outer container 298.

Cutter 400 is seen in FIG. 28A as at least partially disposed within the interior of inner bag 296. Cutter blade 408 is shown in apposition to tissue specimen 20 in a manner suggesting the beginning of the cutting process as described elsewhere herein. For example, balloon 240 is inflated in the view of FIG. 28A and in apposition against the patient's body tissue as described above in connection with methods and devices shown in FIGS. 26-27.

With a dual-bag design for container 200, specialized roles may be played by each bag and, therefore, each bag may have specific design attributes that may translate into specific properties and features. For instance, container 200 may be designed such that only inner bag 296 is in contact with specimen 20, while outer bag, which encloses inner bag 296 within its interior, may be designed to ensure bodily fluid and cellular impermeability. These differing designs may afford certain advantages in performance, cost, ease of use, and manufacturability given that a single bag, even if of a composite or bi-layer design, would by itself need to be designed to satisfy all design criteria according to embodiments disclosed herein.

Inner bag 296 may particularly be designed to have a high resistance to plastic deformation under axial loading so that the tensioning steps described herein may be safely and effectively accomplished. In particular, and as shown in FIG. 28A, openings 207 and 208 of inner and outer bags, respectively, extend out of the patient's body through port or opening 22, whether that port is a surgically-created port or a naturally existing port (e.g., a vagina). In this configuration and as described elsewhere, any number of manual and automated techniques and components may be used to tension container 200 so to bring specimen 20 into apposition with or near the cutter 400 and in particular cutter blade 408, to shorten a length of inner container 296. In a simple embodiment of tensioning, a physician or other user pulls axially on a proximal end of inner container 296 by hand, optionally including a twisting motion as described elsewhere. A rolling technique, with or without rings or other components as described elsewhere herein, may be additionally utilized to apply the requisite tension in an efficient manner. Thus, a premium may be placed on an inner bag 296 having a relatively high axial strength, modulus of elasticity, and resistance to deformation under tension as described above.

Outer bag 298 may particularly be designed to have a high impermeability to fluid transfer through its walls, especially insofar as it may be impervious to leakage of cellular material (cancerous, non-cancerous, or pre-cancerous) and body fluids associated with tissue specimen 20. Given the outer bag's proximity immediately adjacent the body cavity 30 in which it is placed, outer bag 298 is the last line of defense against cavity 30 being contaminated with body fluids or tissue portions during specimen cutting and removal, thus demonstrating the relative importance of this criterion in connection with a dual-bag system 100.

In concert, inner bag 296 and outer bag 298 of this embodiment of container 200 have the attributes desired for optimal performance of a container; e.g., high fluid and tissue impermeability and high strength as described above. Other attributes, such as tear and puncture resistance, optical transmissibility, amenability to doping, use of markings such as grid/gradation lines, etc., specialized electrical or thermal properties, manufacturability, ability to be rolled, folded or compressed into a small space, etc. may also be designed into the inner and outer bags as desired.

Inner bag 296 may in fact be permeable or semi-permeable to fluids/tissues in some embodiments, while in others it may be designed to be fluid- and tissue-impermeable. In embodiments where inner bag 296 is fluid/tissue permeable or semi-permeable, it is nonetheless strong enough as described above to perform optimally during the methods described herein, including tensioning and tissue cutting and removal. For example, inner bag 296 may be constructed of a metallic material, such by a series of linkages or chains 296a (akin to a "chain mail" bag), to withstand large tensile forces and to prevent cutting by the tissue cutting device itself as illustrated in FIG. 28B. Alternatively, inner bag 296 may a composite itself, constructed of high tensile-strength strips of metallic or plastic material 296b embedded in or attached to a plastic or metallic material 296c forming the inner bag as shown in FIG. 28C. Various high-strength plastics may be used to construct or comprise such strips. Alternatively, inner bag 296 may be a single layer of material, such as isotropic PTFE and ePTFE extrusions or layered constructions in which a preferentially high tensile strength is achieved in the direction in which tensioning is to be applied, are also contemplated.

During use, system 100 as shown in FIG. 28A has been deployed as shown, with various techniques and components described herein employed to prepare and place specimen 20 within the inner bag. A tissue grasper 500 and/or laparoscopic tool may also be used to assist in placing specimen 20 in an interior of inner bag 296. Inner bag may have been prepared by being deployed within an interior of outer bag 298, either prior to the procedure as described herein or after outer bag 298 has been deployed into cavity 30 (either through a surgical or natural port). Inner bag 296 may also have been packaged within an interior of outer bag 298 so that the physician or other user may deploy both inner and outer bags as a single unit when placing container 200 into cavity 30. Once the physician or other user has pulled edges 207a and 208a of inner and outer bags out of the body port so that each of the bags' openings are outside the patient's body, locking member in the form of a balloon or balloons 240 may be inflated as discussed above. At this point, the physician or other user may continue apply tension on inner bag 296 by pulling in a proximal direction indicated by arrow A so to move tissue specimen 20 closer to the body opening 22, shortening inner bag 296. Outer bag 298 may or may not be similarly tensioned during this process depending on user preference and the particular anatomy and indication being treated. Clearly the accomplishment of tissue specimen 20 apposition against or near cutter 400 and blade 408 may be achieved by tensioning inner bag 296 alone or alternatively tensioning outer bag 298 alone or with inner bag 296. As described above, the anchoring effect of locking member 240 in the form of a balloon as shown in place in FIG. 28A frees the physician or other operator from having to hold cannula and/or cutter during the cutting process. As tissue specimen 20 is morcellated, tension may be applied on inner bag 296 and/or optionally on outer bag 298 to maintain the proper alignment of specimen 20 and cutter 400 and to cut or morcellate specimen 20 in the desired manner. Once specimen has been processed, it may be removed from the patient's body, the cutter/cannula may be removed, and finally inner and outer bags 296, 298 forming container 200 separately in sequence or together may be removed from the patient's body. Embodiments of the systems shown in FIGS. 26-28 may include a dual-bag or a single bag container 200. In addition, it is within the scope of the present disclosure to use the dual-bag embodiment shown in FIG. 28 with or without the use of one or more locking members 240, as well as other components described herein.

In an example of a transvaginal uterine capture and removal method of the present disclosure using the system shown in FIG. 28, the inner and outer bags may be deployed into a patient's pelvic cavity either through a surgical port (not shown) in the abdominal wall or through the vagina. Once the uterus and any attendant organs/tissue has been prepared for removal, the process as described above may be employed to place the uterus into the inner bag 296, tension applied to inner bag 296 to bring the uterus near the vaginal cuff in the pelvic cavity and near or against the cutter blade 408. The cutting process may be employed to morcellate the uterus 20 and remove it through the vagina from within an interior of inner bag 296. The outer bag 298 may be removed concurrently with or after removal of inner bag, both through the vagina, and optionally one or both of inner and outer bags may be closed to keep any tissue or fluids escaping therefrom.

In another example of a transvaginal uterine capture and removal method of the present disclosure using the system of FIGS. 26-27, container 200 may be deployed into a patient's pelvic cavity either through a surgical port (not shown) in the abdominal wall or through the vagina. Once the uterus 20 and any attendant organs/tissue has been prepared for removal, the process as described above may be employed to place the uterus into container 200 and apply tension thereto to bring the uterus near the vaginal cuff in the pelvic cavity and near or against the cutter blade 408.

Balloon 240 or balloons 240 may be inflated before, during or after the container tensioning step as the physician or other user sees fit. The cutting process may be employed to morcellate the uterus 20 and remove it through the vagina from within container interior 204.

Three main advantages, among others, are afforded by the systems employing one or more locking members such as the balloons 240 shown in the exemplary embodiments and methods described herein in connection with FIGS. 26-28: first, the locking member 240 may be used solely or supplementally with other guard/protector features as a guard. Second, the locking member 240 serves as an anchoring mechanism to lock or hold the cutter 400 and/or cannula 700 within which it is disposed, in place. Third, the presence and use of one or more locking members 240, such as balloons 240, supplements or even replaces the function of a tissue grasper 500 to impart counter-tension against cutter 400 during methods described herein as well as application of tension on container 200, with or without separate tensioning member or members, to pull the tissue specimen 20 against the cutter edge 408. Of course, it is within the scope of the present disclosure that systems employing one or more locking members, such as balloons 240, may be used in conjunction with components such as grasper 500, guard 300, protector portions 774, 775 and the like. It is also within the scope of the present disclosure that methods employing systems having one or more locking members, such as balloons 240, may use various techniques and tools as described herein to effect safe and proper capture, apposition, and processing of tissue specimen 20. However, the aforementioned advantages of locking members, together with other advantages such as cost reduction, ease of use, reduced complication risk, etc., make the use of such systems without additional components or techniques attractive.

In all of the examples described herein with respect to an inner and outer bag embodiment, as well as with other embodiments, the bags may be designed and employed such that no tissue grabber or other tool is necessary to achieve the methods undertaken to capture and remove tissue, thus simplifying the method as an additional tool and method steps need not be utilized.

In the example methods described above in connection with FIGS. 23-28 as well as other figures detailed in the present disclosure, certain details have been omitted for clarity. For example, proximal portions of the various components herein, including handles, triggers, hand cranks, motors, stops to control the depth of cutter blade 408, foot pedals and the like are understood variously to be available to the physician or other user when accomplishing the methods of the present disclosure, including those described below. In addition, while these methods may include use of a cannula 700 in connection with the use of cutter 400 and grasper 500, use of such cannula is optional and the methods of the present disclosure need not include such a cannula. In addition, guard 300 or protector elements such as elements 746, 778, extension 776, etc. may be integrated with or attached to cutter 400, or even tissue grasper 500, rather than cannula 700. The function of tissue grasper or tenaculum 500 may be accomplished through components or features on cannula 700 and/or cutter 400, and so a separate grasper or tenaculum 500 is also optional and need not be present to accomplish the methods described herein. For example, if the physician or other operator places enough tension on container 200 using the systems and methods discussed herein, there may be no need for a tissue grasper or tenaculum 500: the physician or other user can simply apply such axial tension on enclosure 200 to bring the tissue specimen 20 in the vicinity of or in apposition to cutter blade 408 to suffice for adequate cutting or morcellating and removal of specimen 20 as described herein.

Other Examples

The systems and components described in the present disclosure may be used in a variety of mammalian body locations. These systems and components are useful many circumstances, but especially those in which a relatively large tissue specimen must be safely removed through a relatively small port, whether that port be surgically created or a natural opening in the patient's body. Of course, the relative sizes of the systems and various components may be tailored to suit the specific application for which it is being used. For example, systems of the present disclosure used to capture and retrieve a tissue specimen, such as a cyst or tumor, from a lung via the trachea and perhaps accessed via the mouth or a nasal passage will be different than a system for a transvaginal hysterectomy. Moreover, components within a single system be sized differently relative to one another than respective components in a different system designed to treat a particular indication. We have found this to be a platform technology suitable for use in many applications. As such, each of the various examples described in the present disclosure should not be considered as limiting but rather exemplary of the platform concepts; modifications to relative dimensional recitations and departures from certain design features are considered to be within the scope of the present disclosure.

Gynecologic Applications

As described herein, systems 100 of the present disclosure are suitable for use in benign gynecological applications, including vaginal hysterectomy, laparoscopic assisted vaginal hysterectomy, laparoscopic hysterectomy, robotic assisted laparoscopic hysterectomy, and even open hysterectomy via a mini-laparotomy. In the realm of laparoscopic and robotic assisted laparoscopic, the systems 100 of the present disclosure are equally useful in using any configurations of ports including three-port, four-port or five-port. In connection with such uses, any number or combination of cameras, device "arms," and assistant ports are possible, although embodiments of the present disclosure may be used without such ports and their respective tools, especially those embodiments that can be introduced via a natural body port such as the vagina. The ability for systems of the present disclosure to work without an assistant port, necessary in other morcellation systems, renders systems disclosed herein as useful in "single site" robotic assisted hysterectomies as well.

Myomectomy: other embodiments of systems described herein may be deployed via an abdominal port for the purpose of morcellating uterine fibroids in connection with a myomectomy. Given that myomectomy procedures typically do not involve an incision such as a colpotomy, no component needs to be introduced vaginally.

Ovarian cystectomy, oophorectomy and salpingectomy: smaller, scaled-down versions of the embodiments of the present disclosure may be deployed via abdominal ports for the purpose of morcellating ovaries, fallopian tubes, ovarian cysts, tumors, or other solid or non-solid masses—tissues that otherwise would be difficult or impossible to remove via laparoscopic ports or small transabdominal incisions using known devices and techniques.

Gynecologic oncology: embodiments of systems disclosed herein are suitable for performing hysterectomies associated with gynecologic malignancies or suspected gynecologic malignancies (including, e.g., uterine, ovarian, adnexal, cervical, omental and abdominal). Enclosure of the tissue specimen to be removed in containers disclosed herein prevents spillage of cancerous cells into the abdomen and pelvis.

Non-Gynecologic Applications

Embodiments of the present disclosure that are port-deployed, transabdominally deployed, transdermally deployed and deployed by other means are useful in various non-gynecologic procedures, including surgeries being performed for removing benign, malignant, or suspicious tissue in various locations in the body. Examples include bowel resection, colectomy, hemi-colectomy, as well as surgery for renal, adrenal, rectal, and bladder conditions. Head and neck surgery (including, e.g., surgery for thyroid conditions), cardiothoracic surgery (including, e.g., video assisted thoracic surgery (VATS) for pulmonary, cardiac, or other conditions) are other classes of treatment in which systems of the present disclosure are useful. Currently, minimally invasive procedures for these indications require that the patient indeed receive a large, open incision for the purpose of liberating the specimen once it has been robotically dissected away from the body. Use of our bag/morcellator will both protect the specimen from spillage into the body cavity while simultaneously obviating the need for a large incision at the conclusion of the case—an incision which of course negates many of the advantages of minimally invasive surgery.

Features described herein with respect to different methods of use or different features, instruments, components, or their order of use may interchangeably be used among the various methods without taking away from the spirit of the methods and devices of the present disclosure. The presence or absence of a particular step or component should not be construed as limiting the methods described herein, With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments discussed. Accordingly, it is not intended that the invention be limited by the foregoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claims that follow.

What is claimed is:

1. A tissue containment and removal system, comprising:
   a tissue container including an opening, an interior volume, and a composite multiple layer structure that includes a watertight layer and a reinforcement member which is resistant to cutting or puncturing;
   a tissue cutter including a distal end, a central lumen which extends from the distal end to a proximal portion of the tissue cutter and which is configured for pulling morcellated tissue therethrough and out of the proximal portion of the tissue cutter, a cutter blade disposed on the distal end and an outer dimension that is at least partially disposable through the opening and within the interior volume of the tissue container;
   a cannula which is at least partially disposable through the opening and within the interior volume of the tissue container, the cannula including a central lumen which serves as a conduit and smooth working channel for the tissue cutter through which the tissue cutter is configured to be disposed and positioned with an edge of the cutter blade extending distally of a distal end of the cannula and with the tissue container remaining open to the outside during morcellation of tissue within the interior volume of the tissue container; and
   at least one mechanical stop which is disposed on the tissue cutter and which is used to position the edge of the cutter blade to extend distally up to about 50.0 mm from the distal tip of the cannula during morcellation.

2. The tissue containment and removal system of claim 1 wherein the reinforcement member includes metal wires.

3. The tissue containment and removal system of claim 1 wherein the reinforcement member includes a metal mesh.

4. The tissue containment and removal system of claim 1 wherein the reinforcement member includes a series of metallic linkages.

5. The tissue containment and removal system of claim 1 wherein the reinforcement member includes a curved cross-sectional profile having a radius of curvature that is configured to optimize its radial stiffness and resistance to lateral bending or rolling up against the radius while being relatively flexible in the opposite direction.

6. The tissue containment and removal system of claim 1 wherein the reinforcement member has a thickness of about 0.1 mm to about 4.0 mm.

7. The tissue containment and removal system of claim 1 wherein the composite multiple layer structure of the tissue container comprises a bi-layer construction wherein the watertight layer comprises an outer layer and the reinforcement member comprises an inner layer.

8. The tissue containment and removal system of claim 1 wherein the composite multiple layer structure of the tissue container is impermeable to the transmission or leakage of biological cells.

9. The tissue containment and removal system of claim 1 wherein the tissue container comprises an opening having a diameter of about 50.0 mm to about 400 mm.

10. The tissue containment and removal system of claim 1 wherein the tissue container comprises a size of about 300 mm by 300 mm by 400 mm.

11. The tissue containment and removal system of claim 1 wherein the tissue container further comprises tabs.

12. The tissue containment and removal system of claim 1 further comprising a tissue grasper at least partially disposable within the tissue container interior.

13. The tissue containment and removal system of claim 12 wherein the tissue grasper is at least partially disposable within and axially movable through the central lumen of the tissue cutter.

14. The tissue containment and removal system of claim 12 wherein the tissue grasper is at least partially disposable within and axially movable through the central lumen of the cannula.

15. The tissue containment and removal system of claim 1 wherein the tissue cutter comprises a cylindrical structure with a rotating cutter blade.

* * * * *

UNITED STATES PATENT AND TRADEMARK OFFICE
CERTIFICATE OF CORRECTION

PATENT NO.        : 10,695,091 B2
APPLICATION NO.   : 16/169884
DATED             : June 30, 2020
INVENTOR(S)       : Steven Kim, Joseph Marchesani and Alexey Salamini Page 1 of 1

It is certified that error appears in the above-identified patent and that said Letters Patent is hereby corrected as shown below:

On the Title Page

Related U.S. Application Data should read:

"(63) Continuation of application No. PCT/US2017/029162, filed on Apr. 24, 2017, now expired.

(60) Provisional Application No. 62/419,342, filed Nov. 8, 2016.
Provisional Application No. 62/326,836, filed Apr. 25, 2016."

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*